United States Patent
Haase et al.

(10) Patent No.: US 11,225,450 B2
(45) Date of Patent: *Jan. 18, 2022

(54) PROCESSES FOR PREPARING CALIXARENES

(71) Applicant: SI GROUP, INC., Schenectady, NY (US)

(72) Inventors: Cornelius Haase, Schenectady, NY (US); Ricky Biittig, Schenectady, NY (US); Allyson Staats, Schenectady, NY (US); Philip David Atwood, Schenectady, NY (US); Jim Webb, Ballston Lake, NY (US); Kelly Chichak, Schenectady, NY (US)

(73) Assignee: SI GROUP, INC., Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/087,422

(22) Filed: Nov. 2, 2020

(65) Prior Publication Data

US 2021/0047253 A1 Feb. 18, 2021

Related U.S. Application Data

(63) Continuation of application No. 16/992,747, filed on Aug. 13, 2020, now Pat. No. 11,072,572, which is a continuation of application No. 16/271,499, filed on Feb. 8, 2019, now Pat. No. 10,781,154.

(60) Provisional application No. 62/628,472, filed on Feb. 9, 2018.

(51) Int. Cl.
*C07C 37/20* (2006.01)
*C08G 8/00* (2006.01)
*B01J 31/02* (2006.01)
*C07C 39/15* (2006.01)
*C08G 8/12* (2006.01)

(52) U.S. Cl.
CPC .......... *C07C 37/20* (2013.01); *B01J 31/0239* (2013.01); *B01J 31/0244* (2013.01); *C07C 39/15* (2013.01); *C08G 8/12* (2013.01)

(58) Field of Classification Search
CPC ............ C07C 37/20; C07C 39/15; C08G 8/12
See application file for complete search history.

(56) References Cited

U.S. PATENT DOCUMENTS

| | | | |
|---|---|---|---|
| 2,868,844 A | 1/1959 | Coffield et al. | |
| 3,870,669 A | 3/1975 | Hofel et al. | |
| 5,378,791 A | 1/1995 | Lancaster et al. | |
| 5,952,526 A | 9/1999 | Lamartine et al. | |
| 6,200,936 B1 | 3/2001 | Moreton | |
| 6,271,337 B1 | 8/2001 | Lamartine et al. | |
| 6,984,599 B2 | 1/2006 | Nagy | |
| 7,524,469 B2 | 4/2009 | Meikrantz et al. | |
| 9,333,465 B2 | 5/2016 | Diep et al. | |
| 9,695,209 B2 | 7/2017 | Dauvergne | |
| 10,466,590 B2 | 11/2019 | Imada | |
| 2012/0145542 A1 | 6/2012 | Nakamura et al. | |
| 2015/0232603 A1 | 8/2015 | Huc et al. | |
| 2016/0108231 A1 | 4/2016 | Aube et al. | |
| 2017/0051224 A1 | 2/2017 | Notari et al. | |
| 2019/0100685 A1 | 4/2019 | Cable | |

FOREIGN PATENT DOCUMENTS

| | | |
|---|---|---|
| EP | 0447977 A1 | 9/1991 |
| EP | 0480658 A2 | 4/1992 |
| EP | 2599814 A1 | 6/2013 |
| WO | 2017/025900 A1 | 2/2017 |
| WO | 2017/087115 A1 | 5/2017 |

OTHER PUBLICATIONS

Munch et al., "p-tert-BUTYLCALIX[8]ARENE," Organic Syntheses, CV 8, 80 68: 243 (1990).
Gutsche et al., "Pathways for the Reversion of p-tert-Butylcalix[8]arene to p-tert-Butylcalix[4]arene," J. Org. Chem. 64: 3747-3750 (1999).
Burlini, "Synthesis of New Calixarene-Based Lubricant Additives," Doctoral Dissertation for Universita' Degli Studi di Parma, Dottorato di ricerca in Scienza e Tecnologia dei Materiali Innovativi, ciclo XXVIII (2016).
Stewart et al., "Isolation, Characterization, and Conformational Characteristics of p-tert-Butylcalix[9-20]arenes," J. Am. Chem. Soc. 121: 4136-4146 (1999).
Dhawan et al., "Calixarenes. 10. Oxacalixarenes," J. Org. Chem. 48: 1536-1539 (1983).
Vocanson et al., "Characterization of synthetic precursors of p-tert-butycalix[4]arene and p-tert-butylcalix[8]arene. Mechanisms of formation of calix[4]arene and calix[8]arene", Supramolecular Chemistry 7: 19-25 (1996).
Vocanson et al., "Characterization of precursors of p-tert-butycalix[6]arene synthesis. Mechanism of formation of p-tert-butylcalix[6]arene," Supramolecular Chemistry 4:153-157 (1994).
Gutsche, "Calixarenes: An Introduction, 2nd Edition," RSC Publishing, pp. 30-31 and 236-237 (2008).
Neri et al., eds., "Calixarenes and Beyond," Springer, pp. 142-143 and 168-173 (2016).
Gutsche, "Synthesis of Calixarenes and Thiacalixarenes," in Calixarenes 2001: Kluwer Academic Publishers, pp. 1-25 (2001).
Gutsche, "Calixarenes," Royal Society of Chemistry: Chapters 2-3 (1989).

(Continued)

*Primary Examiner* — Sikarl A Witherspoon
(74) *Attorney, Agent, or Firm* — Jeffrey N. Townes; Cozen O'Connor

(57) ABSTRACT

This invention relates to a process for preparing a calixarene compound by reacting a phenolic compound and an aldehyde in the presence of at least one nitrogen-containing base as a catalyst to form the calixarene compound. The invention also relates to processes for high-yield, high solid-content production of a calixarene compound, with high selectivity toward a high-purity calix[8]arene compound, without carrying out a recrystallization step.

25 Claims, 33 Drawing Sheets

(56) References Cited

OTHER PUBLICATIONS

Blanc, Alexandre, C. et al., "The preparation and use of novel immobilised guanidine catalysts in base-catalysed epoxidation and condensation reactions," Green Chemistry, Royal Society of Chemistry, GB, Nov. 1, 2000, pp. 238-288.

Dhawan, Balram, et al., "Calixarenes, 19a) Studies of the formation of calixarenes via condensation of p-alkylphenols and formaldehyde", Die Makomolekulare Chemie, vol. 188, Jan. 1, 1987, pp. 921-950.

Gutsche, C. David, et al., "Calixarenes. 4. The Synthesis, Characterization, and Properties of the Calixarenes from p-tert-Butylphenol," Journal of the American Chemical Society, Jul. 1, 1981, pp. 3782-3792.

PROCESSES FOR PREPARING CALIXARENES

This application is a continuation of U.S. patent application Ser. No. 16/992,747, filed Aug. 13, 2020, which is a continuation of U.S. patent application Ser. No. 16/271,499, filed Feb. 8, 2019, now U.S. Pat. No. 10,781,154, which claims priority to U.S. Provisional Application No. 62/628, 472, filed on Feb. 9, 2018, which is herein incorporated by reference in its entirety.

FIELD OF THE INVENTION

This invention generally relates to a process for preparing calixarenes.

BACKGROUND

Calixarenes have found widespread uses as complexation hosts and as frameworks for the construction of more complex structures. Calixarene compounds are typically synthesized by using an alkaline base, such as sodium hydroxide, as a catalyst. To obtain a high calixarene concentration in the product, the reaction system was often times diluted. Additionally, to obtain a high purity and high selectivity of a calixarene compound having a particularly ring size, recrystallization of the obtained cyclic reaction product was typically necessary. For instance, the procedure reported by Munch et al., in *Organic Syntheses* 68:243-46 (1990), describes the synthesis of para-tert-butylcalix[8] arene in the presence of sodium hydroxide as the catalyst with a yield of 60-65%. In the Munch process, the synthesis was conducted in an excessive amount of xylene, and to obtain a high purity of para-tert-butylcalix[8]arene, the crude cyclic reaction product, containing about 10-13% of other calixarene oligomers (e.g., calix[4]arene and calix[6] arene), was recrystallized. This procedure was described as the best-yielding, state of art synthetic procedure for preparing a calix[8]arene compound according to C. David Gutsche, Calixarenes, An Introduction (The Royal Society of Chemistry, Cambridge, UK, $2^{nd}$ Ed. 2008), pages 30-31; and Placido Neri et al., Calixarenes and Beyond (Springer International Publishing AG Switzerland, 2016), pages 142-143.

A similar procedure for synthesizing para-tert-butylcalix [8]arene was also described in U.S. Pat. No. 5,736,289 to Sukata et al., as a one-step synthesis, using an alkaline base catalyst, such as potassium hydroxide, in an excessive amount of xylene. In Sukata, although the yield of a white powder (the white powder was identified as cyclic compounds mainly containing para-tert-butylcalix[8]arene) was 85%, the yield of para-tert-butylcalix[8]arene in the white powder was unknown. Other cyclic oligomers besides para-tert-butylcalix[8]arene may have been present in the powder; moreover, Sukata noted that some of the cyclic compounds in the white powder were metallized with potassium. Thus, the procedure disclosed in Sukata also does not provide a high yield, high purity, and high selectivity synthesis of a calix[8]arene compound.

Therefore, there remains a continuing need in the art to develop a high-yield process to prepare calixarene compounds, in particular a calix[8]arene compound, with a high purity and high selectivity, without the need for more complicated purification steps, such as a recrystallization step. This invention answers that need.

SUMMARY OF THE INVENTION

One aspect of the invention relates to a process for preparing a calixarene compound, comprising reacting a phenolic compound and an aldehyde in the presence of at least one nitrogen-containing base as a catalyst to form the calixarene compound.

In certain embodiments, the nitrogen-containing base is a sterically hindered amine or a tetraalkyl ammonium hydroxide.

In certain embodiments, the nitrogen-containing base is an amidine compound having the formula of

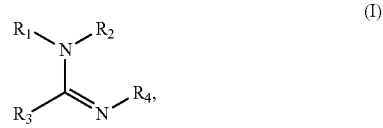

wherein $R_1$, $R_2$, $R_3$, and $R_4$ are each independently H, alkyl, cycloalkyl, heterocycloalkyl, aryl, or heteroaryl; or any two or more of $R_1$, $R_2$, $R_3$, and $R_4$ can be bonded together to form a five- to nine-membered ring structure. In one embodiment, the amidine compound is selected from the group consisting of 1,8-diazabicyclo[5.4.0]undec-7-ene (DBU), 1,5-diazabicyclo[4.3.0]non-5-ene (DBN), 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1, 4,5,6-tetrahydropyrimidine, and 1-ethyl-2-isopropyl-1,4,5, 6-tetrahydropyrimidine.

In certain embodiments, the nitrogen-containing base is a guanidine compound having the formula of

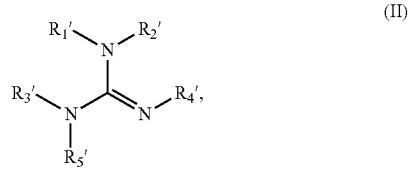

wherein $R_1'$, $R_2'$, $R_3'$, $R_4'$, and $R_5'$ are each independently H, alkyl, cycloalkyl, heterocycloalkyl, aryl, or heteroaryl; or any two or more of $R_1'$, $R_2'$, $R_3'$, $R_4'$, and $R_5'$ can be bonded together to form a five- to nine-membered ring structure. In one embodiment, the guanidine compound is selected from the group consisting of 1-methylguanidine, 1-n-butylguanidine, 1,1-dimethylguanidine, 1,1-diethylguanidine, 1,1,2-trimethylguanidine, 1,2,3-trimethylguanidine, 1,3-diphenylguanidine, 1,1,2,3,3-pentamethylguanidine, 2-ethyl-1,1, 3,3-tetramethylguanidine, 1,1,3,3-tetramethyl-2-n-propylguanidine, 1,1,3,3-tetramethyl-2-isopropylguanidine, 2-n-butyl-1,1,3,3-tetramethylguanidine, 2-tert-butyl-1,1,3, 3-tetramethylguanidine, 1,2,3-tricyclohexylguanidine, 1,5, 7-triazabicyclo[4.4.0]dec-5-ene (TBD), 7-methyl-1,5,7-triazabicyclo[4.4.0]dec-5-ene (MTBD), 7-ethyl-1,5,7-triazabicyclo[4.4.0]dec-5-ene, 7-n-propyl-1,5,7-triazabicyclo[4.4.0]dec-5-ene, 7-isopropyl-1,5,7-triazabicyclo[4.4.0]dec-5-ene, 7-n-butyl-1,5,7-triazabicyclo[4.4.0]dec-5-ene, 7-isobutyl-1,5,7-triazabicyclo[4.4.0]dec-5-ene, 7-tert-butyl-1,5,7-triazabicyclo[4.4.0]dec-5-ene, 7-cyclohexyl-1,5,7-triazabicyclo[4.4.0]dec-5-ene, 7-n-octyl-1,5,7-triazabicyclo[4.4.0]dec-5-ene, 7-2-ethylhexyl-1,5, 7-triazabicyclo[4.4.0]dec-5-ene, and 7-decyl-1,5,7-triazabicyclo[4.4.0]dec-5-ene.

In certain embodiments, the nitrogen-containing base is a tetraalkyl ammonium hydroxide. For instance, each alkyl moiety in the tetraalkyl ammonium hydroxide may be independently $C_1$ to $C_6$ alkyl.

In certain embodiments, the nitrogen-containing base is a sterically hindered primary amine, a sterically hindered secondary amine, a sterically hindered tertiary amine, a morpholine compound, an imidazole compound, a pyridine compound, a triamine compound, or an amino-containing ether compound.

In certain embodiments, the phenolic compound is phenol, an alkyl phenol, or an arylalkyl phenol. In one embodiment, the phenolic compound is a para-$C_1$-$C_{24}$ alkyl phenol, such as a para-tert-$C_4$-$C_{12}$ alkyl phenol. In one embodiment, the phenolic compound is benzyl phenol or cumyl phenol.

In certain embodiments, the aldehyde is formaldehyde or paraformaldehyde.

In certain embodiments, the molar ratio of the phenolic compound to the aldehyde ranges from about 1:1.5 to about 1.5:1, and the molar ratio of the phenolic compound to the nitrogen-containing base ranges from about 200:1 to about 20:1.

In certain embodiments, the reaction is carried out in the presence of an organic solvent. In one embodiment, the reaction is carried out in a highly concentrated reaction system, wherein the mass ratio of the phenolic compound to the organic solvent is no less than 0.25:1.

In certain embodiments, the reaction is carried out under reflux conditions. In certain other embodiments, the aldehyde is paraformaldehyde and the reaction is carried out without reflux.

In certain embodiments, the process further comprises heating the reaction mixture at an elevated temperature of 140° C. to 180° C. for a time period of 4 hours or longer to remove water from the reaction mixture.

In certain embodiments, the process is carried out in a one-step reaction and does not include a recrystallization step. In one embodiment, the process further comprises filtrating the reaction product and drying the filtrated reaction product, thereby producing a calixarene compound containing at least 95% calix[8]arene. In one embodiment, the process further comprises washing the reaction product with an organic solvent to remove free phenolic monomers. The process may further comprise filtrating the washed reaction product and drying the filtrated reaction product, thereby producing a calixarene compound with a free phenolic monomer content of about 0.5% or lower.

Embodiments of the invention also include a phenolic oligomer composition prepared by the process described in this aspect of the invention and in any of the above embodiments of this aspect of the invention.

Another aspect of the invention relates to a process for a high-yield, high solid-content production of a calixarene compound. The process comprises reacting a phenolic compound, an aldehyde, and a base catalyst in the presence of an organic solvent, in a highly concentrated reaction system. The mass ratio of the phenolic compound to the organic solvent in the reaction system is no less than 0.25:1. The process produces a calixarene-containing product having at least 50% solids.

In certain embodiments, the nitrogen-containing base is a sterically hindered amine or a tetraalkyl ammonium hydroxide.

In certain embodiments, the organic solvent is an aromatic hydrocarbon or a mixture containing thereof. In one embodiment, the aromatic hydrocarbon contains 7 to 12 carbon atoms.

In certain embodiments, the organic solvent is a straight-chain $C_{11}$ to $C_{20}$ hydrocarbon or a mixture containing thereof.

In certain embodiments, the organic solvent is an ether or a mixture containing thereof. In one embodiment, the ether is diphenyl ether, diethylene glycol dimethyl ether, or diethylene glycol dibutyl ether. In one embodiment, the organic solvent is a mixture of diphenyl ether with xylene and/or ethyl acetate.

In certain embodiments, the mass ratio of the phenolic compound and the organic solvent is no less than 1:1. In one embodiment, the mass ratio of the phenolic compound and the organic solvent is no less than 1.25:1.

In certain embodiments, the phenolic compound is phenol, an alkyl phenol, or an arylalkyl phenol. In one embodiment, the phenolic compound is a para-tert-$C_4$-$C_8$ alkyl phenol. In one embodiment, the phenolic compound is benzyl phenol or cumyl phenol.

In certain embodiments, the aldehyde is formaldehyde or paraformaldehyde.

Embodiments of the invention also include a phenolic oligomer composition prepared by the process described in this aspect of the invention and any of the above embodiments of this aspect of the invention.

Another aspect of the invention relates to a process for the selective synthesis of a calix[8]arene compound. The process comprises reacting a phenolic compound, an aldehyde, and a nitrogen-containing base as a catalyst, in the presence of an organic solvent. The process further comprises heating the reaction mixture at an elevated temperature of about 140° C. to about 180° C. for a time period of 4 hours or longer, to remove water from the reaction mixture and selectively produce a calixarene compound containing at least 70% calix[8]arene.

In certain embodiments, the heating step at the water removal stage is carried out over a time period of 6 hours or longer to selectively produce a calixarene compound containing at least 90% calix[8]arene. In one embodiment, the heating step at the water removal stage is carried out over a time period of 6 hours or longer to selectively produce a calixarene compound containing at least 92% calix[8]arene.

In certain embodiments, the elevated temperature at the water removal stage ranges from about 140° C. to about 150° C.

In certain embodiments, the reacting step is carried out under reflux conditions. In certain other embodiments, the aldehyde is paraformaldehyde and the reaction is carried out without reflux.

In certain embodiments, the phenolic compound is phenol, an alkyl phenol, or an arylalkyl phenol. In one embodiment, the phenolic compound is a para-tert-$C_4$-$C_5$ alkyl phenol. In one embodiment, the phenolic compound is benzyl phenol or cumyl phenol.

In certain embodiments, the aldehyde is formaldehyde or paraformaldehyde.

Embodiments of the invention also include a phenolic oligomer composition prepared by the process described in this aspect of the invention and in any of the above embodiments of this aspect of the invention.

Yet another aspect of the invention relates to a process for a one-step, selective synthesis of a high-purity calix[8]arene compound. The process comprises reacting, in a one-step process, a phenolic compound and an aldehyde in the presence of a base catalyst to form a high-purity calix[8]arene compound, without carrying out a recrystallization step.

In certain embodiments, the process further comprises filtrating the reaction product and drying the filtrated reaction product, thereby producing a calix[8]arene compound with a purity of about 95% or higher. In one embodiment, the process further comprises filtrating the reaction product and drying the filtrated reaction product, thereby producing a calix[8]arene compound with a purity of about 98% or higher.

In certain embodiments, the phenolic compound is phenol, an alkyl phenol, or an arylalkyl phenol. In one embodiment, the phenolic compound is a para-tert-$C_4$-$C_8$ alkyl phenol. In one embodiment, the phenolic compound is benzyl phenol or cumyl phenol.

In certain embodiments, the aldehyde is formaldehyde or paraformaldehyde.

Embodiments of the invention also include a phenolic oligomer composition prepared by the process described in this aspect of the invention and in any of the above embodiments of this aspect of the invention.

Another aspect of the invention relates to a process for the selective synthesis of a calix[8]arene compound with a low free phenolic monomer content. The process comprises the steps of reacting a phenolic compound and an aldehyde in the presence of a base catalyst, and washing the reaction product to remove free phenolic compound monomers, to produce a calix[8]arene compound with a free phenolic monomer content of about 0.5% or lower. The process does not include a recrystallization step.

In certain embodiments, the free phenolic monomer content is about 0.1% or lower.

In certain embodiments, the process further comprises filtrating the washed reaction product and drying the filtrated reaction product, thereby producing a high-purity calix[8]arene compound with a purity of about 95% or higher.

In certain embodiments, the phenolic compound is phenol, an alkyl phenol, or an arylalkyl phenol. In one embodiment, the phenolic compound is a para-tert-$C_4$-$C_5$ alkyl phenol. In one embodiment, the phenolic compound is benzyl phenol or cumyl phenol.

In certain embodiments, the aldehyde is formaldehyde or paraformaldehyde.

Embodiments of the invention also include a phenolic oligomer composition prepared by the process described in this aspect of the invention and in any of the above embodiments of this aspect of the invention.

Another aspect of the invention relates to a calixarene compound comprising n units of formula (A-1):

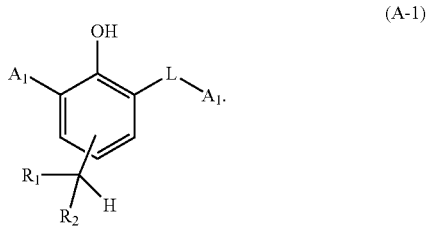

In formula (A-1), each of $R_1$ and $R_2$ is independently linear, branched, or cyclic $C_1$-$C_{30}$ alkyl, aryl, alkylaryl, or arylalkyl. Each L is independently selected from the group consisting of —$CH_2$—, —C(O)—, —CH($R_3$)—, —$(CH_2)_{n'}$-O—$(CH_2)_{n'}$—, —C($R_3$)$_2$—. Each $R_3$ is independently a $C_1$-$C_6$ alkyl. Integer n ranges from 2-20. Each n' is independently an integer from 1-2. Each $A_1$ represents a direct covalent bond to an adjacent unit of formula (A-1) such that there is one L group between adjacent units, whereby the total units in the calixarene compound form a ring. In one embodiment, each of $R_1$ and $R_2$ is independently linear $C_1$-$C_6$ alkyl. For instance, each $R_1$ is methyl, and each $R_2$ is methyl, ethyl, propyl, or hexyl. In one embodiment, the integer n is 8. In one embodiment, the calixarene compound has the structure of

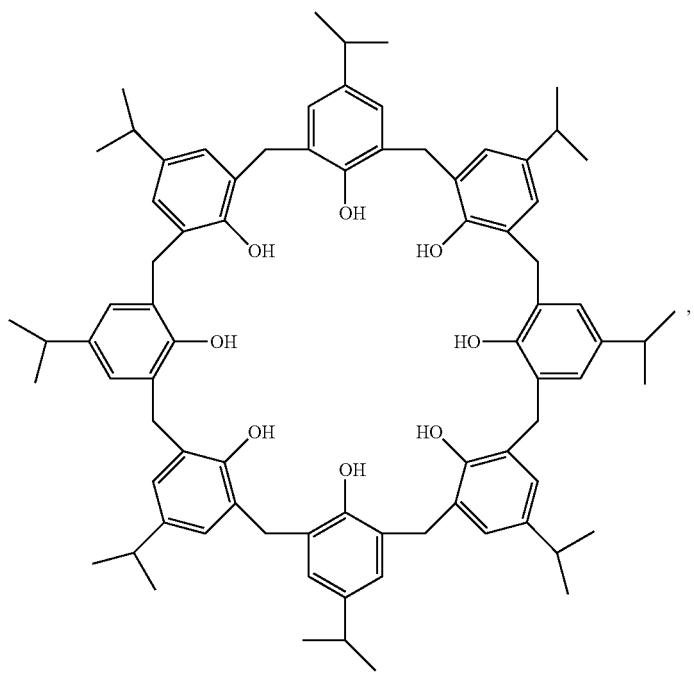

-continued
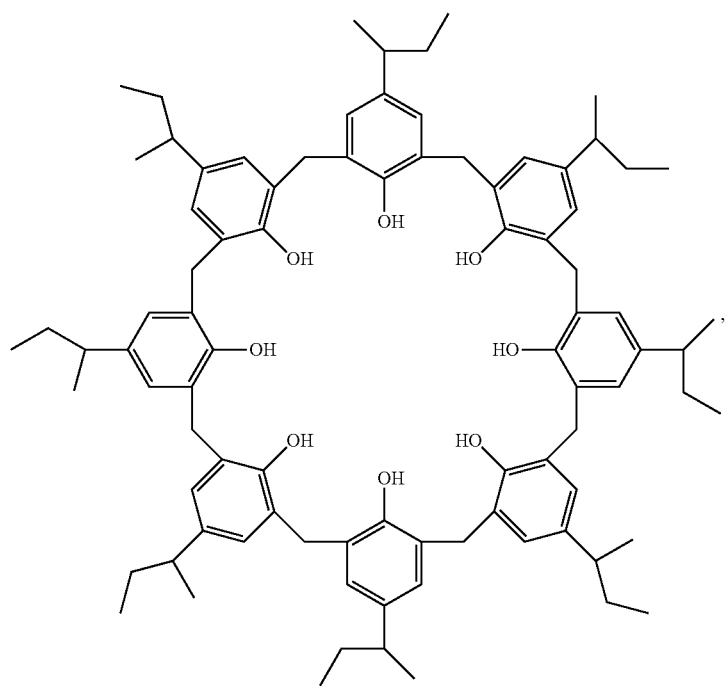
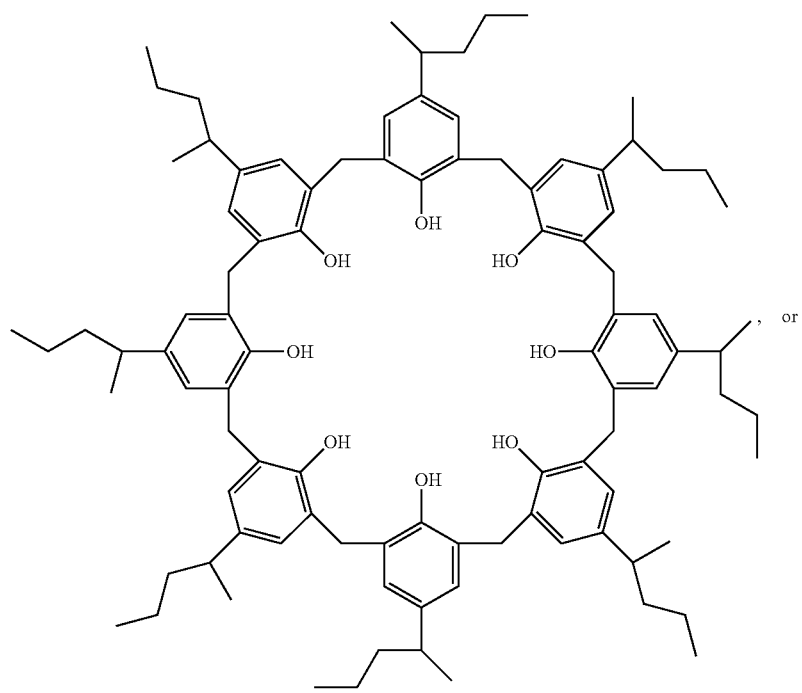

-continued

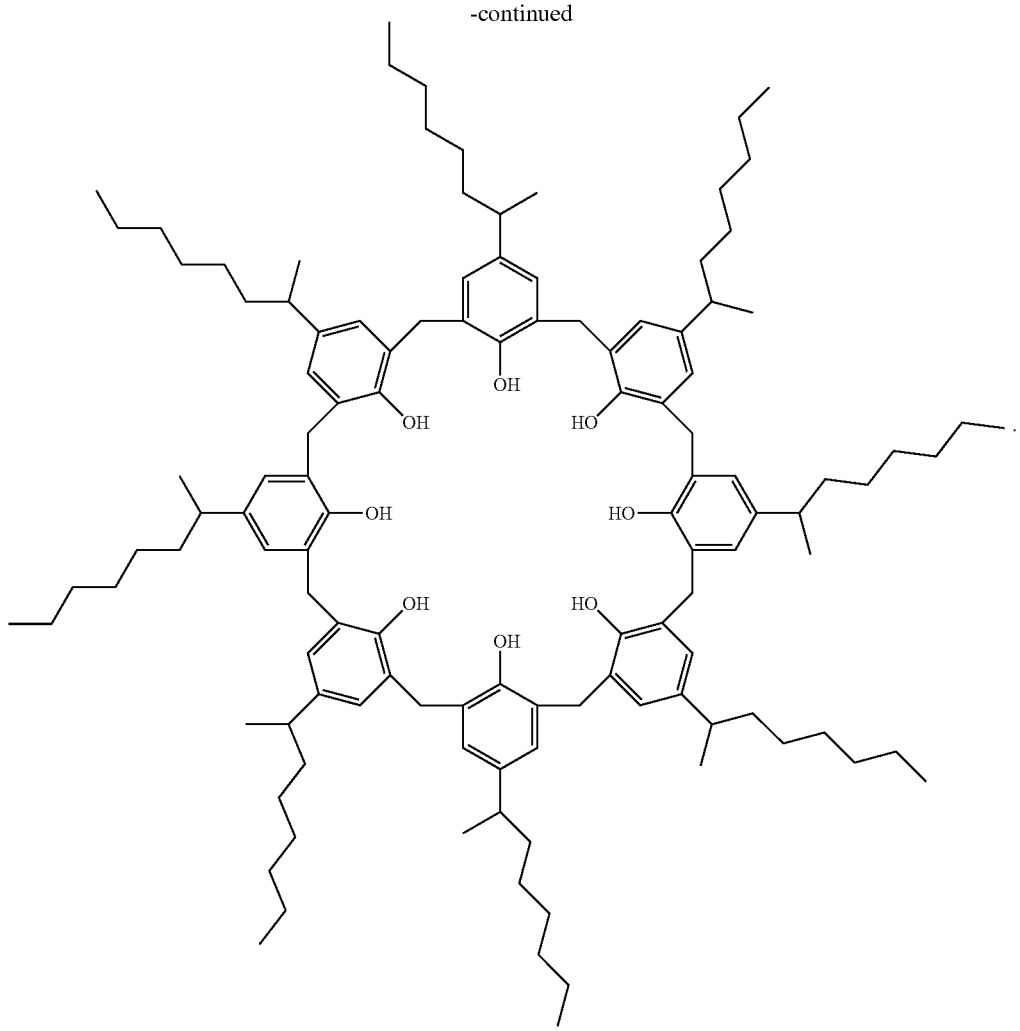

DETAILED DESCRIPTION OF THE INVENTION

Figure 1:
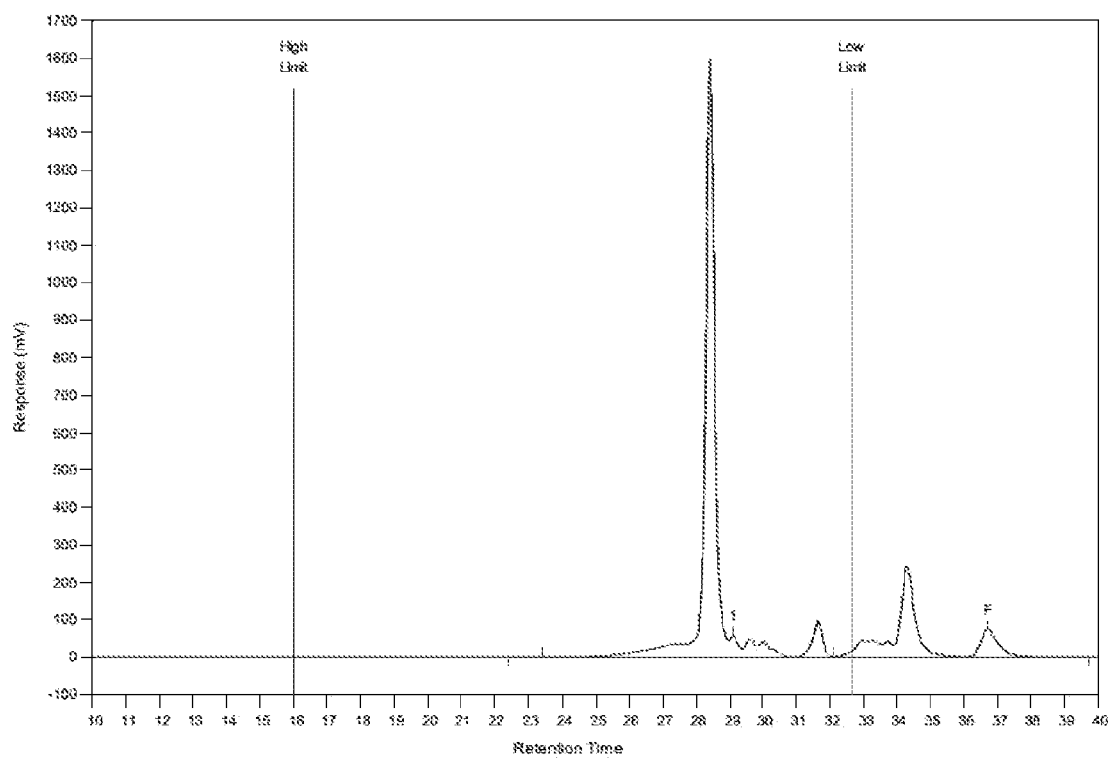
FIG. 1 shows the GPC results of the final reaction mass prepared from Example 1.

One aspect of the invention relates to a process for preparing a calixarene compound, comprising reacting a phenolic compound and an aldehyde in the presence of at least one nitrogen-containing base as a catalyst to form a calixarene compound.

The phenolic compound may be a monohydric, dihydric, or polyhydric phenol, or its derivative, with or without substituent(s) on the benzene ring of the phenolic compound. Suitable monohydric, dihydric, or polyhydric phenols include, but are not limited to, phenol; dihydric-phenols such as resorcinol, catechol, and hydroquinone; trihydric-phenols such as pyrogallol, hydroxy quinol, or phloroglucinol; dihydroxybiphenol such as 4,4'-biphenol; alkylidenebisphenols (the alkylidene group can have 1-12 carbon atoms) such as 4,4'-methylenediphenol (bisphenol F), and 4,4'-isopropylidenediphenol (bisphenol A); trihydroxybiphenol; and thiobisphenols. Exemplary monohydric, dihydric, or polyhydric phenols include phenol, resorcinol, and pyrogallol. In one embodiment, the phenolic compound is phenol.

Suitable phenolic compounds also include a monoether derivative or diether derivative of the monohydric, dihydric, or polyhydric phenols. The ether derivative of the monohydric, dihydric, or polyhydric phenols may be an alkyl ether, an aryl ether, or an alkyl aryl ether, which may be optionally substituted with a hydroxy, alkoxy, alkylene oxide, or acryloxy group. For instance, the ether derivative may be a monoalkyl ether, dialkyl ether, monoglycidyl ether, diglycidyl ether, or benzyloxy ether group, or mixtures thereof.

The benzene ring of the monohydric, dihydric, or polyhydric phenol, or its derivative can be substituted in the ortho, meta, and/or para positions by one or more linear, branched, or cyclic $C_1$-$C_{30}$ alkyl, or halogen (F, Cl, or Br). The one or more substituents on the benzene ring of the phenolic compound may be $C_1$-$C_{30}$ alkyl, aryl, alkylaryl, or arylalkyl. For example, the benzene ring of the phenolic compound can be substituted by $C_1$-$C_{24}$ alkyl, $C_1$-$C_{16}$ alkyl, $C_4$-$C_{16}$ alkyl, or $C_4$-$C_{12}$ alkyl (such as tert-$C_4$-$C_{12}$ alkyl). Suitable substituents on the benzene ring also include aryl, such as phenyl; $C_1$-$C_{30}$ arylalkyl (such as benzyl or cumyl); or $C_1$-$C_3$ alkylaryl.

In certain embodiments, the phenolic compound is phenol, resorcinol, pyrogallol, 4,4'-biphenol, 4,4'-methylenediphenol, or 4,4'-isopropylidenediphenol, each having the benzene ring being substituted with H or $C_1$-$C_{24}$ alkyl (e.g., $C_4$ to $C_{12}$ alkyl).

In certain embodiments, the phenolic compound is a mono- or di-ether (e.g., a $C_1$-$C_6$ alkyl ether or glycidyl ether) of phenol, resorcinol, pyrogallol, 4,4'-biphenol, 4,4'-methylenediphenol, or 4,4'-isopropylidenediphenol, each having the benzene ring being substituted with H or $C_1$-$C_{24}$ alkyl (e.g., $C_4$ to $C_{12}$ alkyl).

When the phenolic compound is a substituted phenol, the phenolic compound typically contains one substituent at the para position. In one embodiment, the phenolic compound is phenol, an arylalkyl phenol (such as para-benzylphenol or para-cumylphenol), or an alkylphenol, particularly a para-$C_1$-$C_{24}$ (linear, branched, or cyclic) alkylphenol, such as para-methylphenol, para-ethylphenol, para-isopropylphenol, para-tert-butylphenol (PTBP), para-sec-butylphenol, para-tert-amylphenol (PTAP), para-tert-hexylphenol, para-cyclohexylphenol, para-sec-octylphenol, para-tert-octylphenol (PTOP), para-isooctylphenol, para-decylphenol, para-dodecylphenol, para-tetradecyl phenol, para-octadecylphenol, para-nonylphenol, para-pentadecylphenol, para-cetylphenol, para-adamantylphenol, and para-(2-isopropyl-5-methylcyclohexyl)phenol. Typical alkyl phenols include para-tert-$C_4$-$C_{12}$ alkylphenols, such as para-tert-$C_4$-$C_8$ alkylphenols.

Suitable phenolic compounds also include those phenols described in Gutsche, "Chapter 1. Synthesis of Calixarenes and thiacalixarenes," *Calixarenes* 2001 (Edited by M.-Z. Asfari et. al., Kluwer Academic Publishers, 2001), pages 1-25, which is incorporated herein by reference in its entirety, to the extent not inconsistent with the subject matter of this disclosure.

In certain embodiments, the process is used for preparing a calixarene compound with a high solid-content, or for the selective synthesis of a calix[8]arene compound. Exemplary phenolic compounds are phenol, a $C_4$ to $C_8$ alkyl phenol (linear, branched, or cyclic) (e.g., a para-tert-$C_4$-$C_8$ alkylphenol), and an arylalkyl phenol (such as benzyl phenol or cumyl phenol).

Any aldehyde known in the art for preparing a phenolic resin (linear or cyclic) is suitable in this process. Exemplary aldehydes include formaldehyde, methyl formcel (i.e., formaldehyde in methanol), butyl formcel, acetaldehyde, propionaldehyde, butyraldehyde, crotonaldehyde, valeraldehyde, caproaldehyde, heptaldehyde, benzaldehyde, as well as compounds that decompose to aldehyde such as paraformaldehyde, trioxane, furfural (e.g., furfural or hydroxymethylfurfural), hexamethylenetriamine, aldol, p-hydroxybutyraldehyde, and acetals, and mixtures thereof. A typical aldehyde used is formaldehyde or paraformaldehyde.

To prepare a calixarene compound, the molar ratio of the total amount of the phenolic compounds to the total amount of the aldehyde added to the reaction typically ranges from about 0.5:1 to about 2:1, for instance, from about 1:1.5 to about 1.5:1, from about 1:1.3 to about 1.3:1, or from about 1:1.15 to about 1:1.

The term "calixarene" generally refers to a variety of derivatives that may have one or more substituent groups on the hydrocarbons of cyclo{oligo[(1,3-phenylene)methylene]}. The term "calixarene" also generally encompasses the cyclic structure formed by not only a monohydric phenol, such as phenol or alkylphenol, but also a dihydric or polyhydric phenol, or a derivative thereof. The calixarenes may contain a substituent on the benzene ring of calixarenes. Exemplary cyclic structures of the calixarenes are those formed by phenol, resorcinol, or pyrogallol.

A typical calixarene compound based on phenols has a structure of Formula (A'):

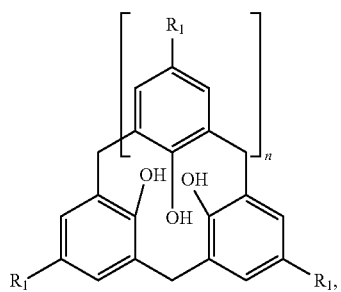

A typical calixarene compound based on resorcinols has a structure of Formula (B-1') or (B-2'):

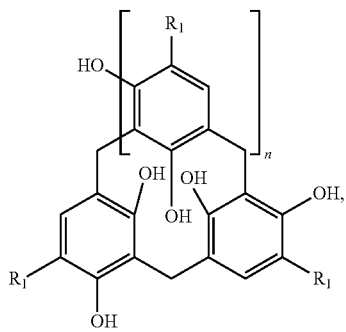

or

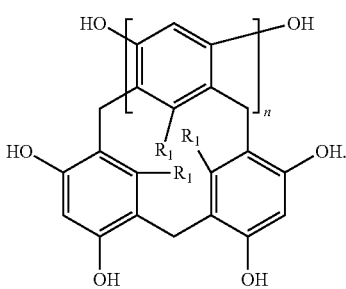

A typical calixarene compound based on pyrogallols has a structure of Formula (C'):

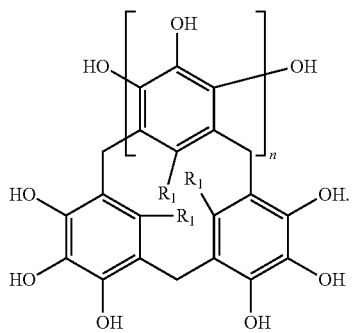

In Formulas (A'), (B-1'), (B-2'), and (C'), the substituent group $R_1$ on the benzene ring of the calixarene compound depends on the phenolic compounds used in the process to prepare the calixarene compound. For instance, $R_1$ may be H, $C_1$-$C_{30}$ alkyl, aryl, alkylaryl, or arylalkyl. All above descriptions in the context of the substituents on the benzene ring of the phenolic compound are applicable to the definition of $R_1$. The number of units of phenolic monomers of the calixarene (e.g., n in Formulas (A'), (B-1'), (B-2'), and (C')) may be 2 to 100, for instance, 2 to 50, 2 to 30, 2 to 20, 2 to 10, 2 to 8, 2 to 6, or 2 to 4, resulting in a molecular weight typically ranging from about 500 to about 25,000 daltons, from about 500 to about 10,000 daltons, from about 500 to about 5,000 daltons, from about 1,000 to about 5,000 daltons, from about 500 to about 3,000 daltons, or from about 500 to about 1,000 daltons.

In certain embodiments, the calixarene compound comprises n units of phenolic monomers of Formula (A):

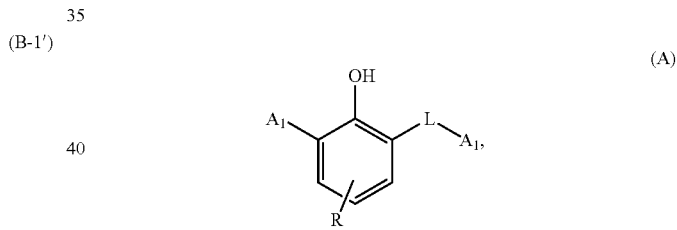

in which the substituent group R on the benzene ring of the calixarene compound depends on the phenolic compounds used in the process to prepare the calixarene compound. For instance, R may be H, $C_1$-$C_{30}$ alkyl, aryl, alkylaryl, or arylalkyl. All above descriptions in the context of the substituents on the benzene ring of the phenolic compound are applicable to the definition of R. Each $A_1$ represents a direct covalent bond to an adjacent unit of Formula (A) such that there is one L group between adjacent units, whereby the total units in the calixarene compound form a ring. The L group depends on the aldehyde used in the process to prepare the calixarene compound. For instance, each L may be independently selected from the group consisting of —$CH_2$—, —C(O)—, —CH($R_3$)—, —$(CH_2)_n$'-O—$(CH_2)_n$'—, and —C($R_3$)$_2$—; each $R_3$ may be independently a $C_1$-$C_6$ alkyl; and each n' may be independently an integer from 1 to 2. Typically, when formaldehyde is used, L may be —$CH_2$— or —$CH_2$—O—$CH_2$—.

Typically, in the case of a monohydric phenol with a substituent group being used to form the calixarene compound, if the substituent group is at the para position to the hydroxyl group of the phenolic compound, the resulting alkylene bridge (e.g., methylene bridge if formaldehyde is used) extends in the ortho positions to the hydroxyl group of the phenolic compound (see, e.g., Formula (A')). If the substituent group is at the ortho position to the hydroxyl group of the phenolic compound, the resulting alkylene bridge can extend in the para position to the hydroxyl group of the phenolic compound and the other substituted ortho position to the hydroxyl group of the phenolic compound. In the case of a dihydric phenol being used to form the phenolic resin, the location of the alkylene bridge (e.g., methylene bridge if formaldehyde is used) can also vary depending on the relative position of the hydroxyl groups and the substituent groups. For instance, two possible connections of the phenolic units are shown in Formula (B-1') and (B-2') above. In the case of a trihydric phenol being used to form the phenolic resin, the location of the alkylene bridge (e.g., methylene bridge if formaldehyde is used) can also vary depending on the relative positions of the hydroxyl groups and the substituent group. For instance, a possible connection of the phenolic units is shown in Formula (C') above.

The number of units of phenolic monomers in the calixarene compound (e.g., n in the context of Formula (A)) may be 2 to 100, for instance, 2 to 50, 2 to 30, 2 to 20, 2 to 10, 2 to 8, 2 to 6, or 2 to 4, resulting in a molecular weight typically ranging from about 500 to about 25,000 daltons, from about 500 to about 10,000 daltons, from about 500 to about 5,000 daltons, from about 1,000 to about 5,000 daltons, from about 500 to about 3,000 daltons, or from about 500 to about 1,000 daltons.

The term "calix[n]arene" typically specifies the number of units of phenolic monomers in the calixarene compound prepared. For instance, a calix[8]arene compound is a calixarene compound having 8 units of phenolic monomers.

An exemplary calix[8]arene structure is shown as below:

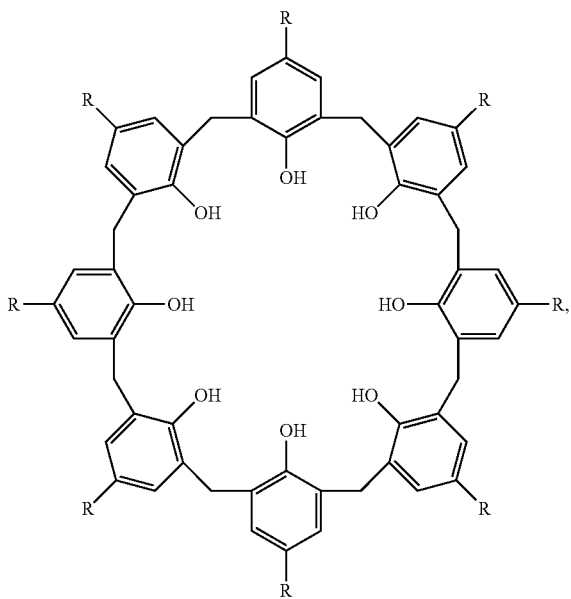

in which the phenolic compound used in the process has a substituent group, R, at the para position to the hydroxyl group of the phenolic compound and the aldehyde used in the process is formaldehyde.

The calixarene compound may be prepared from one or more phenolic compounds reacting with one or more aldehydes forming an oligomer of phenolic monomers. The resulting calixarene compound may be a homopolymer of the same phenolic monomer, or a copolymer containing different units of phenolic monomers, e.g., when two or more different phenolic compounds were reacted with an aldehyde.

In certain embodiments, the phenolic units in the calixarene compound can be resulting from the same or different phenolic compounds. The benzene ring of each phenolic unit can be independently substituted with a same or different substituent group R. For instance, the phenolic units in the calixarene compound are the same or different phenols, and the benzene ring of each phenol is independently substituted with H or $C_1$ to $C_{20}$ alkyl (e.g., $C_4$ to $C_{12}$ alkyl).

In certain embodiments, the calixarene compound comprises n units of phenolic monomers of Formula (A-1):

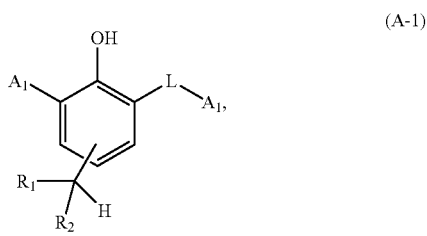

(A-1)

in which each of $R_1$ and $R_2$ is independently linear, branched, or cyclic $C_1$-$C_{30}$ alkyl, aryl, alkylaryl, or arylalkyl. For instance, each of $R_1$ and $R_2$ may be independently $C_1$-$C_{12}$ alkyl (linear, branched, or cyclic), or $C_1$-$C_6$ alkyl (linear). In one embodiment, each $R_1$ is methyl, and each $R_2$ is methyl, ethyl, propyl, or hexyl.

Each $A_1$ represents a direct covalent bond to an adjacent unit of Formula (A-1) such that there is one L group between adjacent units, whereby the total units in the calixarene compound form a ring. The L group depends on the aldehyde used in the process to prepare the calixarene compound. For instance, each L may be independently selected from the group consisting of —$CH_2$—, —C(O)—, —CH($R_3$)—, —($CH_2$)$_n$'—O—($CH_2$)$_n$'—, and —C($R_3$)$_2$—; each $R_3$ may be independently a $C_1$-$C_6$ alkyl; and each n' may be independently an integer from 1 to 2. Typically, when formaldehyde is used, L is —$CH_2$— or —$CH_2$—O—$CH_2$—.

The total number of units in the calixarene compound of Formula (A-1), i.e., n, is an integer that typically ranges from 2-20. In one embodiment, n is from 4-10, for instance, 4, 5, 6, 7, 8, 9, or 10.

In one embodiment, the substituent group

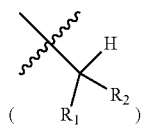

on the calixarene compound of Formula (A-1) is at the para position to the hydroxyl group.

The calixarene compounds described above can exist in one or more stereoisomeric forms, depending on the reaction conditions and/or the chirality of the starting phenolic compounds. For instance, when using a phenolic compound with a chiral center

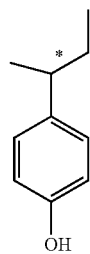

(* indicates the chiral center), the resulting calixarene compound may contain stereoisomeric forms, e.g.,

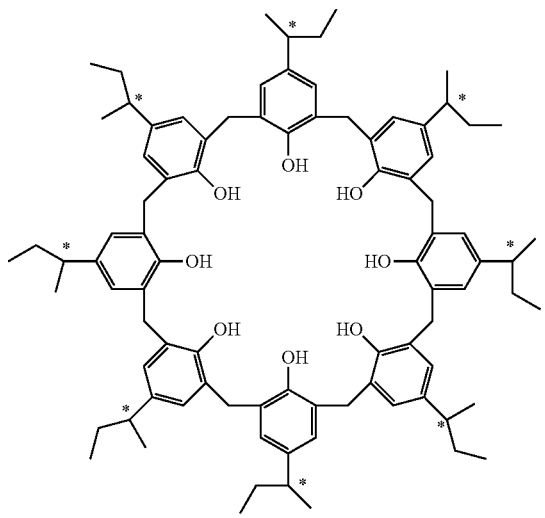 [SMILES: CCC(C)c1cc2c(O)c(c1)Cc1cc(C(C)CC)cc(c1O)Cc1cc(C(C)CC)cc(c1O)Cc1cc(C(C)CC)cc(c1O)Cc1cc(C(C)CC)cc(c1O)Cc1cc(C(C)CC)cc(c1O)Cc1cc(C(C)CC)cc(c1O)Cc1cc(C(C)CC)cc(c1O)C2]

(* indicates the chiral center). However, the calixarene compounds may be a mixture in which the stereoisomeric forms may not be easy to be separated. When the starting phenolic compound does not contain a chiral center (for instance, an isopropylphenol), the resulting calixarene compounds would not form different diastereomers.

Exemplary calixarene compounds for the calixarene compound of Formula (A-1) have the structures of

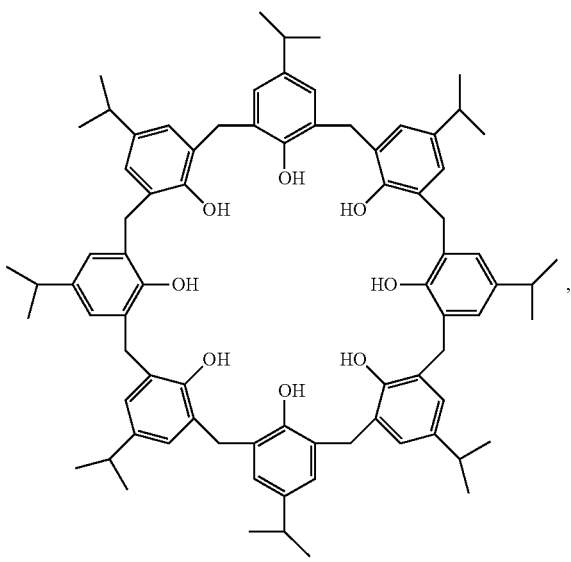

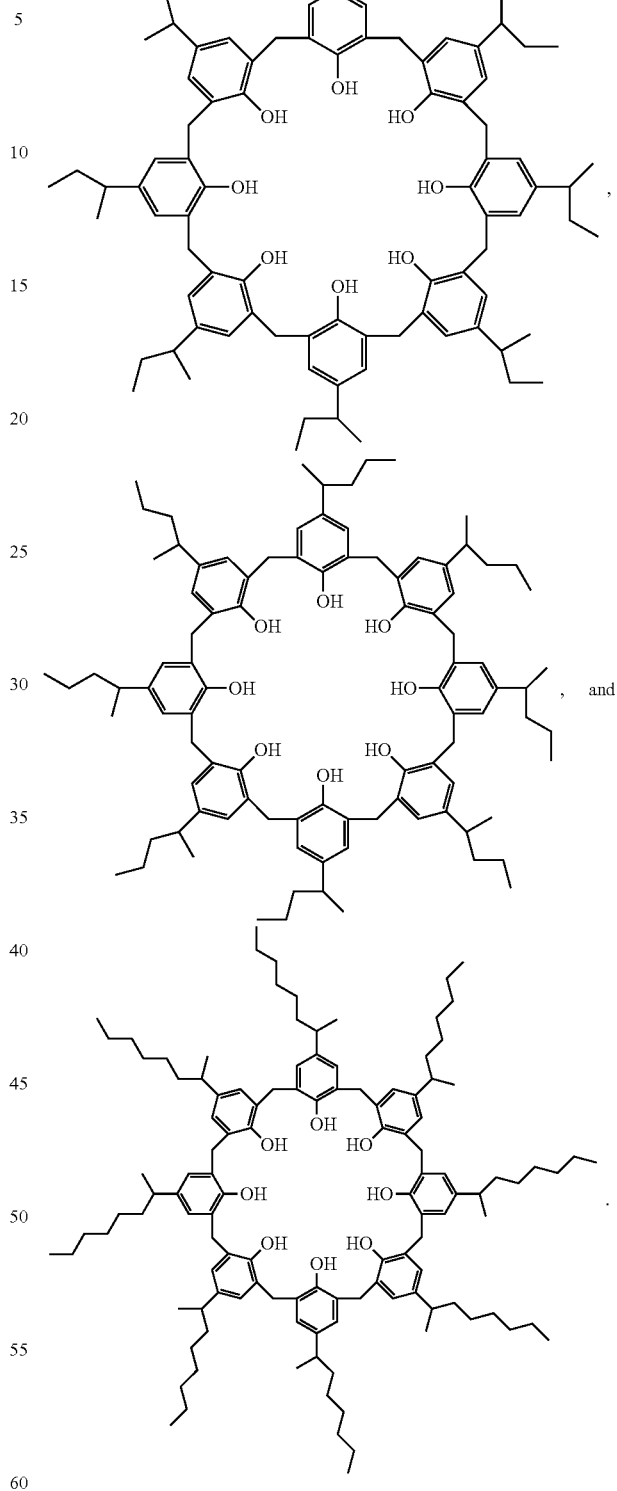

, and

Catalyst

A nitrogen-containing base, such as a sterically hindered amine, has a weaker basicity than most alkaline base catalysts, such as sodium hydroxide or potassium hydroxide, the catalysts conventionally used for the synthesis of calixarene compounds, including a calix[8]arene compound. Thus, the conventional alkaline base catalysts convert the formaldehyde faster during the condensation reaction, following a kinetic route different than the kinetic route when using a nitrogen-containing base, such as a sterically hindered amine, as the catalyst. Because of this, these conventional alkaline base catalysts typically produce significant amounts of other ring-sized calixarenes (e.g., about 13% of calix[4]arenes and calix[6]arenes). The nitrogen-containing base catalysts discussed herein, however, allow for a slower build-up of desirable linear precursors for the cyclic compounds (calixarenes) formation, thereby eventually resulting in a higher selectivity toward calix[8]arenes. Because of their weaker basicity than conventional alkaline base catalysts, the nitrogen-containing base catalysts discussed herein also display milder reaction conditions.

The nitrogen-containing base used herein typically has a relatively high boiling point. For instance, the nitrogen-containing base may have a boiling point of no less than about 80° C., for instance, no less than about 90° C., no less than about 100° C., no less than about 110° C., no less than about 120° C., no less than about 130° C., or no less than about 140° C. Because of this high boiling point, the nitrogen-containing base is usually not removed during the reaction of the phenolic compounds and the aldehyde, under the reflux and/or distillation conditions.

In addition, when using the nitrogen-containing base as a catalyst for the reaction between the phenolic compound and aldehyde, the weak acid phenol can protonate the nitrogen atom in the nitrogen-containing base. This prevents, or substantially inhibits, the nitrogen-containing base from being removed during the reaction of the phenolic compounds and aldehyde, under the reflux and/or distillation conditions.

As defined herein, a nitrogen-containing base may generally include a sterically hindered amine (e.g., a sterically hindered primary amine, a sterically hindered secondary amine, and a sterically hindered tertiary amine) and a sterically hindered quaternary ammonium hydroxide, such as a tetraalkyl ammonium hydroxide.

Suitable sterically hindered amine compounds include an amidine compound having the formula of

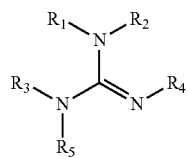

(I)

and a guanidine compound having the formula of

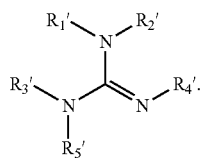

(II)

For the amidine compounds having the formula of

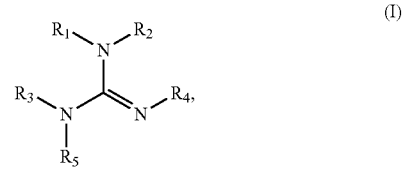

(I)

$R_1$, $R_2$, $R_3$, and $R_4$ are each independently H, alkyl, cycloalkyl, heterocycloalkyl, aryl, or heteroaryl; or any two or more of $R_1$, $R_2$, $R_3$, and $R_4$ can be bonded together to form a five- to nine-membered ring structure. For instance, $R_1$, $R_2$, $R_3$, and $R_4$ are each independently H, $C_1$ to $C_8$ alkyl, $C_5$ to $C_7$ cycloalkyl, $C_5$ to $C_7$ heterocycloalkyl, phenyl, or $C_5$ to $C_7$ heteroaryl; or any two or more of $R_1$, $R_2$, $R_3$, and $R_4$ can be bonded together to form a five-, six-, or seven-membered ring structure.

Suitable amidine compounds include 1,8-diazabicyclo[5.4.0]undec-7-ene (DBU), 1,5-diazabicyclo[4.3.0]non-5-ene (DBN), 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, and 1-ethyl-2-isopropyl-1,4,5,6-tetrahydropyrimidine. Exemplary amidine compounds used as the catalyst include

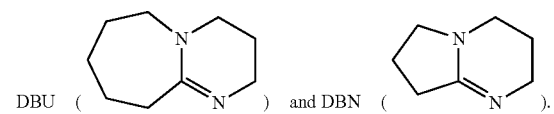 [SMILES: "DBU" ; C1CCC2=NCCCN2CC1 ; C1CN=C2CCCN2C1]

For the guanidine compounds having the formula of

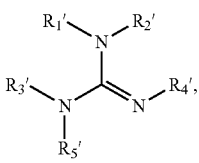

(II)

$R_1'$, $R_2'$, $R_3'$, $R_4'$, and $R_5'$ are each independently H, alkyl, cycloalkyl, heterocycloalkyl, aryl, or heteroaryl; or any two or more of $R_1'$, $R_2'$, $R_3'$, $R_4'$, and $R_5'$ can be bonded together to form a five- to nine-membered ring structure. For instance, $R_1'$, $R_2'$, $R_3'$, $R_4'$, and $R_5'$ are each independently H, $C_1$ to $C_5$ alkyl, $C_5$ to $C_7$ cycloalkyl, $C_5$ to $C_7$ heterocycloalkyl, phenyl, or $C_5$ to $C_7$ heteroaryl; or any two or more of $R_1'$, $R_2'$, $R_3'$, $R_4'$, and $R_5'$ can be bonded together to form a five-, six-, or seven-membered ring structure.

Suitable guanidine compounds include 1-methylguanidine, 1-n-butylguanidine, 1,1-dimethylguanidine, 1,1-diethylguanidine, 1,1,2-trimethylguanidine, 1,2,3-trimethylguanidine, 1,3-diphenylguanidine, 1,1,2,3,3-pentamethylguanidine, 2-ethyl-1,1,3,3-tetramethylguanidine, 1,1,3,3-tetramethyl-2-n-propylguanidine, 1,1,3,3-tetramethyl-2-isopropylguanidine, 2-n-butyl-1,1,3,3-tetramethylguanidine, 2-tert-butyl-1,1,3,3-tetramethylguanidine, 1,2,3-tricyclohexylguanidine, 1,5, 7-triazabicyclo[4.4.0]dec-5-ene (TBD), 7-methyl-1,5,7-triazabicyclo[4.4.0]dec-5-ene (MTBD), 7-ethyl-1,5,7-triazabicyclo[4.4.0]dec-5-ene, 7-n-propyl-1,5,7-triazabicyclo[4.4.0]dec-5-ene, 7-isopropyl-1,5,7-triazabicyclo[4.4.0]dec-5-ene, 7-n-butyl-1,5,7-triazabicyclo[4.4.0]dec-5-ene, 7-isobutyl-1,5,7-triazabicyclo[4.4.0]dec-5-ene, 7-tert-butyl-1,5,7-triazabicyclo[4.4.0]dec-5-ene, 7-cyclohexyl-1,5,7-triazabicyclo[4.4.0]dec-5-ene, 7-n-octyl-1,5,7-triazabicyclo[4.4.0]dec-5-ene, 7-2-ethylhexyl-1,5,7-triazabicyclo[4.4.0]dec-5-ene, 7-decyl-1,5,7-triazabicyclo[4.4.0]dec-5-ene. Exemplary guanidine compounds used as the catalyst include TBD ( 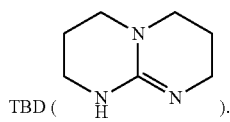 ).

Other suitable nitrogen-containing bases include sterically hindered primary amines (e.g., triphenylmethylamine or 1,1-diethyl-n-propylamine); sterically hindered secondary amines (e.g., dicyclohexylamine, t-butylisopropylamine, di-t-butylamine, cyclohexyl-t-butylamine, di-sec-butylamine, dicyclopentylamine, di-(α-trifluoromethylethyl)amine, or di-(α-phenylethyl)amine)); sterically hindered tertiary amines (e.g., dicyclohexylmethylamine, ethyldiisopropylamine, dimethylcyclohexylamine, dimethylisopropylamine, methylisopropylbenzylamine, methylcyclopentylbenzylamine, isopropyl-sec-butyl-trifluoroethylamine, diethyl-(α-phenylethyl)amine, trialkylenediamine such as triethylenediamine (1,4-diazabicyclo[2.2.2]octane, DABCO), or trialkylamine such as trimethylamine, triethylamine or tri-n-propylamine); morpholine compounds (e.g., morpholine, N-ethylmorpholine, N-methylmorpholine, dimorpholinodimethylether, or dimorpholinodiethylether); imidazole compounds (e.g., imidazole, 2-methylimidazole, n-methylimidazole, or 1,2-dimethylimidazole); pyridine compounds (e.g., pyridine, 4-methylaminopyridine, 2-methylaminopyridine, or 4-dimethylaminopyridine); triamine compounds (e.g., N,N,N',N',N'',N''-pentamethyldiethylenetriamine, N,N,N',N',N'',N''-pentaethyldiethylenetriamine, or N,N,N',N',N'',N''-pentamethyldipropylenetriamine), and amino-containing ether compounds (e.g., bis(dimethylaminoethyl)ether, bis(diethylaminoethyl)ether, or bis(dimethylaminopropyl)ether). Exemplary nitrogen-containing bases from this group include triethylamine ( 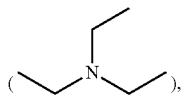 ), ethyldiisopropylamine ( 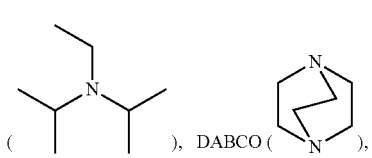 ), DABCO ( 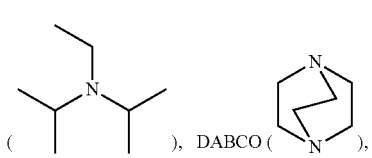 ), imidazole ( 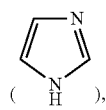 ), 2-methylimidazole ( 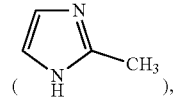 ), pyridine, and 4-dimethylaminopyridine ( 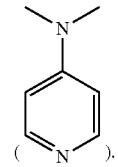 ).

The sterically hindered quaternary ammonium hydroxide typically includes a tetraalkyl ammonium hydroxide. Each alkyl moiety in the tetraalkyl ammonium hydroxide can be independently $C_1$ to $C_6$ alkyl, for instance, $C_1$ to $C_4$ alkyl. Exemplary tetraalkyl ammonium hydroxides used as the catalyst include tetramethyl ammonium hydroxide ( 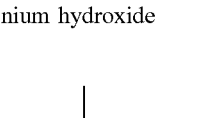 ), tetraethylammonium hydroxide ( 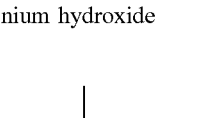 ), tetrapropylammonium hydroxide ( 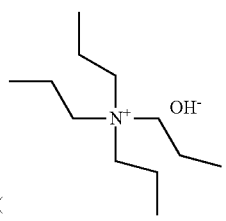 ), and tetrabutylammonium hydroxide ( 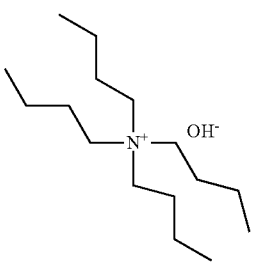 ).

The molar ratio of the total amount of the phenolic compounds to the nitrogen-containing base catalyst added to the reaction typically ranges from about 200:1 to about 20:1, for instance, from about 100:1 to about 40:1, from about 70:1 to about 40:1, or from about 65:1 to about 45:1.

Solvent

The reaction of the phenolic compound and the aldehyde is typically carried out in the presence of an organic solvent. Suitable organic solvents are non-reactive and have low viscosity, including but not limited to, aliphatic solvents including alkanes (such as alkanes having 4 to 24 carbon atoms; e.g., alkanes having 11 to 20 carbon atoms, or having 5 to 16 carbon atoms) and cycloalkanes (such as cycloalkanes having 3 to 24 carbon atoms; e.g., cycloalkanes having 5 to 16 carbon atoms); aromatic solvents (such as alkylbenzenes or naphthalenes; e.g., an aromatic hydrocarbon solvent containing 7 to 12 carbon atoms); ethers including aromatic ethers (such as diphenyl ether) and ethers based on ethylene glycol (such as diethylene glycol dibutyl ether or diethylene glycol dimethyl ether); and mixtures containing thereof.

Exemplary organic solvents include xylene, toluene, benzene, naphthalene, an aromatic 150 fluid (i.e., an aromatic hydrocarbon solvent having a main component ranging from 9 to 12 carbon atoms, such as Solvesso™ 150 fluid or other similar aromatic hydrocarbon solvents marketed under different brands), diphenyl ether, diethylene glycol dimethyl ether, diethylene glycol dibutyl ether, Dowtherm©A (a mixture of diphenylether and biphenyl), nonane, octane, hexadecane, and mixtures containing thereof.

Suitable organic solvents also include those hydrocarbon solvents having a high boiling point, such as a straight-chain $C_{11}$ to $C_{20}$ hydrocarbon having a boiling point ranging from about 250 to about 260° C., and mixtures containing thereof. Such solvents can be obtained from a petroleum middle distillate that contain a paraffin mixture having a distillation range from about 250 to about 260° C. Using high boiling point solvents may also result in a higher yield and higher selectivity toward cyclic compounds (calixarenes) over linear compounds (linear phenolic resins) in the cyclization phase, compared against the organic solvents with a lower boiling point (such as A-150). In one embodiment, tert-octylcalix[8]arenes prepared in hexadecane has an isolated yield of about 15% higher than the isolated yield of tert-octylcalix[8]arenes prepared in A-150, with the reaction reagents/conditions otherwise being the same.

It is believed that the polarity of the organic solvents may be used to adjust the kinetics of the reaction, resulting in different linear precursor formation during the reflux phase or different crystallization behavior during the cyclization phase (or distillation phase), thereby adjusting the selectivity of the resulting calixarene compounds. For instance, the organic solvents with a higher polarity or nucleophilicity (that is, the ability of the solvent to interact with polar transition states in the polycondensation reaction), such as diphenyl ether, may modify the activity of the nitrogen-containing base catalyst in a way to improve the formation of the amount of the desired linear precursor necessary to form the desired calixarene compounds. This could result in a higher yield and higher selectivity toward cyclic compounds (calixarenes) over linear compounds (linear phenolic resins) in the cyclization phase, compared against the organic solvents with a lower polarity or nucleophilicity (such as xylene or A-150). In one embodiment, tert-amylcalix[8]arenes prepared in diphenylether/xylene mixture has an isolated yield of about 5% higher than the isolated yield of tert-amylcalix[8]arenes prepared in A-150, with the reaction reagents/conditions otherwise being the same.

Additionally, when a high boiling point solvent is used, one or more other organic solvents may be added as an azeo-carrier. For instance, when a high-boiling-point solvent, such as diphenyl ether, is used in the reaction, this solvent alone does not form azeotropes with water due to its high boiling point. When water is produced in the reaction system, it is actually released above its boiling point of 100° C. and, thus, would enter the vapor phase causing significant foaming. Adding an azeo-carrier can mitigate this boil-over issue by forming azeotropes with water and constantly removing water from the reaction mass. Exemplary azeo-carrier solvents are xylene and ethyl acetate. An exemplary organic solvent used in the reaction is a mixture of diphenyl ether with xylene and/or ethyl acetate.

Typically, the calixarene compounds formed have poor solubility at room temperature in a typical hydrocarbon solvent, with some exceptions such as para-nonylcalixarenes and para-dodecylcalixarenes which may be liquid at room temperature. Conventionally, solid calixarene compounds are synthesized under high-dilution conditions, meaning that the reaction of the phenolic compound and the aldehyde are typically conducted in a large amount of an organic solvent (e.g., with the solvent concentration of about 80-85 wt %). A highly diluted system is typically needed for conventional methods to obtain a high amount of solid cyclic compounds (e.g., 17-20% solid contents); otherwise, a significant amount of linear phenolic resins will form.

In the process discussed in this application, however, the reaction can be carried out in a highly concentrated reaction system, yet still result in a significantly improved solid content (i.e., calixarene compounds) in the reaction products. To carry out the reaction in a highly concentrated reaction system, the mass ratio of the phenolic compound to the organic solvent at the starting of the reaction is typically no less than about 0.25:1, for instance, no less than about 0.4:1, no less than about 0.5:1, no less than about 1:1, no less than 1.25:1, or no less than 1.5:1. Typically, the mass ratio of the phenolic compound to the organic solvent at the starting of the reaction ranges from about 0.5:1 to about 2:1, from about 1:1 to about 2:1, or from about 1.25:1 to about 1.8:1.

When the reaction of the phenolic compounds and the aldehyde undergoes reflux and/or distillation stages, as discussed infra, additional organic solvent may be added to the reaction mass, for instance, after the reflux stage (if the reflux stage is conducted) and/or before the distillation stage. This is typically carried out when the reaction mass contains a high amount of solid content and is relatively viscous for subsequent handling (for instance, the subsequent filtration and washing of the reaction product). The organic solvent added at this stage can be the same as the one initially loaded in the reaction system or a different one.

Even in the scenario when additional organic solvent is added to the reaction mass (e.g., after the reflux stage, if the reflux stage is conducted, and/or before the distillation stage), the total amount of organic solvent in the reaction system during the entire condensation reaction between the phenolic compound and the aldehyde can still be relative small compared to the conventional high-dilution reaction condition. To carry out the entire reaction in a highly concentrated reaction system, the mass ratio of the phenolic compound to the total amount of the organic solvent added during the entire reaction (including the reflux stage, if the reflux stage is conducted, and distillation stage) is typically no less than about 0.25:1, for instance, no less than about 0.3:1, no less than about 0.4:1, no less than about 0.5:1, or no less than about 1:1. Typically, the mass ratio of the phenolic compound to the total amount of the organic solvent added during the entire reaction ranges from about 0.25:1 to about 2:1, or from about 0.3:1 to about 1.5:1.

Reaction Kinetics

To assist the process in forming high yield, high purity, and high selectivity calix[8]arenes, the reaction of the phenolic compounds and the aldehyde may first undergo a reflux stage. The reaction is typically carried out at an elevated temperature. The temperature range at the reflux stage depends on the boiling point of the organic solvents used in the reaction system and their azeotropes with water/aldehyde. For alkanes or ethers such as aromatic hydrocarbons or aromatic ethers, the temperature to reach the reflux stage typically ranges from about 70° C. to about 130° C., for instance, from about 90° C. to about 120° C., or from about 95° C. to about 120° C. For instance, when using an aromatic 150 fluid (i.e., an aromatic hydrocarbon solvent having a main component ranging from 9 to 12 carbon atoms; A-150) or an aromatic ether (such as diphenyl ether) as the organic solvent in the reaction system, the temperature to reach the reflux stage typically ranges from about 95° C. to about 105° C.; when using xylene as the organic solvent in the reaction system, the temperature to reach the reflux stage typically ranges from about 90° C. to about 120° C.

The control of the timing of the initial reflux stage can help improve the yield and selectivity toward the calixarene compound. Typically, the reflux stage lasts for a time period of 10 hours or longer, 12 hours or longer, or 15 hours or longer. In one embodiment, the reaction kinetics of an exemplary calix[8]arene formation indicates that the selective formation of the calixarene compound over the linear phenolic resin or other cyclic byproducts in the distillation phase more likely occurs following the 10-hour, 12-hour, 15-hour, or longer initial reflux stage.

It is possible to reduce the reaction time at the reflux stage, yet still produce a composition having a high yield, high purity, and high selectivity toward calix[8]arenes. For instance, when the heating is conducted in a more rigorous manner to heat the reaction vessel at a temperature that is higher than the temperature needed for reaching a reflux stage, the reaction time at the reflux stage can be reduced significantly. Heating under pressure can achieve the same effect. For instance, when using A-150 as the organic solvent in the reaction system, the temperature needed to reach the reflux stage typically ranges from about 95° C. to about 105° C. However, when the heating is conducted in a more rigorous manner to raise the temperature of the reaction vessel to about 115° C., the reaction time at the reflux stage can be reduced from 10 hours to 5 hours. In one embodiment, a rigorous heating results in the temperature of the reaction vessel about 5 to 20° C. higher or about 10 to 15° C. higher than the temperature needed for reaching a reflux stage. This higher temperature increases the reaction rate and can reduce the reaction time at the reflux stage to about 80%, about 70%, about 60%, about 50%, about 40%, about 30%, or about 25% of the reaction time typically needed for the reflux stage. Accordingly, the reflux time can be reduced to about 4 hours, about 5 hours, about 6 hours, about 7 hours, or about 8 hours.

It is not necessary for the reaction to undergo a reflux stage. For instance, when paraformaldehyde is used in the reaction, the reaction may not undergo a reflux stage. This provides the benefit of a significantly shortened total reaction time, while still affording a high yield, high purity, and high selectivity toward calix[8]arenes.

The reaction may also undergo a distillation stage. If a reflux stage is conducted, the distillation stage is typically after the reflux stage. The reaction mixture may be heated at an elevated temperature of 140° C. to 180° C., for instance, from about 140° C. to about 160° C., or from about 140° C. to about 150° C., to remove water from the reaction mixture.

The longer the distillation stage, generally the higher the selectivity toward the calix[8]arene compound. Typically, the distillation stage lasts for a time period of 4 hours or longer, 5 hours or longer, 6 hours or longer, 7 hours or longer, 8 hours or longer, 9 hours or longer, or 10 hours or longer. In one embodiment, the reaction kinetics of an exemplary calix[8]arene formation indicates the increase of the selectivity toward calix[8]arene over calix[6]arene after 3-6 hours of distillation.

Purification

The process to produce a calix[8]arene compound with a high yield, high purity, and high selectivity can be carried out in a one-step reaction, and in a more efficient process, without utilizing a recrystallization step.

Instead, a high-purity calix[8]arene compound can be achieved by a filtration step. Accordingly, the process further comprises filtrating the reaction product directly and drying the filtrated reaction product, thereby producing a calixarene compound containing a high purity calix[8]arene, for instance, a purity of at least about 90%, at least about 92%, at least about 95%, at least about 98%, or at least about 99%. The purity of the calix[8]arene compound is characterized by HPLC analysis, not accounting for the attached solvent and the unreacted free phenolic monomers.

This process can also produce a calixarene compound with a reduced amount of free phenolic monomers, without utilizing more complicated post-synthesis treatments. For instance, simply washing the crude reaction product with an organic solvent can remove most, if not all, free phenolic monomers. The process can also further comprise the step of filtrating the washed reaction product and drying the filtrated reaction product, thereby producing a calixarene compound with a free phenolic monomer content of about 0.5% or lower, about 0.3% or lower, or about 0.1% or lower.

Another aspect of the invention relates to a process for a high-yield, high solid-content production of a calixarene compound. The process comprises reacting a phenolic compound, an aldehyde, and a base catalyst in the presence of an organic solvent, in a highly concentrated reaction system. The mass ratio of the phenolic compound to the organic solvent in the reaction system (the organic solvent added at the starting of the reaction, or the total amount of organic solvent added during the entire condensation reaction) is no less than about 0.25:1, for instance, no less than about 0.4:1, no less than about 0.5:1, no less than about 1:1, no less than 1.25:1, or no less than 1.5:1. The process produces a calixarene-containing product having at least 30% solids, for instance, at least 35%, at least 40%, at least 45%, at least 50%, at least 55%, at least 60%, or at least 65% solids. The base catalyst used is typically a nitrogen-containing base catalyst.

Also applicable to this aspect of the invention are all the descriptions and all embodiments regarding the phenolic compound, the aldehyde, the nitrogen-containing base catalyst, the organic solvent, and their relative amounts; the reaction kinetics (including the reflux stage and/or distillation stage); and the purification discussed above in the first aspect of the invention relating to the process for preparing a calixarene compound.

Another aspect of the invention relates to a process for the selective synthesis of a calix[8]arene compound. The process comprises reacting a phenolic compound, an aldehyde, and a nitrogen-containing base as a catalyst, in the presence of an organic solvent. Optionally, the reacting step is carried out under reflux conditions, for a time period of 10 hours or longer, 12 hours or longer, or 15 hours or longer, at a normal reflux temperature range, or for a reduced reflux time if heating is conducted in a more rigorous manner or under pressure, as discussed above in the first aspect of the invention relating to the process for preparing a calixarene compound. When paraformaldehyde is used in the reaction, the reaction may not undergo a reflux stage. The process further comprises heating the reaction mixture at an elevated temperature of about 140° C. to about 180° C. for a time period of 4 hours or longer, for instance, 5 hours or longer, 6 hours or longer, 7 hours or longer, 8 hours or longer, 9 hours or longer, or 10 hours or longer, to remove water from the reaction mixture and selectively produce a calixarene compound containing at least 70% calix[8]arene, for instance, at least about 90%, at least about 92%, at least about 95%, at least about 98%, or at least about 99% of calix[8]arene.

Also applicable to this aspect of the invention are all the descriptions and all embodiments regarding the phenolic compound, the aldehyde, the nitrogen-containing base catalyst, the organic solvent, and their relative amounts; the reaction kinetics (including the reflux stage and/or distillation stage); and the purification discussed above in the first aspect of the invention relating to the process for preparing a calixarene compound.

Another aspect of the invention relates to a process for a one-step, selective synthesis of a high-purity calix[8]arene compound. The process comprises reacting, in a one-step process, a phenolic compound and an aldehyde in the presence of a base catalyst to form a high-purity calix[8]arene compound, without carrying out a recrystallization step. The base catalyst used is typically a nitrogen-containing base catalyst.

The process can further comprise the step of filtrating the reaction product and drying the filtrated reaction product, thereby producing a calix[8]arene compound with a purity of at least about 90%, at least about 92%, at least about 95%, at least about 98%, or at least about 99%.

Also applicable to this aspect of the invention are all the descriptions and all embodiments regarding the phenolic compound, the aldehyde, the nitrogen-containing base catalyst, the organic solvent, and their relative amounts; the reaction kinetics (including the reflux stage and/or distillation stage); and the purification discussed above in the first aspect of the invention relating to the process for preparing a calixarene compound.

Another aspect of the invention relates to a process for the selective synthesis of a calix[8]arene compound with a low free phenolic monomer content. The process comprises the steps of reacting a phenolic compound and an aldehyde in the presence of a base catalyst, and washing the reaction product to remove free phenolic compound monomers, to produce a calix[8]arene compound with a free phenolic monomer content of about 0.5% or lower, for instance, about 0.3% or lower, or about 0.1% or lower. The process does not include a recrystallization step. The base catalyst used is typically a nitrogen-containing base catalyst.

Also applicable to this aspect of the invention are all the descriptions and all embodiments regarding the phenolic compound, the aldehyde, the nitrogen-containing base catalyst, the organic solvent, and their relative amounts; the reaction kinetics (including the reflux stage and/or distillation stage); and the purification discussed above in the first aspect of the invention relating to the process for preparing a calixarene compound.

Other aspects of the invention also relate to a phenolic oligomer composition prepared by any one of the processes discussed above.

Applications

The calixarene compounds or phenolic oligomer compositions prepared by the processes disclosed herein can be used in a wide range of applications.

One aspect of the invention relates to a demulsifier or dehazer composition comprising the calixarene compounds or phenolic oligomer compositions prepared by the processes discussed above. The demulsifier or dehazer composition may further comprise one or more other components commonly used in a demulsifier or dehazer composition, as understood by those of skill in the art. The demulsifier or dehazer composition may be used for a wide variety of applications for oil and water separation, such as refinery and fuel dehazing. The demulsifier or dehazer composition may further act as salt-sequestering agents in crude oil, for instance, to sequester salt from crude oil and as a result, reduce salt levels in crude oil.

The calixarene compounds or phenolic oligomer compositions prepared by the processes disclosed herein may also be used as the starting material for overbasing. For instance, calixarene compounds or phenolic oligomer compositions or their functional derivatives can be attached with metal base moieties forming an overbased metal salt, to neutralize the acidic materials and disperse sludge in lubricating oil compositions or fuel compositions. See, e.g., salicyclic calixarenes and their use as lubricant additives, described in U.S. Pat. No. 6,200,936, which is incorporated herein by reference in its entirety, to the extent not inconsistent with the subject matter of this disclosure. As another example, an additive package based on overbased calixarene compounds or phenolic oligomer compositions prepared by the processes disclosed herein, e.g., a p-didecylcalixarene compound (such asp-dodecylcalix[5,6,8] compounds), can perform well in the TEOST HMT test (Thermo-Oxidation Engine Oil Simulation Test), which is employed to evaluate the ability of an engine oil to control the formation of deposits at high temperatures. See, e.g., salicyclic calixarenes and their use as lubricant additives, described in a doctoral thesis by Alessandro Burlini, entitled "SYNTHESIS OF NEW CALIXARENE-BASED LUBRICANT ADDITIVES," published by University of Parma, Department of Chemistry (Italy) on Mar. 18, 2016, which is incorporated herein by reference in its entirety, to the extent not inconsistent with the subject matter of this disclosure.

Another aspect of the invention relates to a paraffin-containing fluid composition comprising a resin containing the calixarene compounds or phenolic oligomer compositions prepared by the processes discussed above, and one or more paraffin-containing fluids. The resin is at least partially soluble in the paraffin-containing fluid, and disperses the paraffin in the fluid composition and/or inhibits the deposition of the paraffin crystals. The fluid can be any hydrocarbon fluid in the oilfield including, but not limited to, a crude oil, home heating oil, lubricating oil (such as an engine oil), and natural gas. These oilfield hydrocarbon fluids typically contain paraffin or paraffin wax. The composition containing the calixarene compounds or phenolic oligomer compositions prepared by the processes may be used for a wide variety of applications to disperse paraffin crystals and/or inhibit paraffin crystal deposition, such as for treating a well or vessel surface to reduce the deposition of paraffin crystals on the well or vessel surface. Additional details on the methods of using calixarene compounds in inhibiting paraffin crystal deposition may be found in U.S. patent application Ser. No. 15/879,293 to Cable et al, entitled "Paraffin inhibition by solubilized calixarenes," filed on Jan. 24, 2018, which is incorporated herein by reference in its entirety, to the extent not inconsistent with the subject matter of this disclosure.

The calixarene compounds or phenolic oligomer composition prepared by the processes disclosed herein may be used as various other agents or intermediates to prepare other useful agents.

For instance, the calixarene compounds or phenolic oligomer compositions prepared by the processes disclosed here may be used as charge control agents to create a desired charge level and polarity, which may be useful as coating additives that can be applied to surfaces (e.g., aluminum oil cans), as chemical sensors for determining onset of rusting in applications such as marine coatings or aerospace applications, or in toners for developing electrostatic images used for electrophotography, electrostatic recording, electrostatic printing, etc.

The calixarene compounds or phenolic oligomer composition prepared by the processes disclosed here may be used as host molecules, to form a complex or an association with one or more guest molecules, such as ions, metals, organic compounds of various sizes, compounds carrying charges, and salts. By doing so, they may aid in compound delivery (e.g., drug-delivery vehicles) by encapsulating a compound within the cavity of the calixarene compound, thereby aiding in the solubilization of the guest molecule. Or they may be used as extractants to extract small molecules or metal ions (e.g., via chelation or complexation), or act as ionophores to transport the metal ions across cell membranes. These technologies are further illustrated in U.S. Pat. No. 7,524,469, and U.S. Patent Application Publication No. 2012/0145542; both of which are hereby incorporated by reference in their entirety, to the extent not inconsistent with the subject matter of this disclosure.

The calixarene compounds or phenolic oligomer compositions prepared by the processes disclosed here may be used as adhesion promotors to accelerate polymerization of monomers in an adhesive composition. This technology is further illustrated in Gutsche, "Calixarenes, An Introduction," page 236 (2d Edition, RSC Publishing, Cambridge, UK) (2008), which is hereby incorporated by reference in its entirety, to the extent not inconsistent with the subject matter of this disclosure.

The calixarene compounds or phenolic oligomer composition prepared by the processes disclosed here may be used in as positive or negative resists, for pattern formation and etching to form a hyperfine structure. The resulting resists can be used to fabricate printed circuit boards, sand carving, microelectronics, and patterning and etching of substrates.

The calixarene compounds or phenolic oligomer composition prepared by the processes disclosed here may be used as catalysts for a variety of chemical reactions. For example, because of their unique topology, complexes in which a calixarene ligand coordinates to a transition metal are potentially valuable for olefin polymerization. This technology is further illustrated in U.S. Pat. No. 6,984,599, which is hereby incorporated by reference in its entirety, to the extent not inconsistent with the subject matter of this disclosure.

The calixarene compounds or phenolic oligomer composition prepared by the processes disclosed here may be used as antifoulants that may be applied to surfaces that normally undergo biofouling (e.g., ship hulls), to inhibit biofouling, or disperse preexisting biofouling.

The calixarene compounds or phenolic oligomer composition prepared by the processes disclosed here may be used as thermal stabilizers, for instance, as curing agents, to aid in cross-linking in the curing processes of polymers.

Additionally, the calixarene compounds or phenolic oligomer composition prepared by the processes disclosed here can be used in any other applications involving the use of a calixarene compound, such as accelerators, additives, binding agents, stabilizing agents, flame retardants (in which the calixarene compounds or phenolic oligomer composition prepared by the processes disclosed here can be a host compound in a flame retardant composition; see, e.g., WO 2017/087115, which is incorporated herein by reference in its entirety, to the extent not inconsistent with the subject matter of this disclosure), adsorbent/absorbant materials, sequestering agents, hardeners, API-transportation, etc.

The calixarene compounds or phenolic oligomer compositions prepared by the processes disclosed here may be further de-alkylated via sulfonation by sulfuric acid or via nitration by nitric acid, using the methods described in U.S. Pat. Nos. 5,952,526 and 2,868,844; which are incorporated herein by reference in their entirety. The sulfonated or nitrated calixarenes are typically soluble and may be used for various applications as described herein.

The calixarene compounds or phenolic oligomer compositions prepared by the processes disclosed here may be used as tackifier resins in a rubber compound for tire applications. For instance, the calixarene compounds or phenolic oligomer compositions or their functional derivatives may be incorporated into rubber compounds as a phenolic tackifier resin or a part of a phenolic tackifier resin to increase the adhesion strength between a fabric or metal wire with the rubber compound.

The calixarene compounds or phenolic oligomer compositions prepared by the processes disclosed here may be further treated or reacted with another polymer component to for form a radial polymer, using the methods described in, e.g., U.S. Patent Application Publication No. 2017/0051224, which is incorporated herein by reference in its entirety. The resulting calixarene-based radial polymer can be used as viscosity index improver additives in lubricant compositions.

Additional aspects, advantages and features of the invention are set forth in this specification, and in part will become apparent to those skilled in the art on examination of the following, or may be learned by practice of the invention. The inventions disclosed in this application are not limited to any particular set of or combination of aspects, advantages and features. It is contemplated that various combinations of the stated aspects, advantages and features make up the inventions disclosed in this application.

EXAMPLES

The following examples are given as particular embodiments of the invention and to demonstrate the practice and advantages thereof. It is to be understood that the examples are given by way of illustration and are not intended to limit the specification or the claims that follow in any manner.

Example 1. Synthesis of tert-butylcalix[8]arenes Using 1,8-diazabicyclo[5.4.0]undec-7-ene (DBU) as the Catalyst

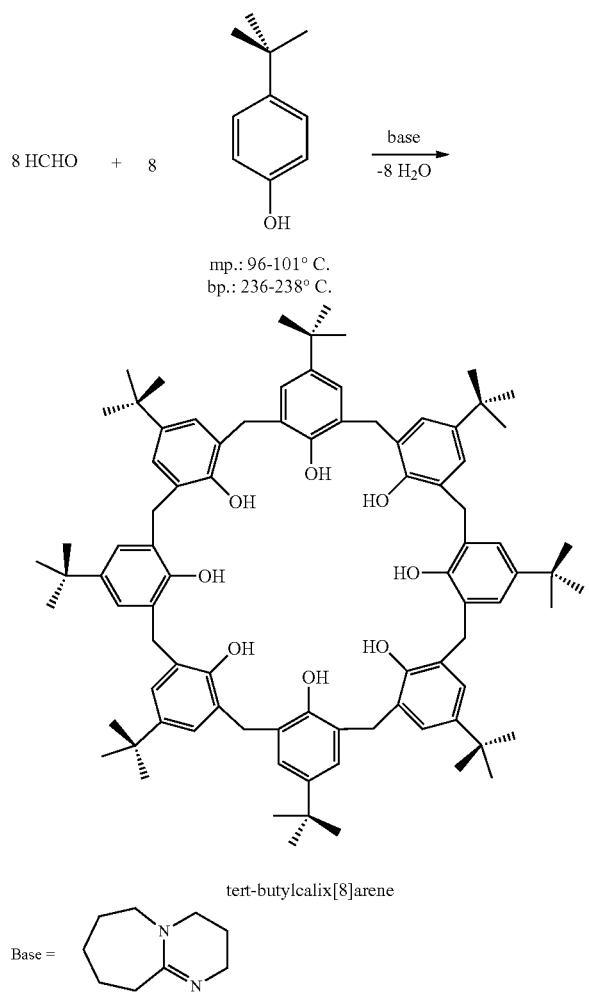

A 2 L round bottom flask, equipped with an overhead stirrer, thermocouple (having a gas inlet, through which nitrogen stream can be applied), and condenser, was loaded with 550.2 g para-tert-butylphenol (PTBP) briquettes (3.66 mol) and 370.0 g A-150 (Solvesso™ 150 Fluid). A gentle nitrogen flow was applied on the surface of the hot reaction mass and the reactor was heated to about 80° C. within 20 minutes. Mixing was set to 112 rpm. Five minutes later, when all the PTBP and A-150 formed a clear solution, 8.8 g DBU (98%, 0.058 mol) was added dropwise at a temperature of 80° C., and a slight exotherm was observed. The reaction mixture was heated to 85° C. and 220 g of 50 wt % formaldehyde solution (3.66 mol) was added within 1 hour and 20 minutes, while the formaldehyde solution was heated periodically with a heat gun to prevent formaldehyde from solidification.

After the formaldehyde addition, the temperature was increased to 90° C., the nitrogen flow was decreased while the circulating cooling water flow was increased to combat extra moisture in the condenser, and the conditions were held for 30 minutes. A formaldehyde trap was placed under the condenser, with the arm to the trap wrapped with aluminum foil. The reaction mixture was heated to reflux for a total of 15 hours. At the end of the reflux, the reaction mass was about 103° C.

The formaldehyde trap was then exchanged against a Dean-Stark trap which was filled with A-150. The condenser was placed on top of the Dean-Stark trap and the heating was resumed to remove the water in the reaction system. About 2.5 hours later, the temperature of the reaction mass reached 111° C., and additional 55.9 g of A-150 was added to the pot. The water removal was facilitated by a slight nitrogen sweep over the surface of the reaction mass. The temperature of the reaction mass reached 145° C. 70 minutes later, and was held at this temperature for additional 5 hours. The reaction mass became thicker and thicker. A total of 165.2 g distillate was taken out, and the product weighed 1028.3 g.

The GPC results of the final reaction mass are shown in FIG. 1. FIG. 1 shows that the reaction product had a very lean and sharp peak. Theoretically, the solid content of the crude reaction mass was calculated to be 57.75 wt % (assuming all water from formaldehyde solution and produced from the reaction were removed; and all excess formaldehyde was removed). The final reaction mass contained 2.2 wt % free PTBP (which corresponds to 22.6 g or 4.1 mol % of unreacted PTBP) and less than 15 ppm free formaldehyde.

Figure 2:
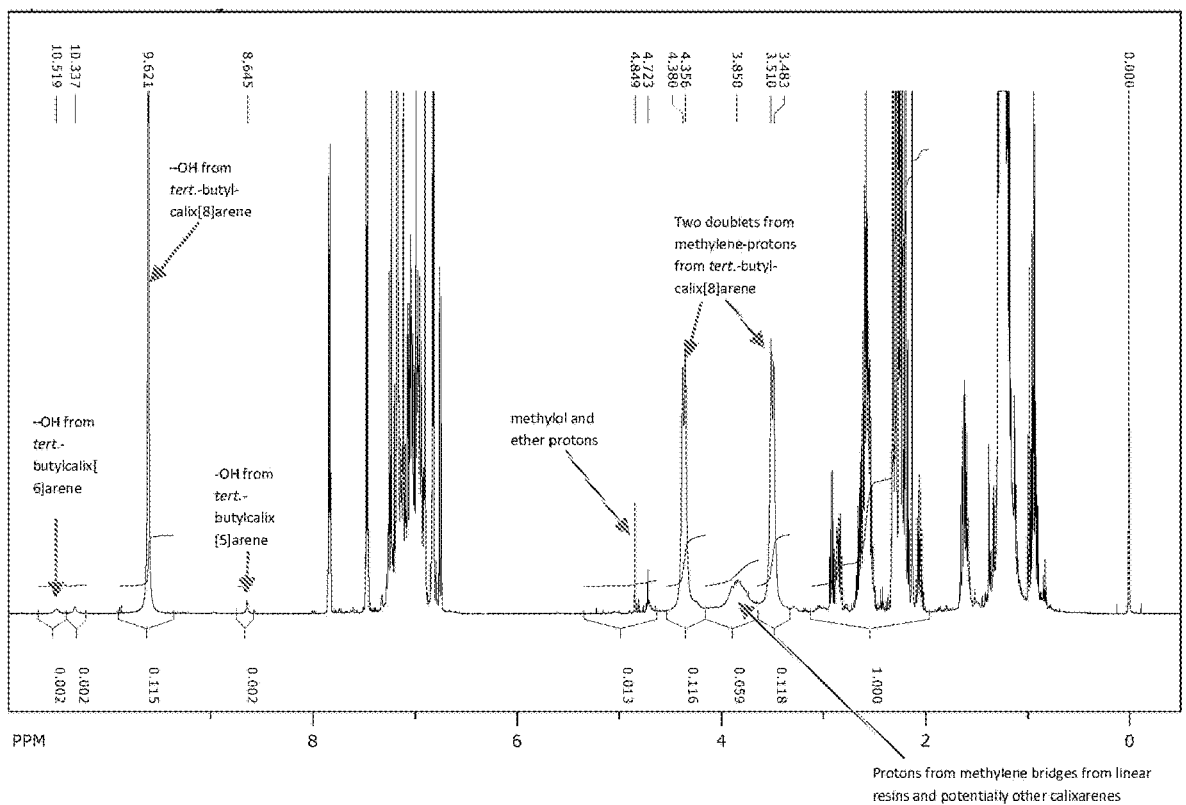
FIG. 2 shows the $^1$H-NMR results of the final reaction mass prepared from Example 1.

The $^1$H-NMR results of the final reaction mass are shown in FIG. 2. In FIG. 2, the integrals of the phenolic OH protons for the different calixarenes in the $^1$H-NMR spectra show the high selectivity for the calix[8]arene.

The yields of the cyclic phenolic resins were determined by further analysis of the $^1$H-NMR results of the crude reaction mass. Although the $^1$H-NMR does not show the unreacted PTBP, the ratio of the integrals of the free phenolic OH signals from the calixarenes (between 8.5 and 11 ppm; see e.g., Stewart et al., *J. Am. Chem. Soc.* 121:4136-46 (1999), which is hereby incorporated by reference in its entirety, to the extent not inconsistent with the subject matter of this disclosure) to the integrals of the proton signals from the methylene bridges for linear and cyclic resins (between 3.4 to 4.5 ppm) provided an estimate for the yields of the respective calixarenes. The signals of methylols and dibenzylethers are low since they are the precursors of the calixarene synthesis—the lower their integral values, the better the conversion.

The analysis results of the $^1$H-NMR in FIG. 2 are as follows.

| | |
|---|---|
| Integrals for calixarene phenolic OH protons (for all calixarenes) | 0.121 |
| Integrals for two protons of all methylene bridges (cyclic and linear resins) | 0.295 |
| Integrals for one proton of all methylene bridges (cyclic and linear resins) | 0.1475 |
| Ratio of calixarene phenolic OH protons to the protons of all methylene bridges | 0.121/0.1475 = 82.0% |

Taking into account the 4.1 mol % unreacted PTBP in the yield calculation (i.e., 95.9 mol % of the PTBP had reacted) resulted in a crude calixarene yield of 78.7% (i.e., 82.0%× 0.959). That is to say, the theoretical yield of all cyclic components in this crude reaction mass was 78.7%.

Applying the same calculation for the tert-butylcalix[8] arene provided the following results.

| | |
|---|---|
| Integrals for tert-butylcalix[8]arene phenolic OH protons | 0.115 |
| Integrals for one proton of all methylene bridges (cyclic and linear resins) | 0.1475 |
| Ratio of tert-butylcalix[8]arene phenolic OH protons to the protons of all methylene bridges | 0.115/0.1475 = 78.0% |

Taking into account the 4.1 mol % unreacted PTBP in the yield calculation resulted in a crude tert-butylcalix[8]arene yield of 74.8% (i.e., 78.0%×0.959). That is to say, the theoretical yield of tert-butylcalix[8]arene in this crude reaction mass was 74.8%.

Example 2. Synthesis of Tert-Butylcalix[8]Arenes Using Tetraethylammonium Hydroxide (TEAOH) as the Catalyst (in a More Diluted System)

A 500 ml round bottom flask, equipped with an overhead stirrer, thermocouple, overhead addition tank, moisture trap, and condenser was loaded with 112.7 g PTBP briquettes (0.75 mol) and 100.2 g A-150 (Solvesso™ 150 Fluid). A gentle nitrogen flow was applied on the surface of the hot reaction mass and the reactor was heated to about 90° C. When all the PTBP and A-150 formed a clear solution, 5.5 g TEAOH solution (40 wt % in water, 0.015 mol) was added dropwise at a temperature of 87° C., and this temperature was held for 20 minute. Starting at 87° C., a total of 43.6 g of 51.7 wt % formaldehyde solution (0.75 mol) was added within 12 minutes.

After the formaldehyde addition, the reaction was kept at about 87° C. for one hour. Then, the reaction mixture was heated to reflux for a total of 12 hours. At the end of the reflux, the reaction mass was about 101° C.

The reaction mass was diluted with 100.1 g more A-150 solvent. The reactor was then heated and the temperature target was set to 145° C. to remove the water, and was kept at about 145° C. for about 10 hours until a total of 33.9 g of the lower layer was removed. The crude reaction mass contained 3.8 wt % PTBP.

Figure 3:
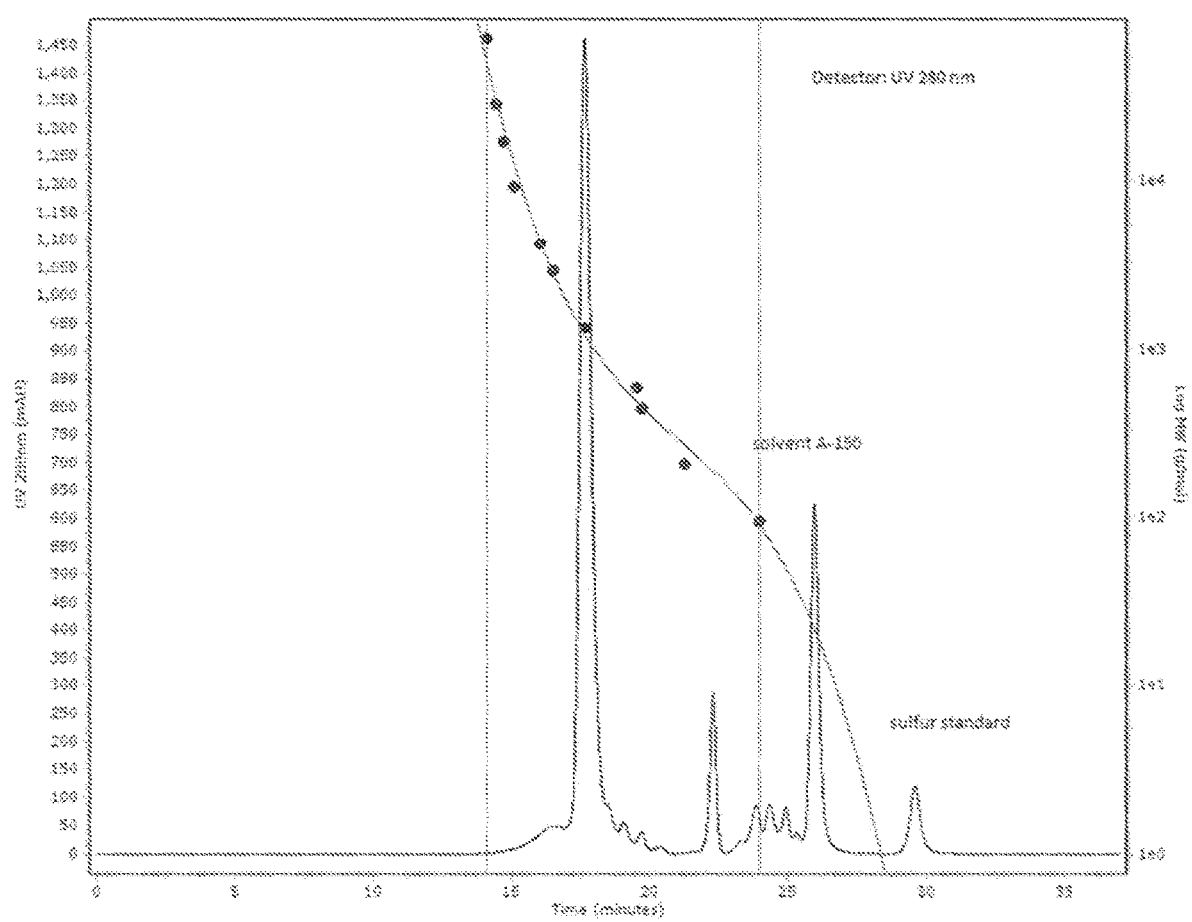
FIG. 3 shows the GPC results of the crude reaction mass prepared from Example 2.

The GPC results of the crude reaction mass are shown in FIG. 3. With a theoretical reaction mass of 324.2 g (assuming all water from formaldehyde solution and produced from the reaction were removed; and all excess formaldehyde was removed), the crude reaction mass contained 3.82 wt % free PTBP (which corresponds to 12.38 g or 11.0 mol % of unreacted PTBP).

Figure 4:
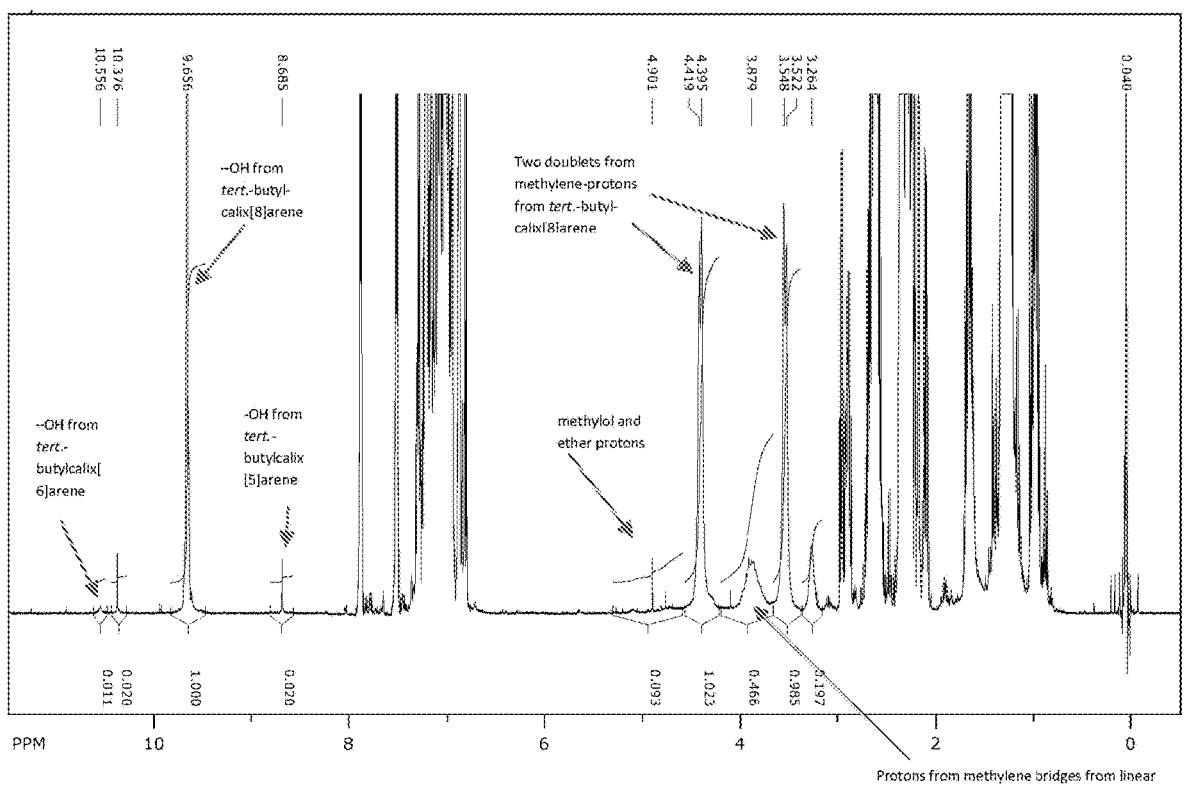
FIG. 4 shows the $^1$H-NMR results of the crude reaction mass prepared from Example 2.

The $^1$H-NMR results of the crude reaction mass are shown in FIG. 4. The yields of the cyclic phenolic resins were determined by further analysis of the $^1$H-NMR results of the crude reaction mass, using the calculation methodology discussed in Example 1.

The analysis results of the $^1$H-NMR in FIG. 4 are as follows.

| | |
|---|---|
| Integrals for calixarene phenolic OH protons (for all calixarenes) | 1.051 |
| Integrals for two protons of all methylene bridges (cyclic and linear resins) | 2.567 |
| Integrals for one proton of all methylene bridges (cyclic and linear resins) | 1.2835 |
| Ratio of calixarene phenolic OH protons to the protons of all methylene bridges | 1.051/1.2835 = 81.9% |

Taking into account the 11.0 mol % unreacted PTBP in the yield calculation (i.e., 89.0 mol % of the PTBP had reacted) resulted in a crude calixarene yield of 72.9% (i.e., 81.9%× 0.89). That is to say, the theoretical yield of all cyclic components in this crude reaction mass was 72.9%.

Applying the same calculation for the tert-butylcalix[8] arene provided the following results.

| | |
|---|---|
| Integrals for tert-butylcalix[8]arene phenolic OH protons | 1.000 |
| Integrals for one proton of all methylene bridges (cyclic and linear resins) | 1.2835 |
| Ratio of tert-butylcalix[8]arene phenolic OH protons to the protons of all methylene bridges | 1.000/1.2835 = 77.9% |

Taking into account the 11.0 mol % unreacted PTBP in the yield calculation resulted in a crude tert-butylcalix[8]arene yield of 69.3% (i.e., 77.9%×0.89). That is to say, the theoretical yield of tert-butylcalix[8]arene in this crude reaction mass was 69.3%.

This crude reaction mass obtained above was then cooled to about 80° C., and was easily filtered through a Buechner funnel. The filter cake was successively washed with portions of A-150 (a total of 102.8 g) to result in a wet filter cake. After drying in vacuum at 130° C., the product tert-butylcalix[8]arene was obtained in an isolated yield of 72.2% (theoretical yield), with an HPLC purity of 98.8% (area % at 281 nm) and less than 0.05 wt % PTBP (GC).

Example 3. Synthesis of Tert-Butylcalix[8]Arenes Using Tetramethylammonium Hydroxide (TMAOH) as the Catalyst and Paraformaldehyde as the Aldehyde Source A 500 ml round bottom flask, equipped with an overhead stirrer, thermocouple, Dean-Stark trap, and condenser was loaded with 112.62 g PTBP briquettes (0.75 mol), 22.68 g paraformaldehyde (0.755 mol), and 204.65 g xylene. The azeo receiver was filled with 27.3 g xylene. A gentle nitrogen flow was applied on the surface of the reaction mass while stirring was switched on at 150 rpm. A 5.51 g TMAOH solution (25 wt % in methanol, 0.015 mol) was added at a low temperature.

The reaction mixture was then heated, and reflux (when xylene formed azeotropes with the formed water) was observed at 119° C.

Figure 5:
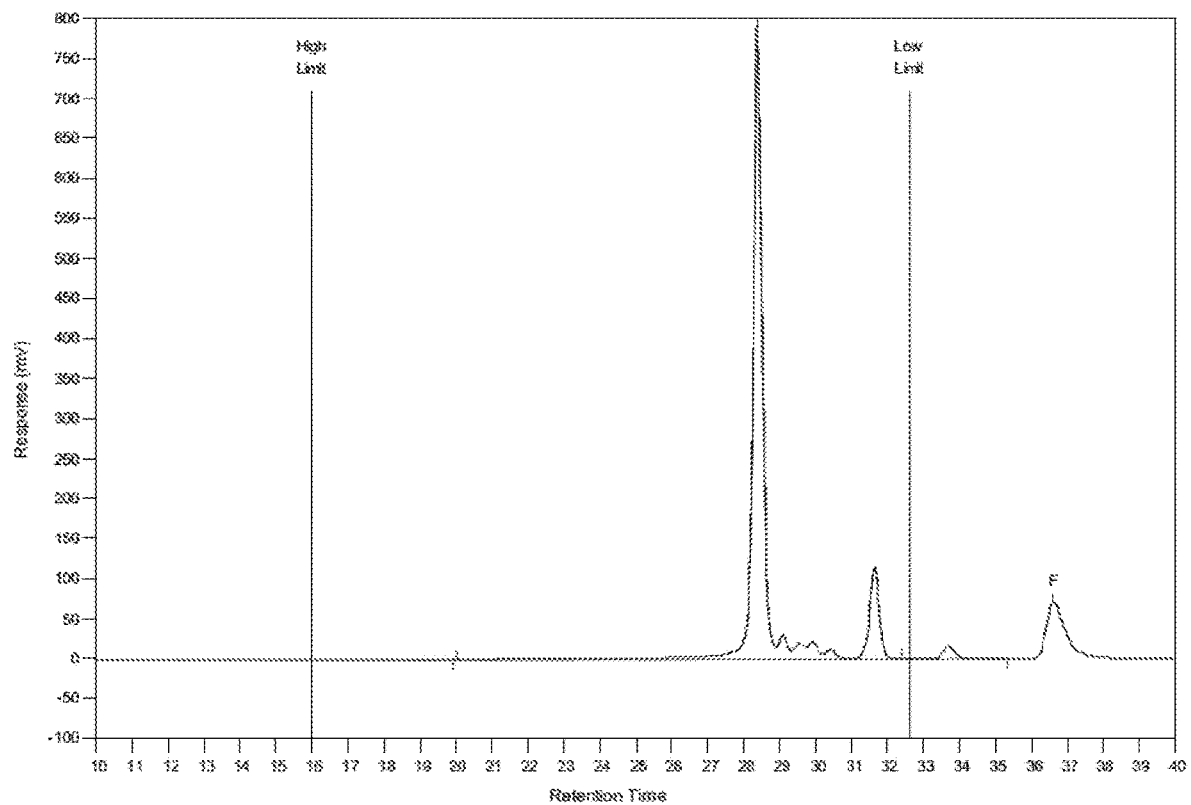
FIG. 5 shows the GPC results of the crude reaction mass prepared from Example 3.
Figure 6:
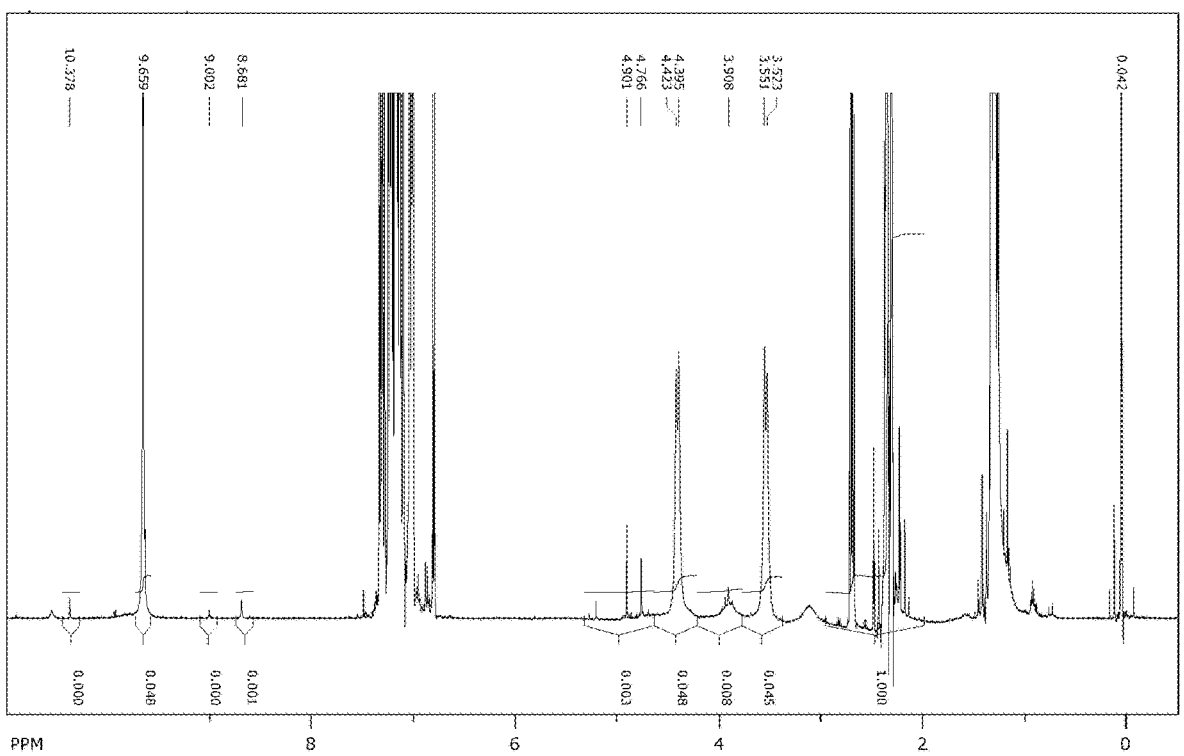
FIG. 6 shows the $^1$H-NMR results of the crude reaction mass prepared from Example 3.

About 2.5 hours after heating was started, the temperature of the reaction mass reached about 140° C., and was kept for about 10.5 hours to remove the formed water as completely as possible. Eventually, a total of 17.35 g lower layer (water) was removed from the Dean-Stark trap. The crude reaction mass contained 4.92 wt % free PTBP as well as 58.9 wt % xylene. The GPC results of the crude reaction mass are shown in FIG. 5. The $^1$H-NMR results of the crude reaction mass are shown in FIG. 6.

This crude reaction mass was then cooled to 80° C., and was easily filtered through a Buechner funnel. The filter cake was successively washed with five portions of xylene (a total of 533.1 g) to result in a filter cake with 0.12 wt % free PTBP and 8.94 wt % xylene. After drying, the product tert-butylcalix[8]arene was obtained in an isolated yield of 69.3% (of theoretical yield), with an HPLC purity of 95.2% (area % at 281 nm) and possibility of 2.9% tert-butylcalix [9]arene as a side product, and 0.08 wt % PTBP (GC).

Example 4. Synthesis of Tert-Amylcalix[8]Arenes Using Tetramethylammonium Hydroxide (TMAOH) as the Catalyst

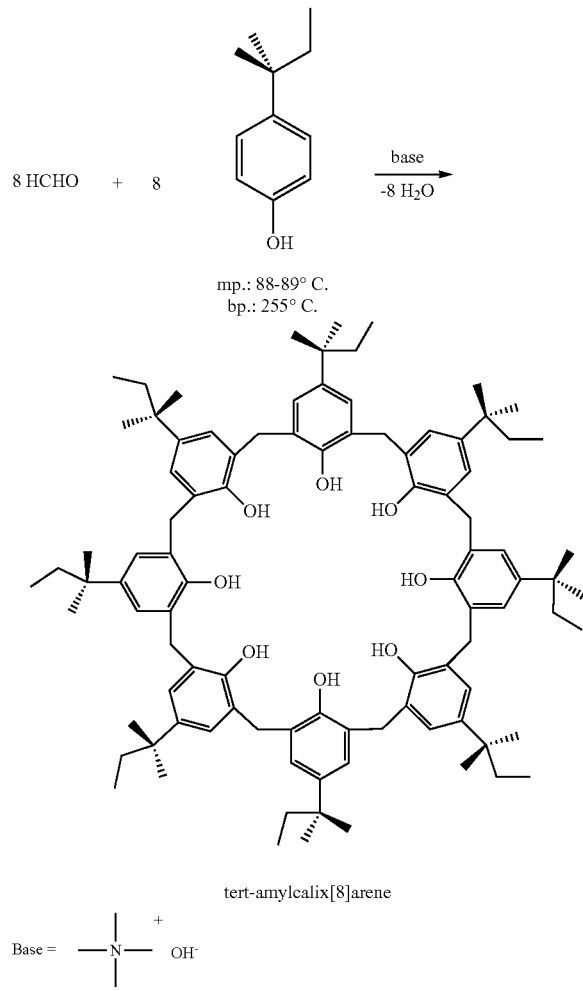

A 500 ml round bottom flask, equipped with an overhead stirrer, thermocouple, overhead addition tank, moisture trap, and condenser was loaded with 123.2 g para-tert-amylphenol (PTAP) briquettes (0.75 mol) and 90.1 g A-150 (Solvesso™ 150 Fluid). A gentle nitrogen flow was applied on the surface of the hot reaction mass and the reactor was heated to about 90° C. When all the PTAP and the A-150 formed a clear solution, 5.5 g of TMAOH solution (25 wt % in methanol, 0.015 mol) was added dropwise at a temperature of 89.3° C. over the course of 3 minutes, and this temperature was hold for 60 minutes. At 89.6° C., a total of 51.4 g of 50 wt % formaldehyde solution (0.86 mol) was added within 18 minutes.

After the formaldehyde addition, the reaction was kept at 90° C. for 1.75 hours. The reaction mixture was then heated to reflux at about 99° C. for a total of 12 hours. At the end of the reflux, the reaction mass was at 99.9° C.

The reaction mass was diluted with 70.2 g more A-150 solvent and the empty leg of the azeo trap was filled with 24.5 g A-150. The reactor was then heated and the temperature target was set to 145° C. to remove the water. A lower layer of 13.1 g was removed at 118.2° C. About 62 minutes after the heating was started, the temperature of the reaction mass reached about 145° C., and was kept for about 10 hours until a total of 30.8 g of the lower layer was removed (not all the water/methanol had come out). The crude reaction mass contained 1.3 wt % PTAP as well as 48.5 wt % A-150.

Figure 7:
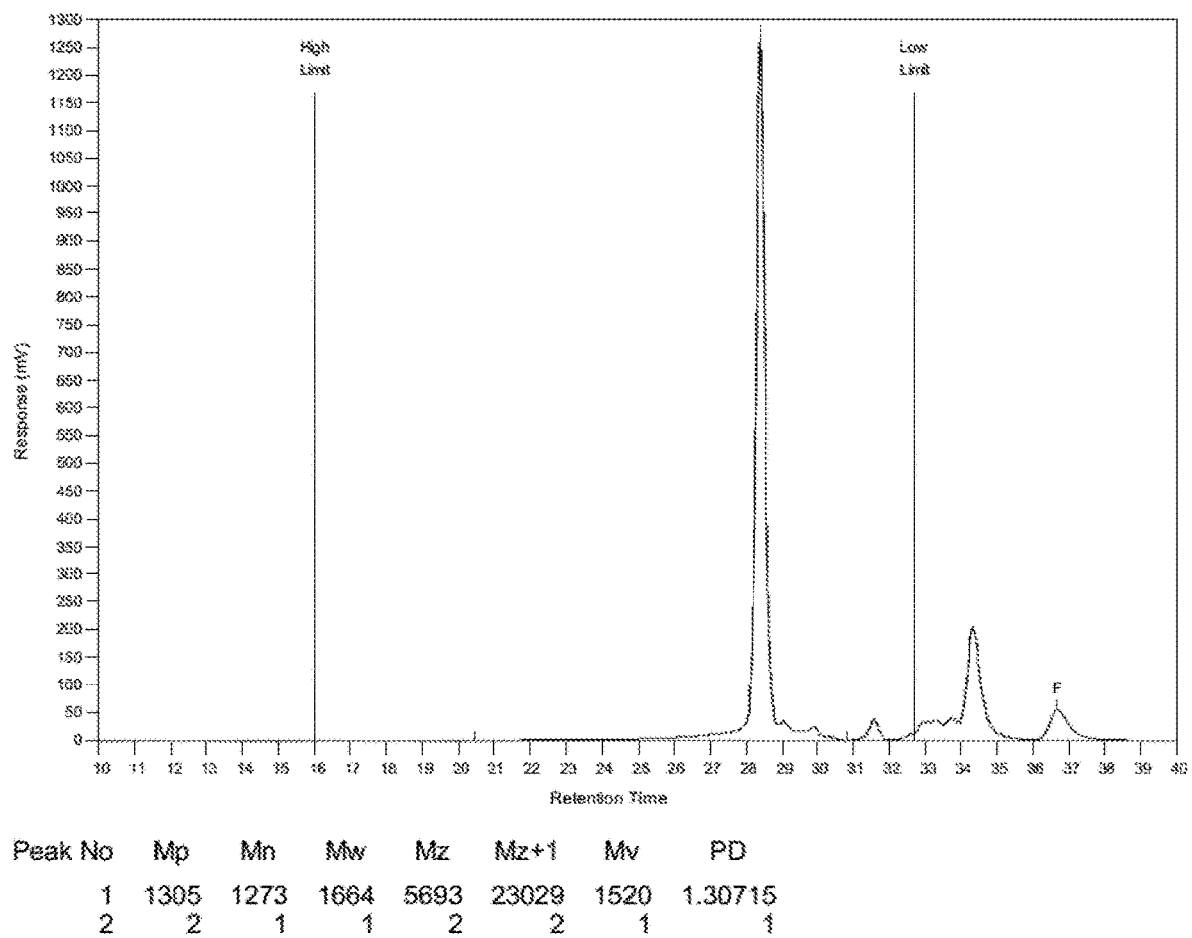
FIG. 7 shows the GPC results of the crude reaction mass prepared from Example 4.

The GPC results of the crude reaction mass are shown in FIG. 7. Theoretically, the solid content of the crude reaction mass was calculated to be 45.2 wt % (assuming all water from formaldehyde solution and produced from the reaction were removed; all methanol was removed; and all excess formaldehyde was removed). The crude reaction mass contained 1.3 wt % free PTAP (which corresponds to 3.8 g or 3.1 mol % of unreacted PTAP).

Figure 8:
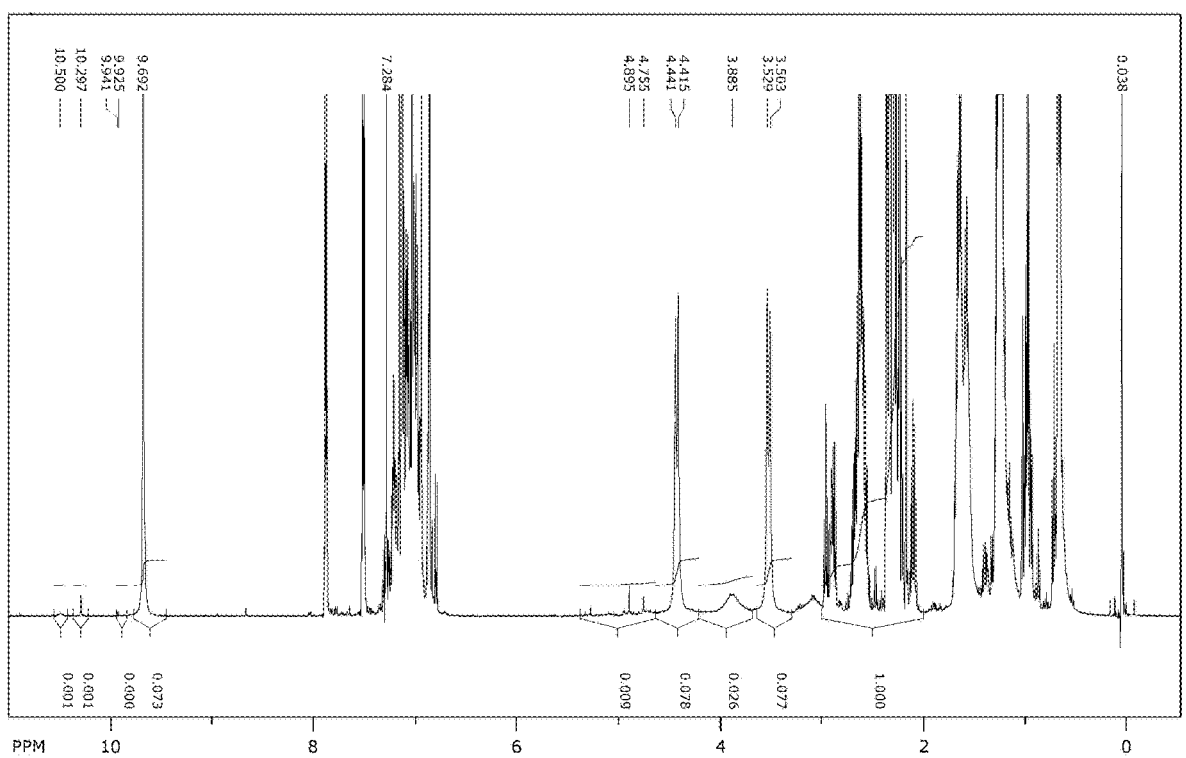
FIG. 8 shows the $^1$H-NMR results of the crude reaction mass prepared from Example 4.

The $^1$H-NMR results of the crude reaction mass are shown in FIG. 8. The yields of the cyclic phenolic resins were determined by further analysis of the $^1$H-NMR results of the crude reaction mass, using the calculation methodology discussed in Example 1. It was understood that the $^1$H-NMR does not allow the quantification of the free monomer content; but the GPC results of the final reaction mass display all components in the reaction mass (with their respective resonances at the picked wavelength (here 280 nm)).

The analysis results of the $^1$H-NMR in FIG. 8 are as follows.

| | |
|---|---|
| Integrals for calixarene phenolic OH protons (for all calixarenes) | 0.075 |
| Integrals for two protons of all methylene bridges (cyclic and linear resins) | 0.181 |
| Integrals for one proton of all methylene bridges (cyclic and linear resins) | 0.0905 |
| Ratio of calixarene phenolic OH protons to the protons of all methylene bridges | 0.075/0.0905 = 82.9% |

Taking into account the 3.1 mol % unreacted PTAP in the yield calculation (i.e., 96.9 mol % of the PTAP had reacted) resulted in a crude calixarene yield of 80.3% (i.e., 82.9%× 0.969). That is to say, the theoretical yield of all cyclic components in this crude reaction mass was 80.3%.

Applying the same calculation for the tert-amylcalix[8] arene provided the following results.

| | |
|---|---|
| Integrals for tert-amylcalix[8]arene phenolic OH protons | 0.073 |
| Integrals for two protons of all methylene bridges (cyclic and linear resins) | 0.181 |
| Integrals for one proton of all methylene bridges (cyclic and linear resins) | 0.0905 |
| Ratio of tert-amylcalix[8]arene phenolic OH protons to the protons of all methylene bridges | 0.073/0.0905 = 80.7% |

Taking into account the 3.1 mol % unreacted PTAP in the yield calculation resulted in a crude tert-amylcalix[8]arene yield of 78.2% (i.e., 80.7%×0.969). That is to say, the theoretical yield of tert-amylcalix[8]arene in this crude reaction mass was 78.2%. This is close to the observed isolated yield.

This crude reaction mass obtained above was then cooled to about 80° C., and was easily filtered through a Buechner funnel. The filter cake was successively washed with three portions of A-150 (a total of 454.3 g) to result in a wet filter cake with 0.3 wt % free PTAP and 6.9 wt % A-150. After drying, the product tert-amylcalix[8]arene was obtained in an isolated yield of 76.6% (theoretical yield), with an HPLC purity of 99.3% (area % at 281 nm).

Example 5. Synthesis of Tert-Octylcalix[8]Arenes Using Tetraethylammonium Hydroxide (TEAOH) as the Catalyst

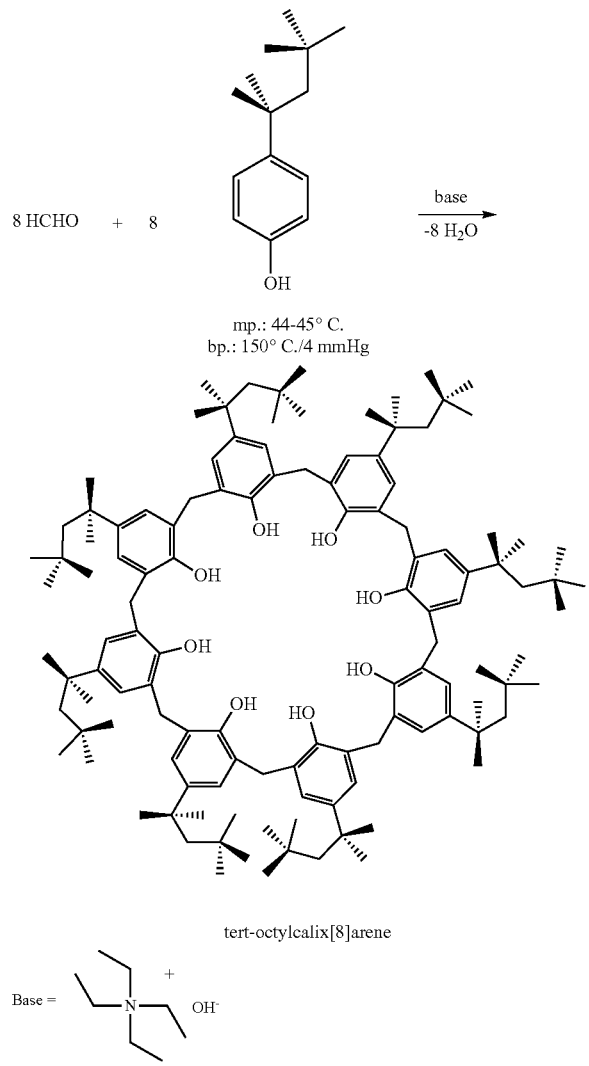

A 500 ml round bottom flask, equipped with an overhead stirrer, thermocouple, overhead addition tank, moisture trap, and condenser was loaded with 154.7 g para-tert-octylphenol (PTOP) briquettes (0.75 mol) and 89.6 g A-150 (Solvesso™ 150 Fluid). A gentle nitrogen was applied on the surface of the hot reaction mass and the reactor was heated to about 90° C. When all the PTOP and the A-150 formed a clear solution, 5.5 g of a 40% solution of TEAOH (40 wt % in water, 0.015 mol) was added dropwise at a temperature of 92.1° C. over the course of 5 minutes, and this temperature was hold for 100 minutes. At 90.1° C., a total of 50.5 g of 50 wt % formaldehyde solution (0.84 mol) was added within 23 minutes.

After the formaldehyde addition, the reaction was kept at 90° C. for 1 hour. The reaction mixture was then heated to reflux at about 100° C. for a total of 12 hours. At the end of the reaction, the reaction mass was about 100° C.

The reaction mass was diluted with 13.5 g more A-150 solvent and the empty leg of the azeo trap was filled with 24.4 g A-150. The reactor was then heated and the temperature target was set to 145° C. to remove the water. A lower layer of 16.9 g was removed at 120.5° C. About 1.75 hours after the heating was started, the temperature of the reaction mass reached about 145° C., and was kept for about 10 hours until a total of 36.3 g of the lower layer was removed (not all the water/methanol had come out). The crude reaction mass contained 1.4 wt % PTOP as well as 37.9 wt % A-150.

Figure 9:
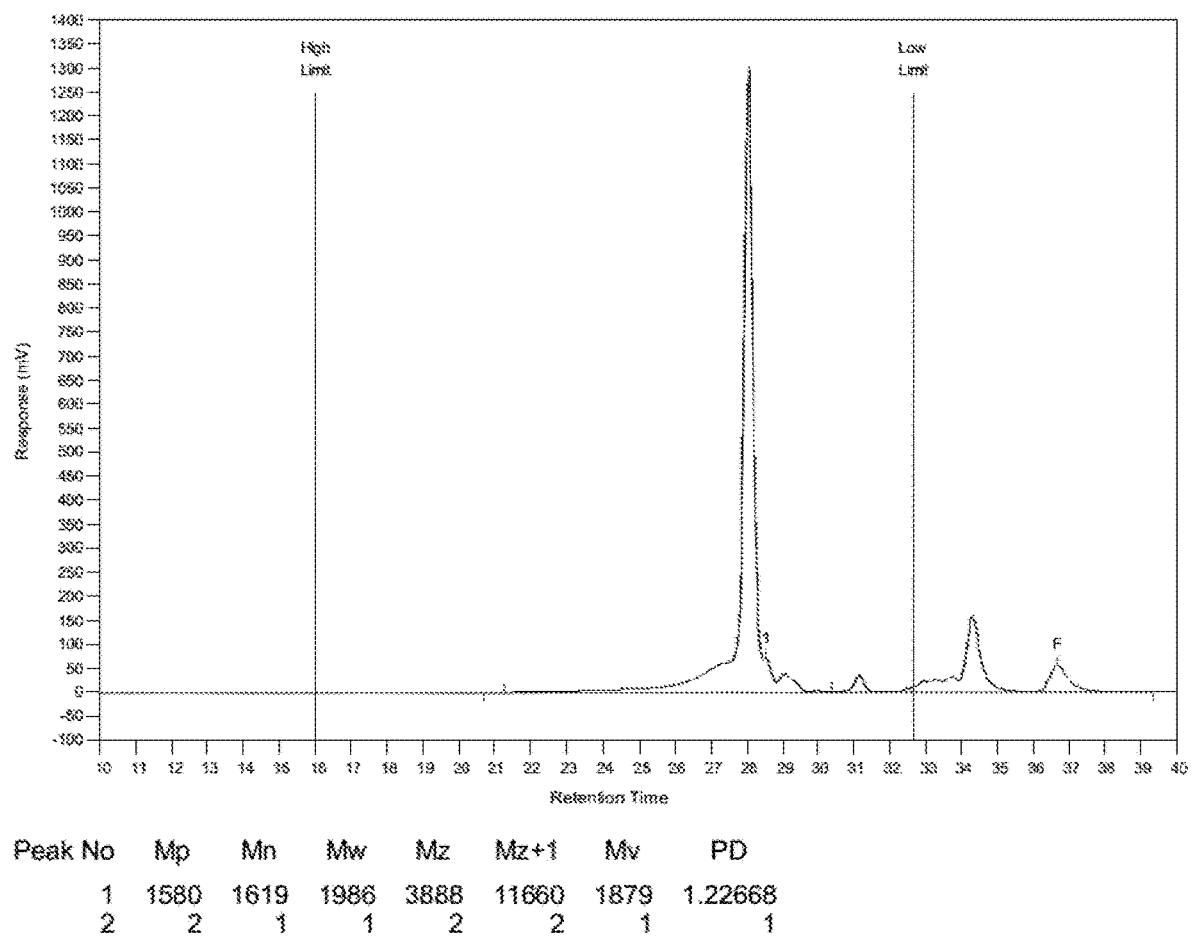
FIG. 9 shows the GPC results of the crude reaction mass prepared from Example 5.

The GPC results of the crude reaction mass are shown in FIG. 9. Theoretically, the solid content of the crude reaction mass was calculated to be 60.85 wt % (assuming all water from formaldehyde solution and produced from the reaction were removed; and all excess formaldehyde was removed). The crude reaction mass contained 1.4 wt % free PTOP (which corresponds to 3.8 g or 2.4 mol % of unreacted PTOP).

Figure 10:
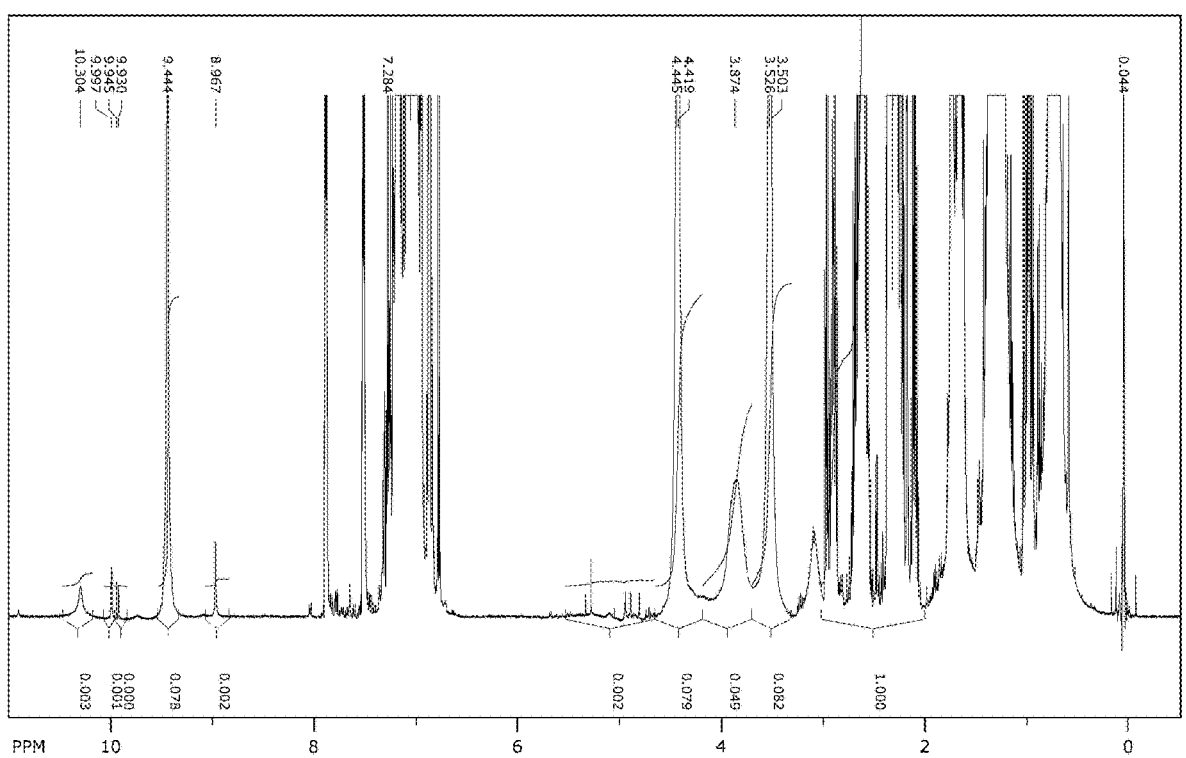
FIG. 10 shows the $^1$H-NMR results of the crude reaction mass prepared from Example 5.

The $^1$H-NMR results of the crude reaction mass are shown in FIG. 10. The yields of the cyclic phenolic resins were determined by further analysis of the $^1$H-NMR results of the crude reaction mass, using the calculation methodology discussed in Example 1. It was understood that the $^1$H-NMR does not allow the quantification of the free monomer content; but the GPC results of the final reaction mass display all components in the reaction mass (with their respective resonances at the picked wavelength (here 280 nm)).

The analysis results of the $^1$H-NMR in FIG. 10 are as follows.

| | |
|---|---|
| Integrals for calixarene phenolic OH protons (for all calixarenes) | 0.084 |
| Integrals for two protons of all methylene bridges (cyclic and linear resins) | 0.210 |
| Integrals for one proton of all methylene bridges (cyclic and linear resins) | 0.105 |
| Ratio of calixarene phenolic OH protons to the protons of all methylene bridges | 0.084/0.105 = 80.0% |

Taking into account the 2.4 mol % unreacted PTOP in the yield calculation (i.e., 97.6 mol % of the PTOP had reacted) resulted in a crude calixarene yield of 78.1% (i.e., 80.0%× 0.976). That is to say, the theoretical yield of all cyclic components in this crude reaction mass was 78.1%.

Applying the same calculation for the tert-octylcalix[8] arene provided the following results.

| | |
|---|---|
| Integrals for tert-octylcalix[8]arene phenolic OH protons | 0.078 |
| Integrals for two protons of all methylene bridges (cyclic and linear resins) | 0.210 |
| Integrals for one proton of all methylene bridges (cyclic and linear resins) | 0.105 |
| Ratio of tert-octylcalix[8]arene phenolic OH protons to the protons of all methylene bridges | 0.078/0.105 = 74.3% |

Taking into account the 2.4 mol % unreacted PTOP in the yield calculation resulted in a crude tert-octylcalix[8]arene yield of 72.5% (i.e., 74.3%×0.976). That is to say, the theoretical yield of tert-octylcalix[8]arene in this crude reaction mass was 72.5%.

This crude reaction mass obtained above was then cooled to about 80° C., and was easily filtered through a Buechner funnel. The filter cake was successively washed with three portions of A-150 (a total of 452.3 g), and dried in the vacuum oven to result in a product tert-octylcalix[8]arene in an isolated yield of 64.6% (theoretical yield), with an HPLC purity of 98.9% (area % at 281 nm), and less than 0.05 wt % free PTOP and 0.13 wt % A-150.

Example 6. Synthesis of Tert-Butylcalix[8]Arene Using Tetramethylammoniumhydroxide (TMAOH) as the Catalyst in Diphenylether

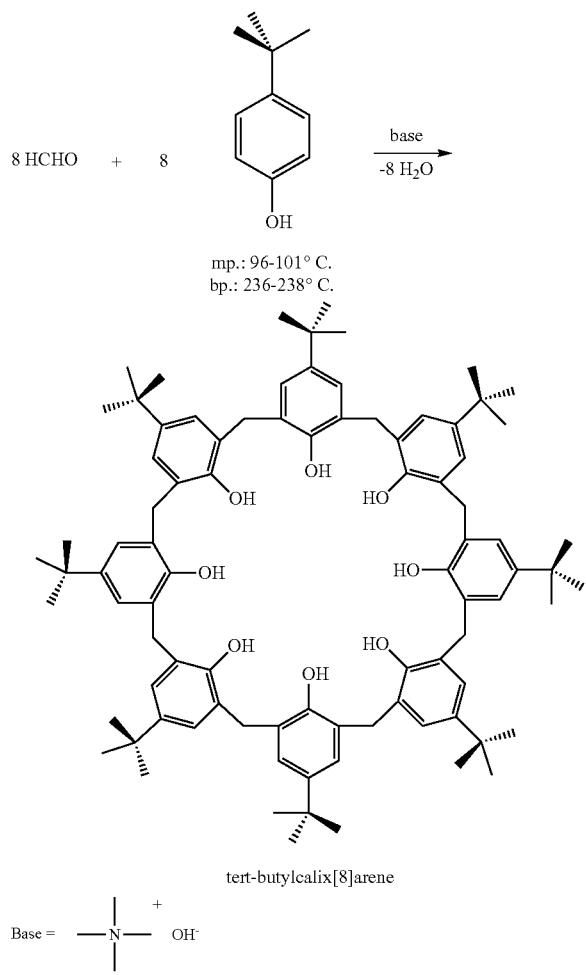

A 500 ml round bottom flask, equipped with an overhead stirrer, thermocouple (having a gas inlet, through which nitrogen stream can be applied), and condenser was loaded with 112.34 g PTBP briquettes (0.75 mol) and 108.25 g diphenylether. A gentle nitrogen flow was on the surface of the hot reaction mass and the reactor was heated to about 80° C. within 20 minutes. Mixing was set to 200 rpm. Five minutes later, when all the PTBP and diphenylether formed a clear solution, 5.5 g TMAOH solution (25% in methanol, 0.015 mol) was added dropwise through addition funnel at a temperature of 89° C. The reaction mixture was heated to 90° C. and 49.7 g of 50 wt % formaldehyde solution (0.83 mol) was added through the addition funnel within 30 minutes, while the formaldehyde solution was heated periodically with a heat gun to prevent formaldehyde from solidification.

Fifteen minutes after the end of the formaldehyde addition, the temperature was increased to 100° C., the nitrogen flow was decreased while the circulating cooling water flow was increased to combat extra moisture in the condenser, and the conditions were held for 12 hours. At the end of the reflux, the reaction mass was about 100° C.

The condenser was then exchanged against a Dean-Stark trap which was left empty. The condenser was placed on top of the Dean-Stark trap, the temperature target was set to 110° C., and the stirring speed was set to 200 rpm. The heating was then started to remove the water. The reactor temperature reached 111° C. after 72 minutes, and 140.6 g more diphenylether was added to the reactor. A 21.2 g water layer was removed from the side arm of the Dean-Stark trap seven minutes later. The reaction mass was then heated to 120° C. and, after an additional forty minutes, to 130° C. The reaction mass became foamy and the heating blanket, which was covering the upper parts of the flask, was loosened. This foam was likely from the dissolved water in diphenylether, which evaporated 25 minutes later, and the heating was increased to 135° C. The nitrogen stream over the surface of the reaction mass was slightly enhanced to facilitate further water removal. Two hours later, the temperature was increased to 140° C. and continued for 1.5 more hours, until a total of 35.06 g of the lower layer was removed (theoretically, the lower layer should be 43.3 g). The distillation was resumed at 140° C. and subsequently increased to 160° C. over the course of 7 hours. Only 0.97 g more distillate was obtained (a total of 36.03 g). The crude reaction mass contained 1.13 wt % free PTBP.

Figure 11:
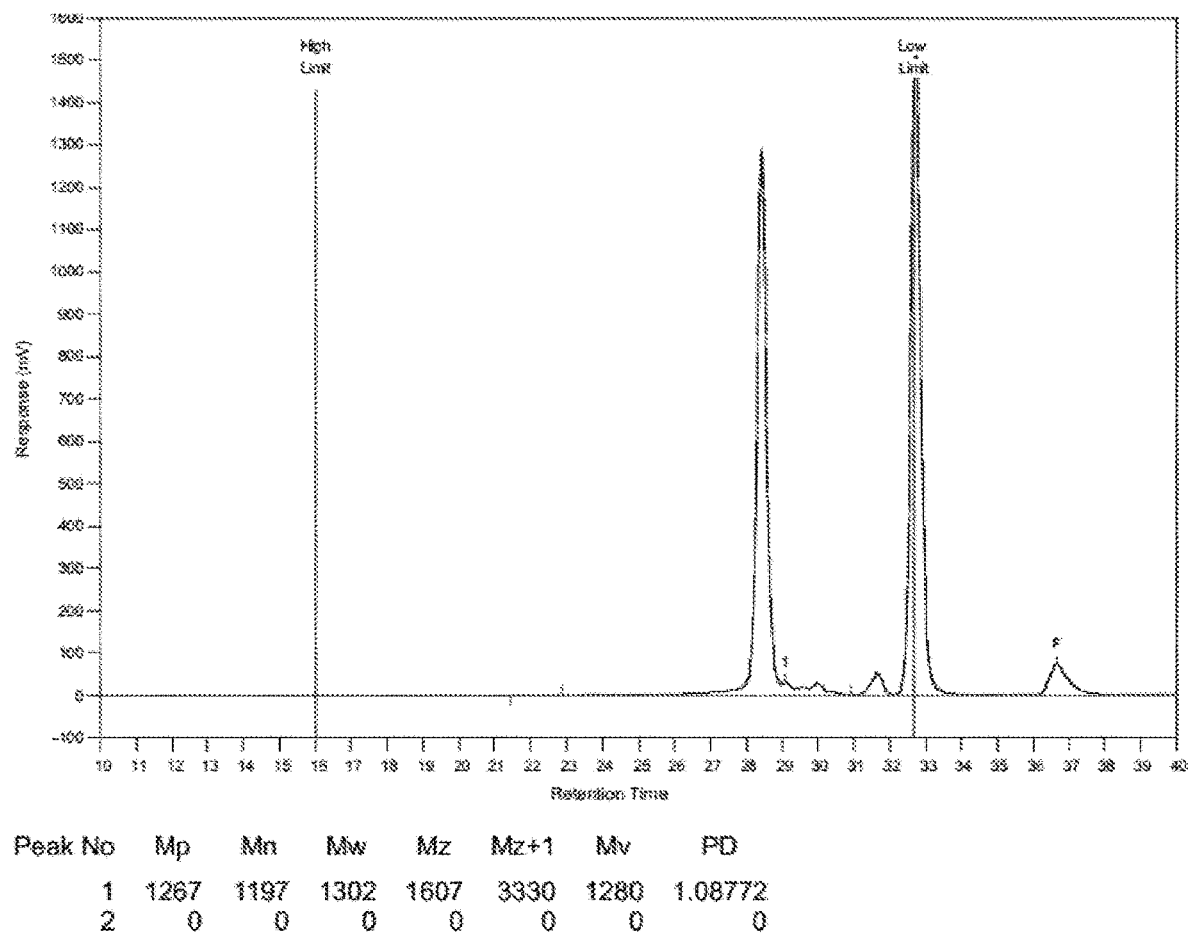
FIG. 11 shows the GPC results of the crude reaction mass prepared from Example 6.

The GPC results of the crude reaction mass are shown in FIG. 11. Theoretically, the solid content of the crude reaction mass was calculated to be 32.65 wt % (assuming all water from formaldehyde solution and produced from the reaction were removed; and all excess formaldehyde was removed). The crude reaction mass contained 1.13 wt % free PTBP (which corresponds to 4.15 g or 3.7 mol % of unreacted PTBP.

Figure 12:
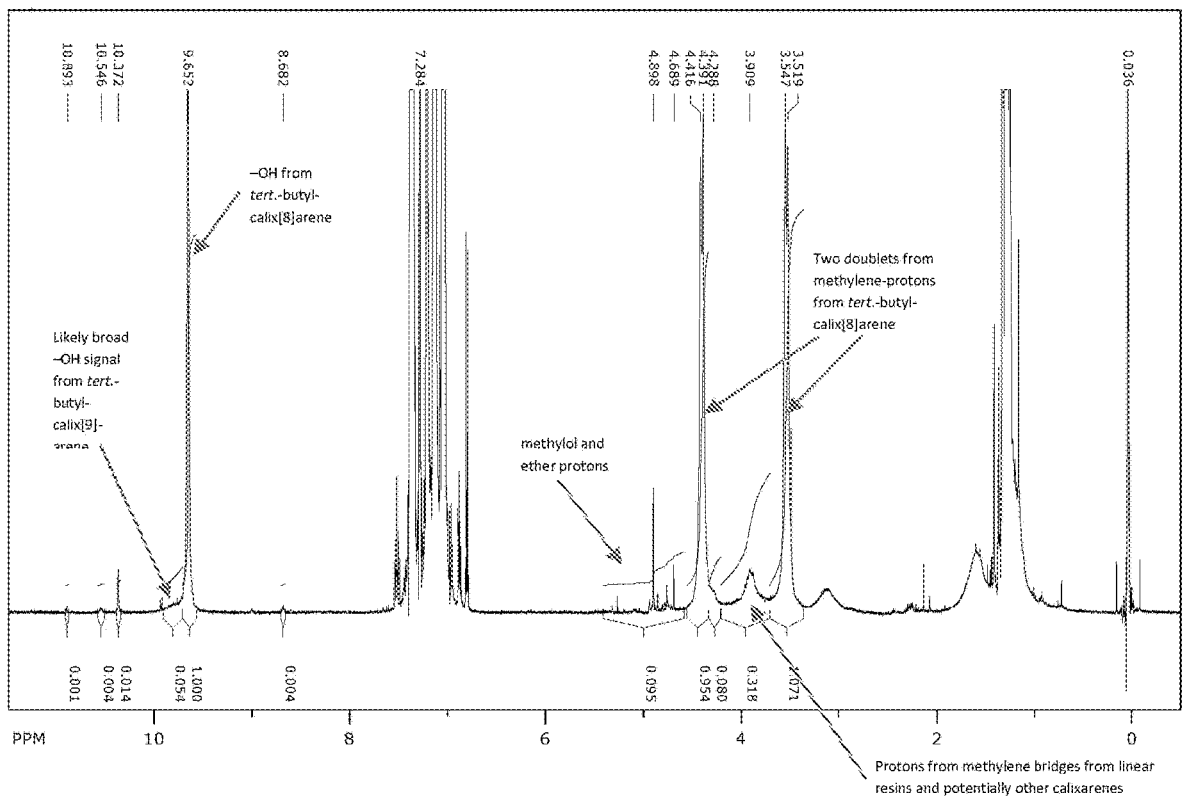
FIG. 12 shows the $^1$H-NMR results of the crude reaction mass prepared from Example 6.

The $^1$H-NMR results of the crude reaction mass are shown in FIG. 12. The yields of the cyclic phenolic resins were determined by further analysis of the $^1$H-NMR results of the crude reaction mass, using the calculation methodology discussed in Example 1. It was understood that the $^1$H-NMR does not allow the quantification of the free monomer content; but the GPC results of the final reaction mass display all components in the reaction mass (with their respective resonances at the picked wavelength (here 280 nm)).

The analysis results of the $^1$H-NMR in FIG. 12 are as follows.

| | |
|---|---|
| Integrals for calixarene phenolic OH protons (for all calixarenes) | 1.077 |
| Integrals for two protons of all methylene bridges (cyclic and linear resins) | 2.423 |
| Integrals for one proton of all methylene bridges (cyclic and linear resins) | 1.2115 |
| Ratio of calixarene phenolic OH protons to the protons of all methylene bridges | 1.077/1.2115 = 88.9% |

Taking into account the 3.7 mol % unreacted PTBP in the yield calculation (i.e., 96.3 mol % of the PTBP had reacted) resulted in a crude calixarene yield of 85.6% (i.e., 88.9%× 0.963). That is to say, the theoretical yield of all cyclic components in this crude reaction mass was 85.6%.

Applying the same calculation for the tert-butylcalix[8] arene provided the following results.

| | |
|---|---|
| Integrals for tert-butylcalix[8]arene* phenolic OH protons | 1.054 |
| Integrals for two protons of all methylene bridges (cyclic and linear resins) | 2.423 |
| Integrals for one proton of all methylene bridges (cyclic and linear resins) | 1.2115 |
| Ratio of tert-butylcalix[8]arene phenolic OH protons to the protons of all methylene bridges | 1.054/1.2115 = 87.0% |

*As shown in the HPLC analysis below, a small amount of tert-butylcalix[9]arene side product presented in this sample. Thus, the $^1$H-NMR peaks for tert-butylcalix[8]arene presumably also included tert-butylcalix[9]arene.

Taking into account the 3.7 mol % unreacted PTBP in the yield calculation resulted in a crude tert-butylcalix[8]arene yield of 83.8% (i.e., 87.0%×0.963). That is to say, the theoretical yield of tert-butylcalix[8]arene in this crude reaction mass was 83.8%. This is close to the actual isolated yield of 84.2%.

This crude reaction mass obtained above was then cooled down and was easily filtered through a Buechner funnel. The filter cake was successively washed with three portions of ethylacetate (100 g each portion). After drying, a white filter cake was obtained, showing the following compositions: 0.12 wt % PTBP, 4.81 wt % diphenylether and 0.18 wt % ethylacetate. The HPLC analysis (which did not account for solvents and unreacted alkylphenols) showed a purity of 92.3% (area % at 281 nm) of tert-butylcalix[8]arene and 5.14% (area % at 281 nm) of a side product believed to be tert-butylcalix[9]arene. The isolated yield was 84.2%.

Example 7. Synthesis of Tert-Butylcalix[8]Arene Using DBU as the Catalyst—Kinetic Mechanism for the Reaction Described in Example 1

A 2 L round bottom flask, equipped with an overhead stirrer, thermocouple (having a gas inlet, through which nitrogen stream can be applied), and condenser, was loaded with 550.2 g PTBP briquettes (3.66 mol) and 367.0 g A-150 (Solvesso™ 150 Fluid). A gentle nitrogen flow was applied on the surface of the hot reaction mass and the reactor was heated to about 80° C. within 20 minutes. Mixing was set to 112 rpm. Five minutes later, when all the PTBP and A-150 formed a clear solution, 8.6 g DBU (98%, 0.056 mol) was added dropwise at a temperature of 81° C., and a slight exotherm was observed. The reaction mixture was heated to 85° C. and 220 g of 50 wt % formaldehyde solution (3.66 mol) was added within 1 hour and 20 minutes, while the formaldehyde solution was heated periodically with a heat gun to prevent formaldehyde from solidification.

After the formaldehyde addition, the temperature was increased to 90° C., the nitrogen flow was decreased while the circulating cooling water flow was increased to combat extra moisture in the condenser, and the conditions were held for 30 minutes. A formaldehyde trap was placed under the condenser, with the arm to the trap wrapped with aluminum foil, and was heated to reflux at 100° C. about 40 minutes after the formaldehyde addition. The heating of the reaction mixture continued and the total reflux time was 15.25 hours at a temperature of about 100-105° C. (under reflux). At various points of the reflux stage, samples of the reaction mass were taken to evaluate the content of free formaldehyde: a sample taken after heating for about two more hours at 102° C. showed 3.0% free formaldehyde; a sample taken after additional heating for about two more hours at 102° C. and about 25 minutes at 103° C. showed 3.0% free formaldehyde; a sample taken after additional heating for about 35 minutes at 102-103° C. and about 7.5 hours at 102-105° C. showed 2.3% free formaldehyde; and a final sample taken after additional heating for about 2 hours at 102-105° C. showed 2.5% free formaldehyde.

The heating was switched off and the formaldehyde trap was exchanged against a Dean-Stark trap which was filled with A-150. The condenser was placed on top of the Dean-Stark trap and the heating was resumed to remove the water in the reaction system. Fifty seven minutes after the reflux ended, the heating was set to 115° C. and 54.5 g additional A-150 was added to the reaction flask, and the temperature was further increased. One hundred and twenty minutes after the reflux ended, a total of 128.9 g water layer was removed and the reaction temperature reached 145.3° C. The distillation was continued while the temperature was kept at about 145° C. The reaction mass became thicker and thicker. At the end of distillation, the highly viscous reaction mass was poured into glass jars. A final total lower distillate layer (water layer) of 167.2 g was observed. The total distillation time was 6.5 hours. At various points of the distillation stage, samples of the reaction mass were taken to evaluate the composition of the reaction product, in particular the content of tert-butylcalix[8]arene. The first sample (t0) was taken 22 minutes after the reflux ended. The second sample (t1) was taken after a total of 42 g water layer was removed. The third sample (t2) was taken after a total of 88 g water layer was removed. The fourth sample (t3) was taken after a total of 128.9 g water layer was removed. The next few samples were taken hourly after the temperature reached 145° C.: t4 at the first hour, t5 at the second hour, t6 at the third hour, and t7 at the fourth hour. A final sample (tF) was taken when the heating was switched off.

Figure 13:
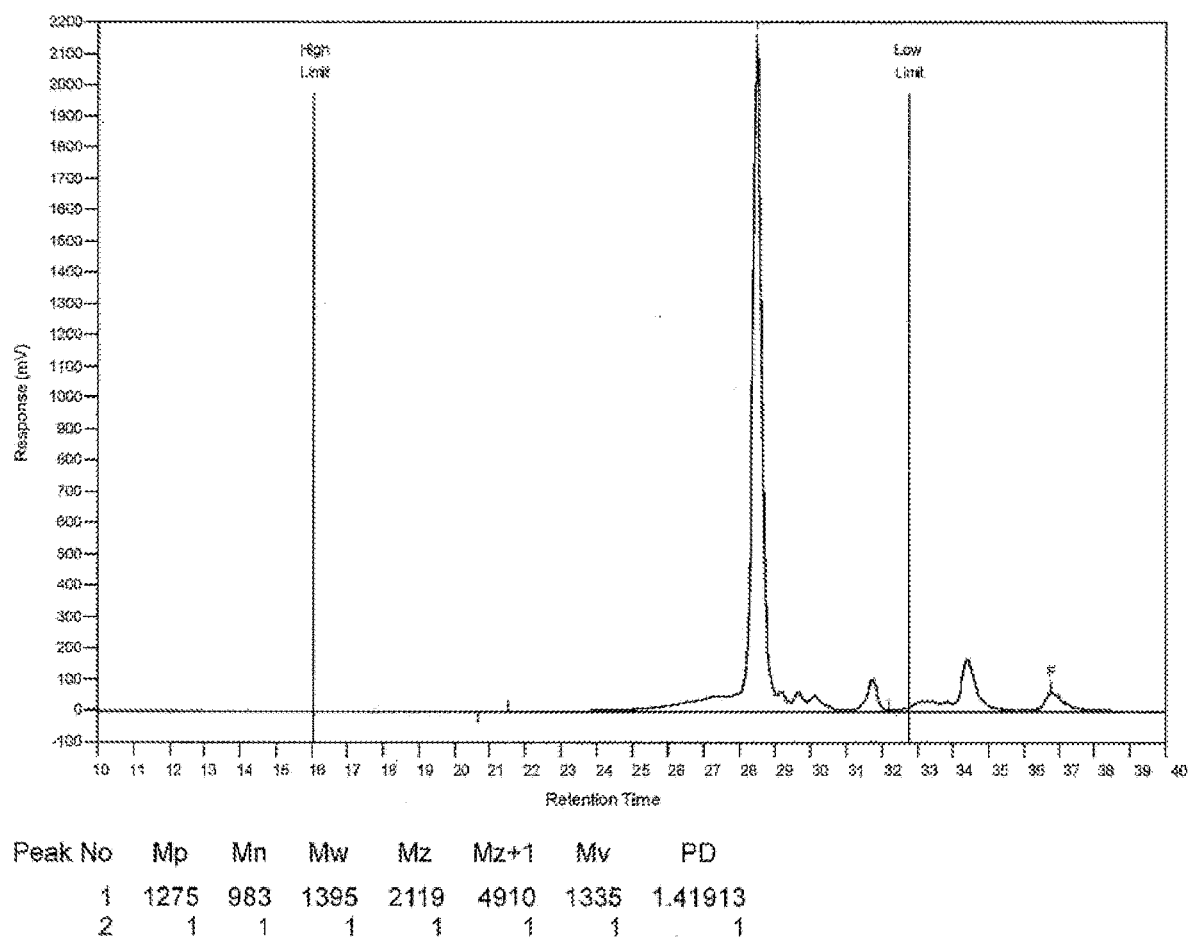
FIG. 13 shows the GPC results of the final reaction mass taken from the final sample (tF) prepared from Example 7.

The GPC results (Mw=1395) of the final reaction mass (taken from the final sample, tF) are shown in FIG. 13. FIG. 13 shows that the reaction product had a very lean and sharp peak. The final reaction mass contained 2.36% free PTBP and less than 15 ppm free formaldehyde.

Table 1 lists the $^1$H-NMR results for the samples of the reaction mass at various distillation stages and temperatures. The $^1$H-NMR features of the tert-butylphenol-derived calixarenes from ring size 4 to ring size 16, such as the proton signals of the methylene bridges and of the phenolic hydroxyls in CDCl$_3$, have been discussed in an article entitled "Isolation, Characterization, and Conformational Characteristics of p-tert-butylcalix[9-20]arenes" by Stewart et al. published on *J. Am. Chem. Soc.* 121: 4136-46 (1999) ("Stewart"), which is hereby incorporated by reference in its entirety, to the extent not inconsistent with the subject matter of this disclosure. That article shows that only tert-butylcalix[4]arenes and tert-butylcalix[8]arenes display a set of two doublets (at 20° C.) for their methylene bridges; and they show different resonances for the phenolic OH groups (at 20° C.): tert-butylcalix[4]arene has a resonance at about 10.4 ppm while tert-butylcalix[8]arene displays it at about 9.6 ppm.

Figure 14A:
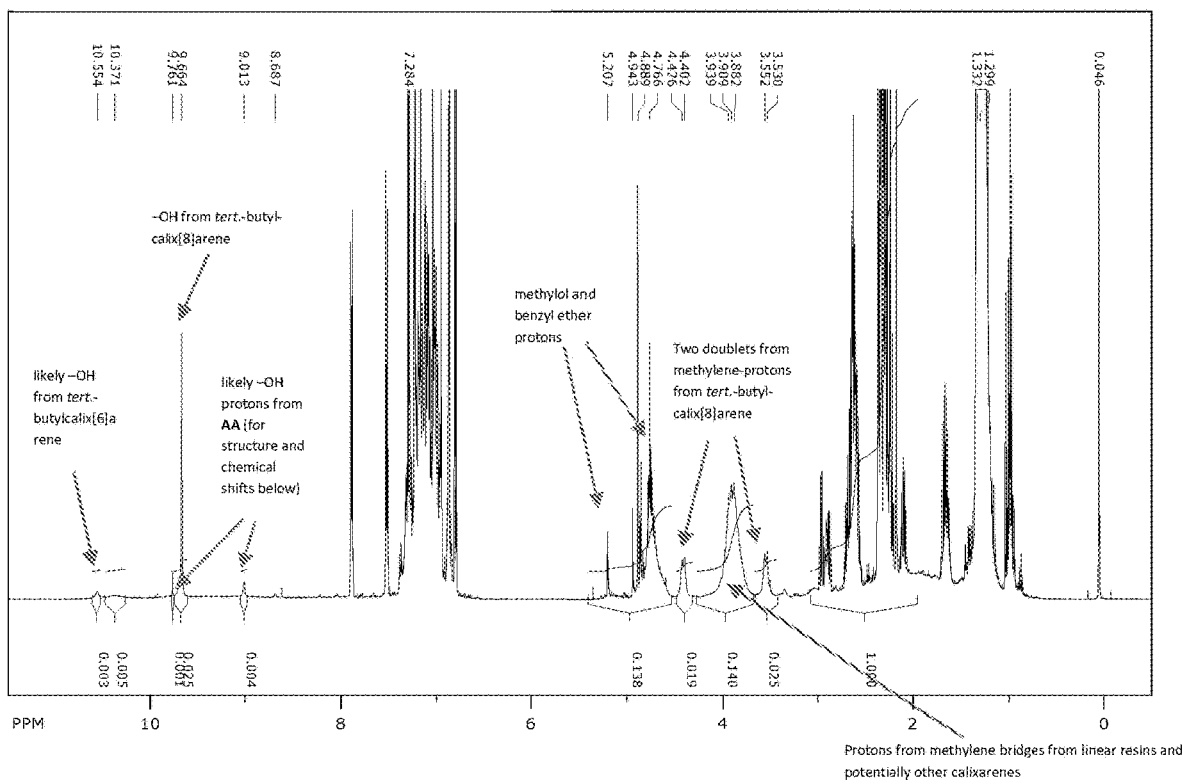
FIG. 14A shows the $^1$H-NMR results of the reaction mass taken from sample t0 prepared from Example 7.
Figure 14B:
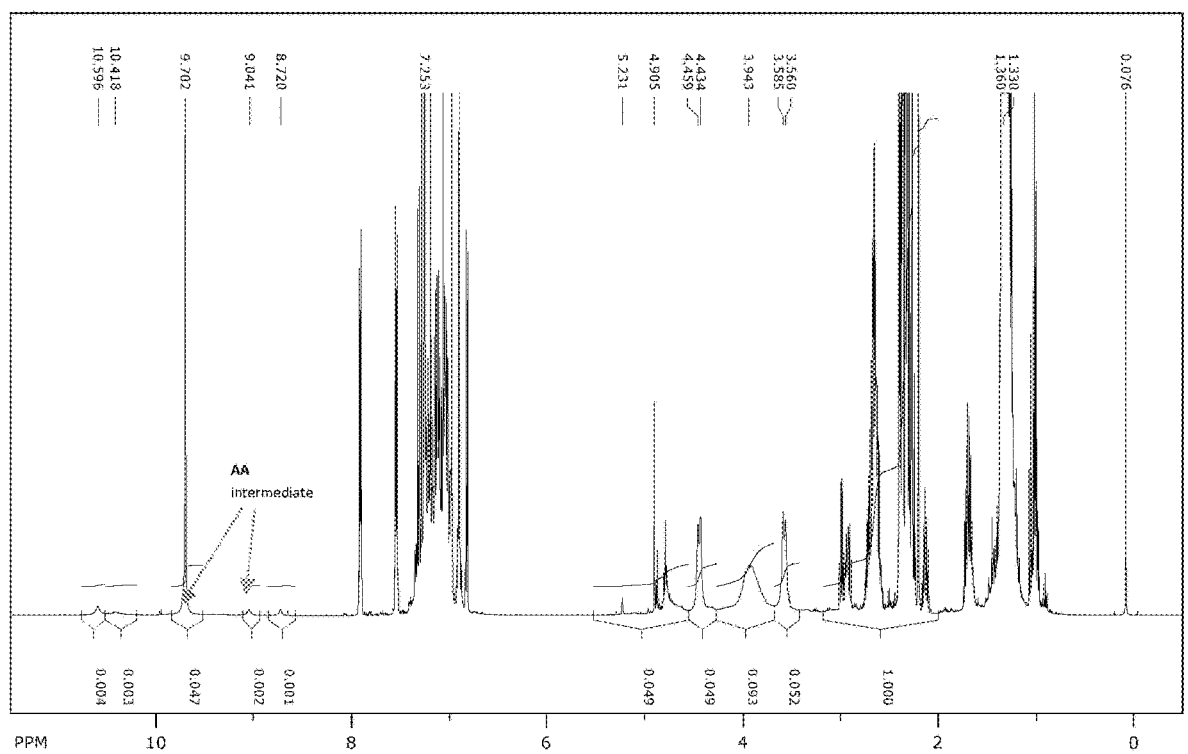
FIG. 14B shows the $^1$H-NMR results of the reaction mass taken from sample t4 prepared from Example 7.
Figure 14C:
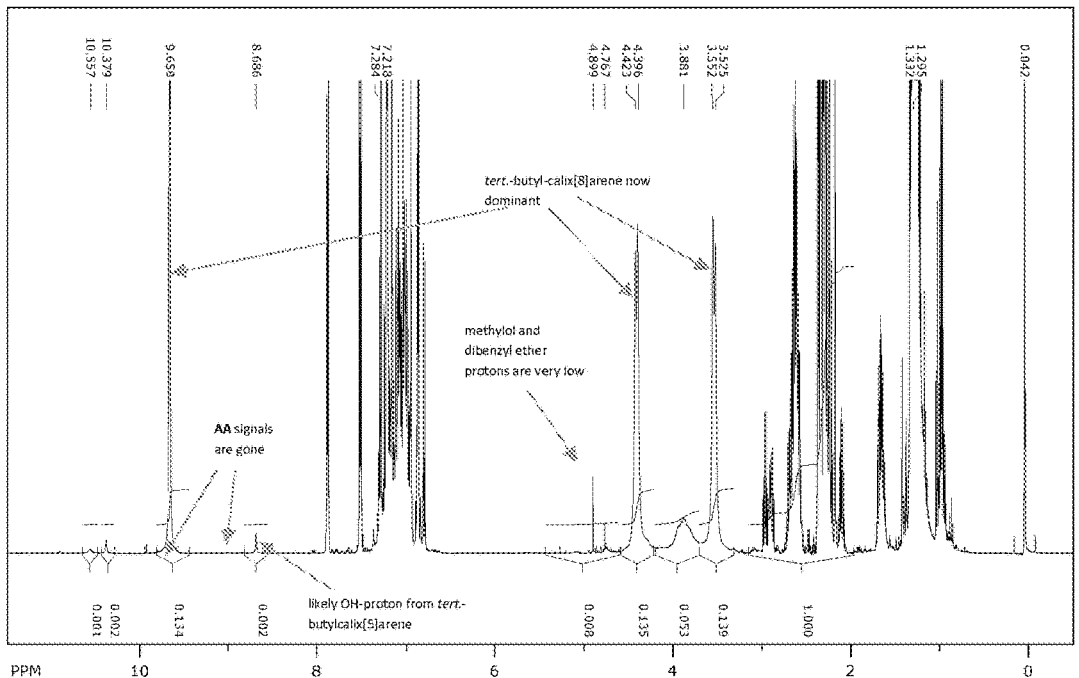
FIG. 14C shows the $^1$H-NMR results of the final reaction mass taken from the final sample (tF) prepared from Example 7.

The $^1$H-NMR results of a few samples of the reaction mass at various distillation stages and temperatures are shown in FIGS. 14A-14C for illustrative purposes. For instance, FIG. 14A shows that in sample t0, taken at the end of the reflux and the beginning of the water removal phase, only 13.9% of all resin components had turned into tert-butylcalix[6 & 8]arenes (the value was taken from the integrals of the phenolic hydroxyl protons of tert-butylcalix[6 & 8]arene (respectively one methylene proton of tert-butylcalix[8]arene) divided by all protons coming from the reaction with formaldehyde—calculated here by adding the values of the second column and the ninth column, and dividing by the value of the fourth column: (0.019+0.003)/0.158), as shown in Table 1). As shown in Table 1, at this point of the reaction, the selectivity between calix[8]arene and calix[6]arene is not yet great (relative ratio between integrals of tert-butyl calix[6]arene and calix[8]arenes hydroxyl protons is 10.7% (neglecting integration error coming from AA)). As shown in Table 1, the selectivity toward the tert-butylcalix[8]arene developed during the six hours of water removal step, i.e., relative ratio between integrals of tert-butyl calix[6]arene and calix[8]arenes went from 10.7% at 0 hour of distillation to 3.4% after 3-4 hours of distillation, and to 1.3% after 5-6 hours of distillation.

Figure 15:
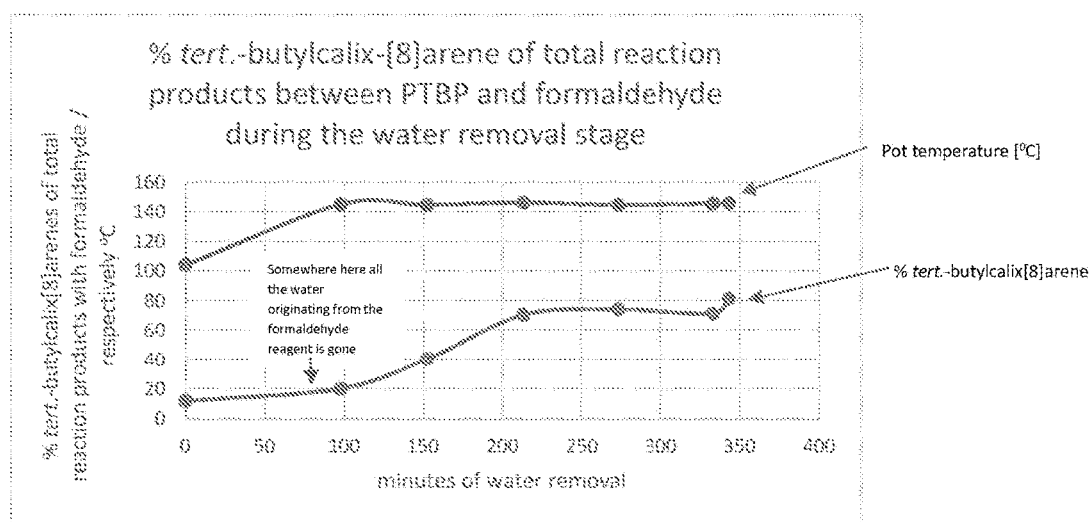
FIG. 15 shows the plot of % tert-butylcalix[8]arene of total reaction products and the reactor temperature against the time of the water removal, during the distillation stage in Example 7.

FIG. 15 plots the data taken from Table 1, particularly, % tert-butylcalix [8]arene of total reaction products and the reactor temperature against the time of the water removal, showing the kinetics during the water removal phase for the formation of tert-butylcalix[8]arene.

An intermediate, denoted as

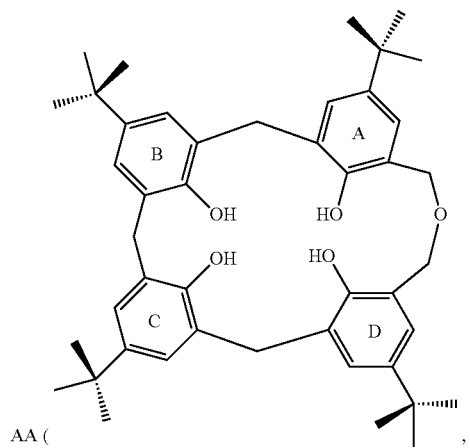

AA ( 7,13,19,25-tetra-tert-butyl-27,28,29,20-tetrahydroxy-2,3-bishomo-3-oxacalix[4]arene; $^1$H-NMR (CDCl$_3$): 9.60 ppm (2 OH on ring B and C), 8.92 ppm (2 OH on ring A and D); see Gutsche et al., "Calixarenes. 4. The synthesis, characterization, and properties of the calixarenes from p-tert-butylphenol, *J. Am. Chem. Soc.* 103: 3782-92 (1981), which is hereby incorporated by reference in its entirety, to the extent not inconsistent with the subject matter of this disclosure) was present in the $^1$H-NMR of the sample Nos. t0-t5, and was present in a trace amount in the $^1$H-NMR of the sample No. t6, but was not observed in the $^1$H-NMR of the sample No. tF, i.e., the analytical data shows that the final reaction product after 6.5 hours of water removal did not contain this reaction intermediate.

A column chromatography was conducted on the final reaction mass, to separate the calixarene from the linear resins to assess the purity of the obtained cyclics by means of HPLC (the cyclic compounds need to be separated from the linear resin to avoid interfering with each other on the HPLC column), and to calculate the yield of the calixarene compounds.

Briefly, 0.774 g of sample tF was dissolved in chloroform and placed on a chromatography column (12 g, Aldrich, high purity grade, pore size 60 Å, 200-400 mesh particle size). The sample was eluted with chloroform initially and followed by a mixed solvent of acetone:methanol:chloroform (1:1:1 by volume). In the initial fractions, the cyclic compounds ran through (the isolated cyclic sample tC) while the linear compounds remained on top. The switch to the mixed solvent then eluted the linear partition through the column. The chromatographic separation was controlled via TLC plates (coated with UV absorbance) and then the respective fractions were combined and concentrated to dryness at the Rotavap (final conditions: 1 mbar, 50° C., for 30 minutes).

The solid content of the final calixarene reaction mass tF was determined to be 68.2% (~1 g sample, 200° C. for 30 minutes).

Figure 16A:
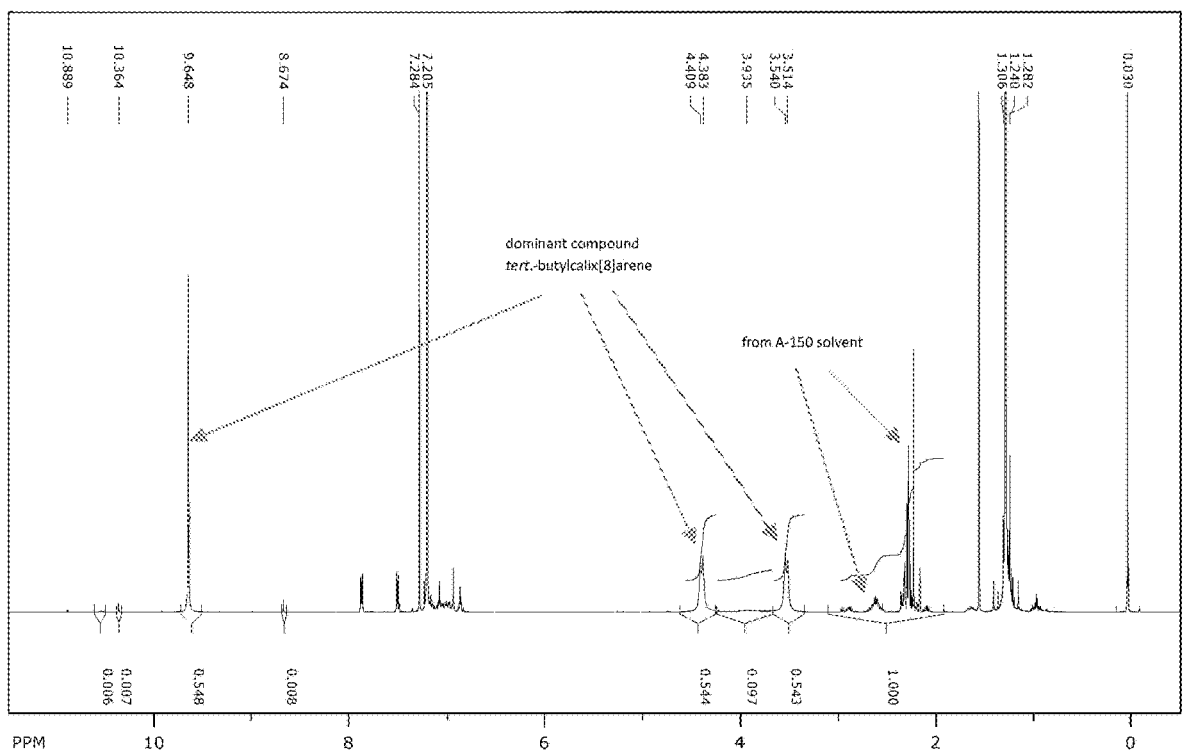
FIG. 16A shows the $^1$H-NMR results of the cyclic components of the final reaction mass after column chromatography (sample tC), prepared from Example 7.

The $^1$H-NMR results for the cyclic sample tC are shown in FIG. 16A. The results are also summarized in Table 1.

Figure 16B:
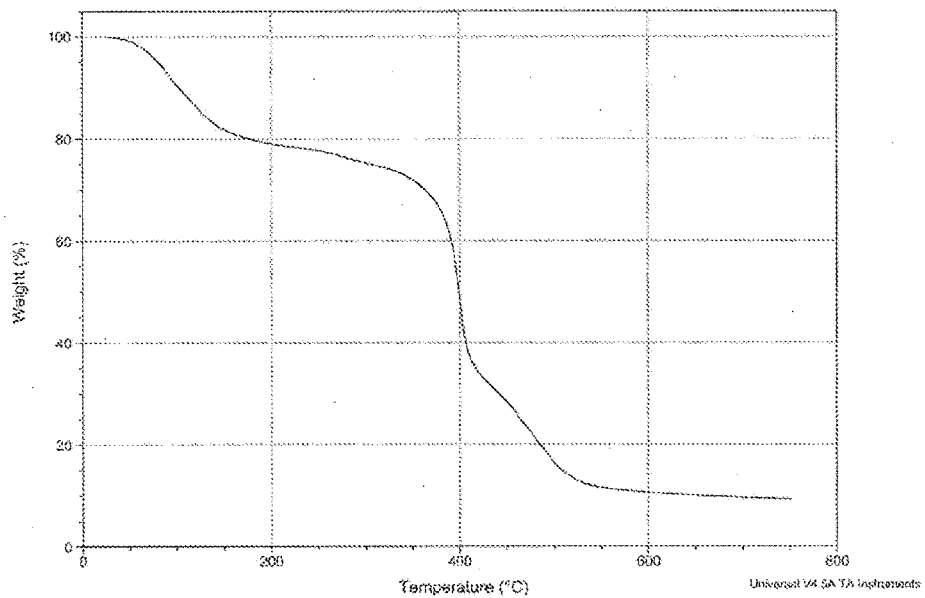
FIG. 16B shows the TGA results of the cyclic components of the final reaction mass after column chromatography (sample tC), prepared from Example 7.

The TGA (TA Instruments model TGA Q50) results for the cyclic sample tC are shown in FIG. 16B. As shown in FIG. 16B, the weight loss until about 180° C. may be due to the loss of the incorporated solvent, for instance, A-150, because calixarenes can incorporate solvents into their solid structures, which sometimes cannot be completely removed easily by means of vacuum and heat. The major loss around 400° C. appeared to be the decomposition of the main calixarene, indicating a high thermal stability of the isolated calixarene compounds.

Figure 16C:
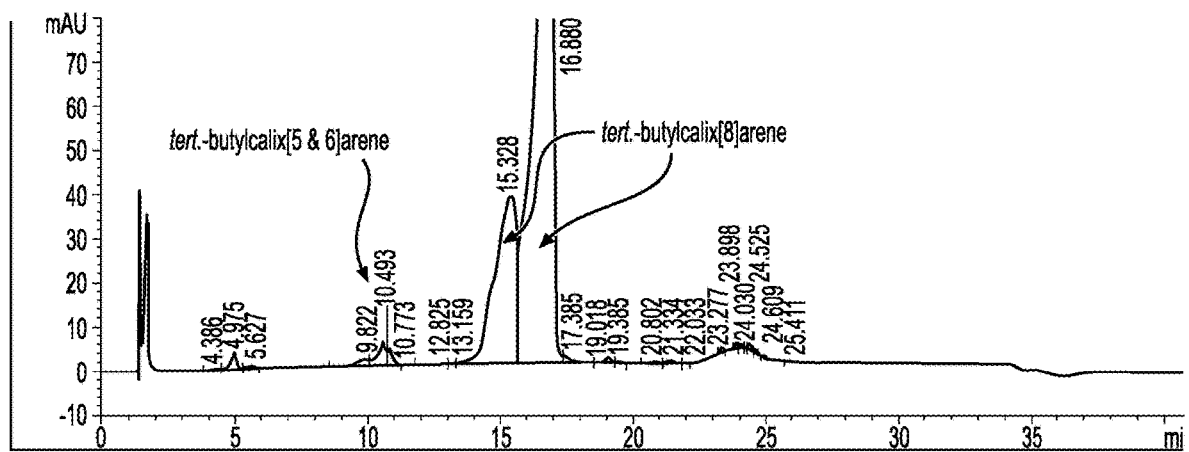
FIG. 16C shows the HPLC results of the cyclic components of the final reaction mass after column chromatography (sample tC), prepared from Example 7.

The HPLC results for the cyclic sample tC are shown in FIG. 16C. It was determined from the GC that sample tC contained 15.2 wt % A-150 solvent. Also, the calculation of peak area from the HPLC indicated that the purity for tert-butylcalix[8]arene (solvent was not integrated) was 95.52%.

Figure 16D:
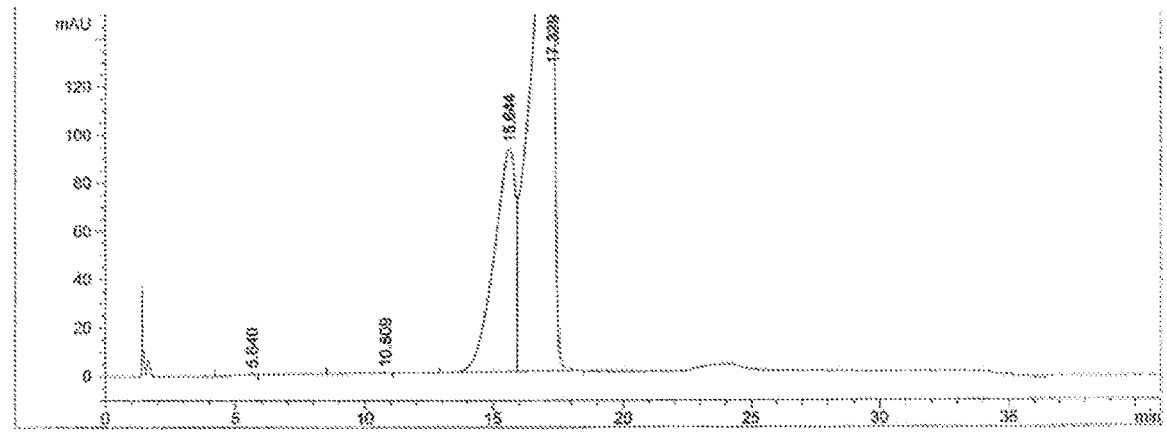
FIG. 16D shows the HPLC results of a commercially available tert-butylcalix[8]arene sample.
Figure 17A:
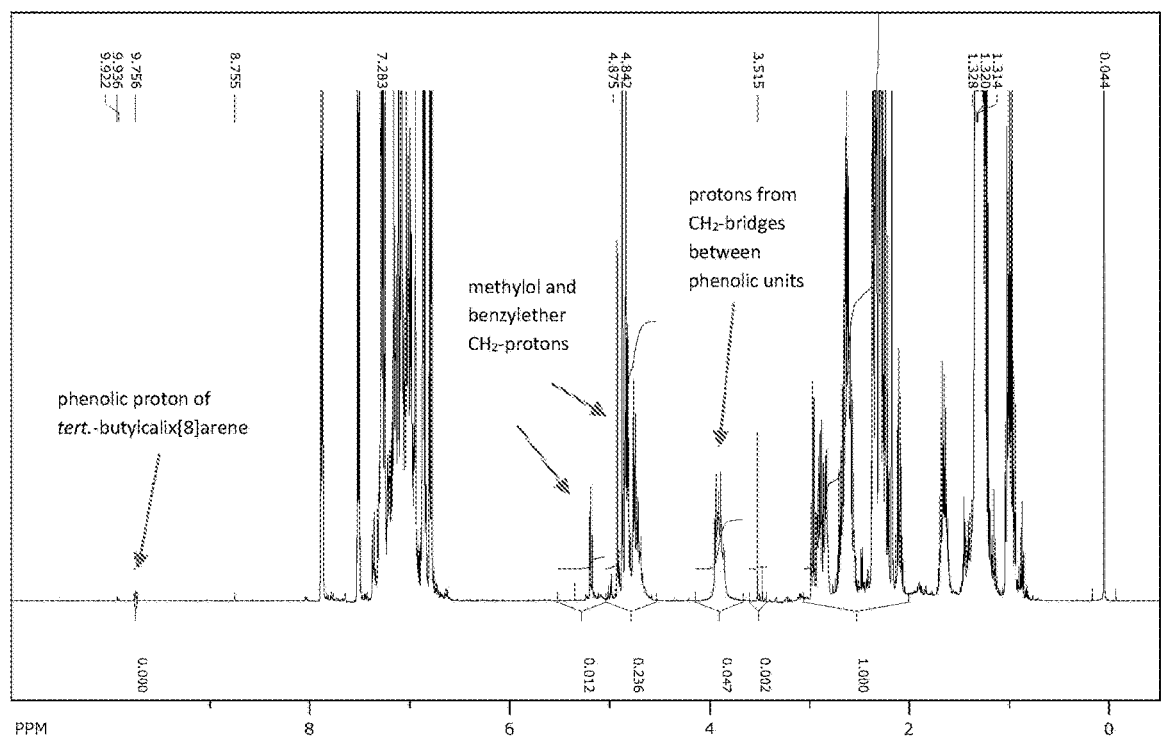
FIG. 17A shows the $^1$H-NMR results of the sample taken from the reaction mass after one hour of reaching reflux, prepared from Example 8.
Figure 17B:
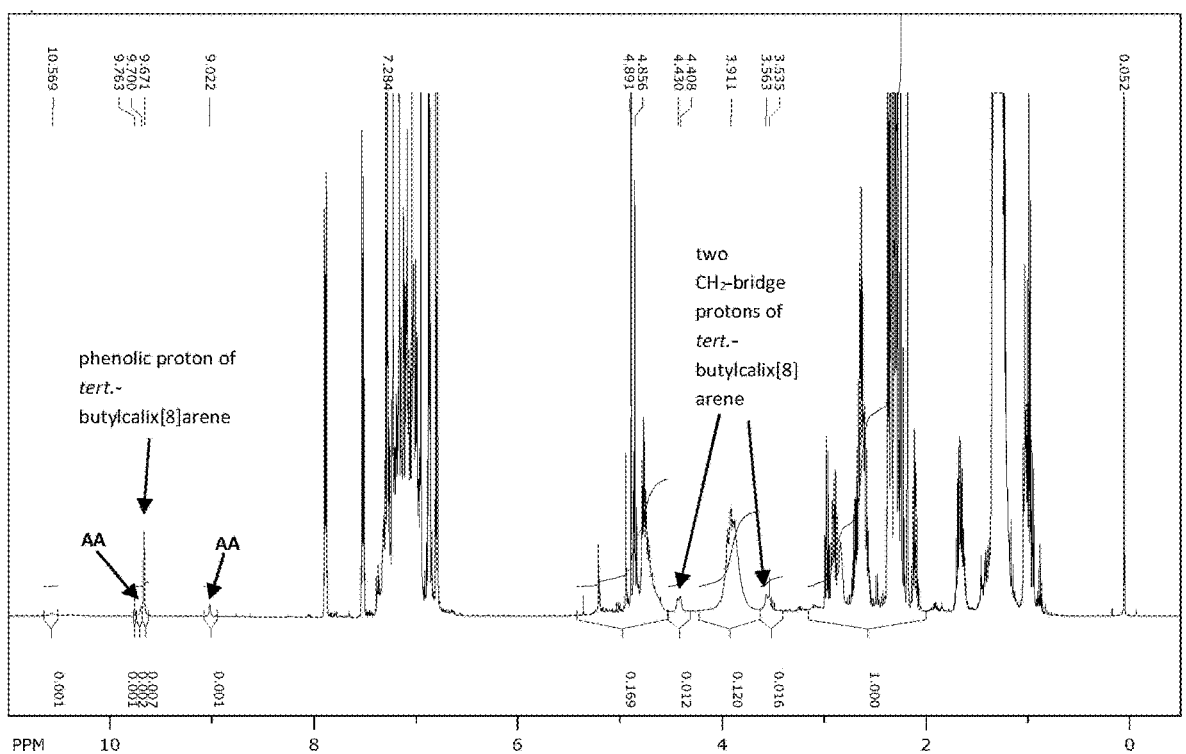
FIG. 17B shows the H-NMR results of the sample taken from the reaction mass after seven hours of reaching reflux, prepared from Example 8.
Figure 17C:
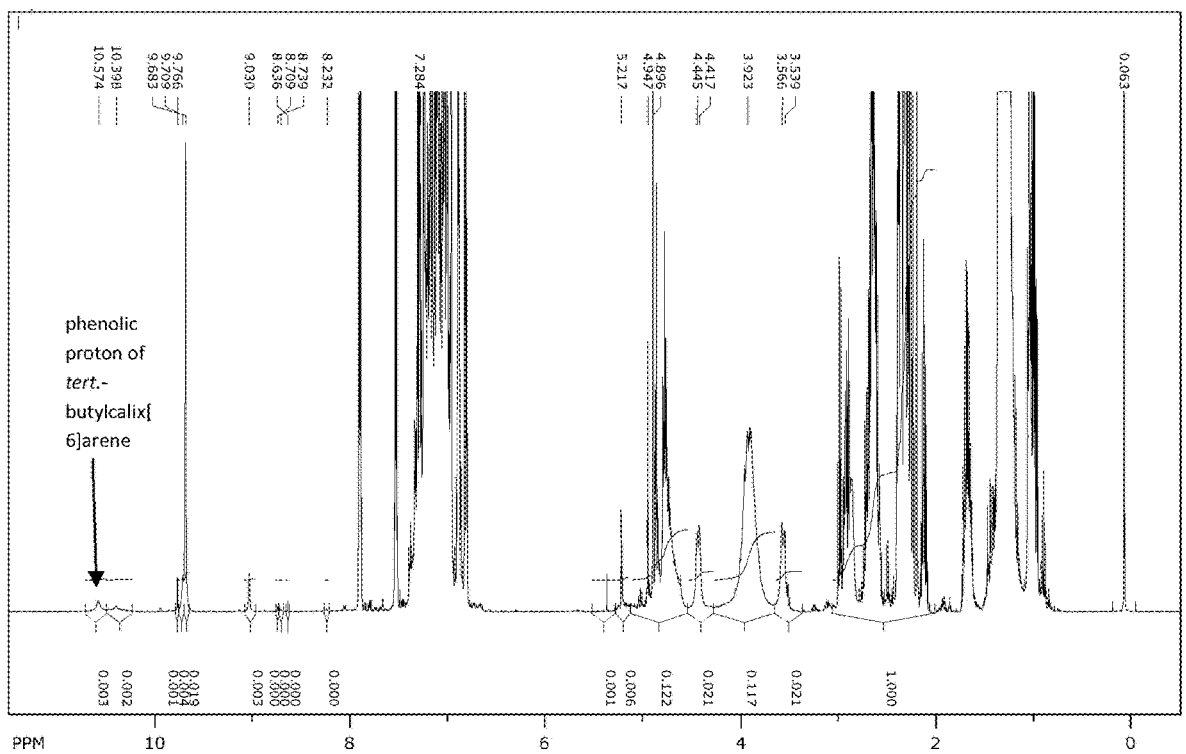
FIG. 17C shows the $^1$H-NMR results of the sample taken from the reaction mass after twelve hours of reaching reflux, prepared from Example 8.
Figure 17D:
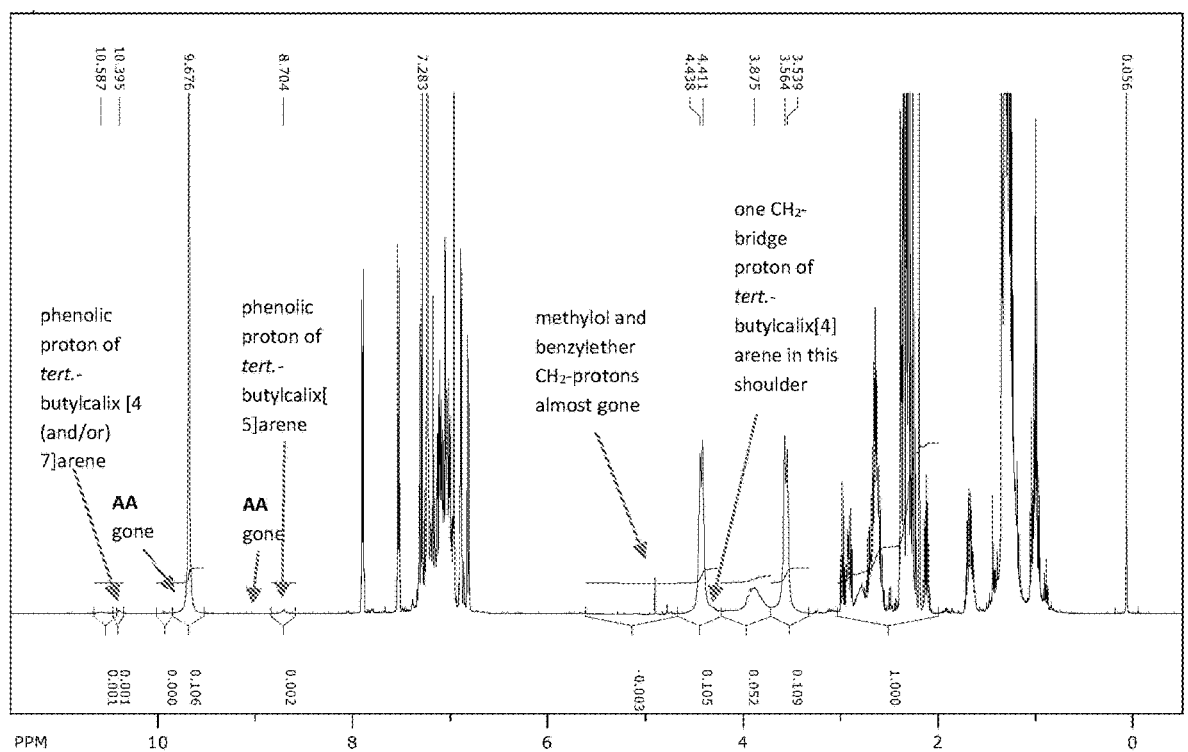
FIG. 17D shows the $^1$H-NMR results of the sample taken from the final reaction mass after the end of reflux and distillation (final), prepared from Example 8.

As a control, the HPLC results for a commercially available tert-butylcalix[8]arene sample are shown in FIG. 16D.

TABLE 1

The $^1$H-NMR results for the samples of the reaction mass at various distillation stages (Example 7)

| Sample No./min after start of water removal [min] | Integrals for one methylene proton, tert-butylcalix[8]arene[a] | Integrals for phenolic OH protons, tert-butylcalix[8]arene[b] | Proton count (4.4 ppm + ½*3.9 ppm + ½ * 4.9 ppm)[c] | % tert-butylcalix[8]arene of total[d] | ° C./g water out[e] | Integrals for two methylene protons, resins and other calixarenes[f] | Integrals for two methylene protons, with —O— substitution[g] | Integrals for phenolic OH protons, tert-butylcalix[6]arene[h] | Relative ratio between integrals of tert-butylcalix[6]arene and tert-butylcalix[8]arene [%] |
|---|---|---|---|---|---|---|---|---|---|
| t0/0 | 0.019 | 0.025[i] | 0.158 | 12.0 | 104.3/— | 0.140 | 0.138 | 0.003 | 10.7 |
| t1/— | 0.198 | 0.186[i] | 1.237 | 16.0 | —/42 | 1.062 | 1.016 | 0.023 | 11.0 |
| t2/— | 0.024 | 0.030[i] | 0.1755 | 13.7 | —/88 | 0.160 | 0.143 | 0.004 | 11.8 |
| t3/98 | 0.033 | 0.035 | 0.161 | 20.5 | 145.3/128.9 | 0.141 | 0.115 | 0.004 | 10.3 |
| t4/153 | 0.049 | 0.047 | 0.120 | 40.8 | 145/135.5 | 0.093 | 0.049 | 0.004 | 7.8 |
| t5/213 | 0.114 | 0.112 | 0.1615 | 70.6 | 146.5/— | 0.069 | 0.026 | 0.004 | 3.4 |
| t6/273 | 0.094 | 0.095 | 0.1265 | 74.3 | 145/— | 0.053 | 0.012 | 0.003 | 3.06 |

TABLE 1-continued

The $^1$H-NMR results for the samples of the reaction mass at various distillation stages (Example 7)

| Sample No./min after start of water removal [min] | Integrals for one methylene proton, tert-butylcalix[8]arene[a] | Integrals for phenolic OH protons, tert-butylcalix[8]arene[b] | Proton count (4.4 ppm + ½*3.9 ppm + ½ * 4.9 ppm)[c] | % tert-butylcalix[8]arene of total[d] | ° C./g water out[e] | Integrals for two methylene protons, resins and other calixarenes[f] | Integrals for two methylene protons, with —O— substitution[g] | Integrals for phenolic OH protons, tert-butylcalix[6]arene[h] | Relative ratio between integrals of tert-butylcalix[6]arene and tert-butylcalix[8]arene [%] |
|---|---|---|---|---|---|---|---|---|---|
| t7/333 | 0.084 | 0.079 | 0.1175 | 71.5 | 146/— | 0.057 | 0.010 | 0.001 | 1.3 |
| tF/343 | 0.135 | 0.134 | 0.1655 | 81.6 | 146/167.2 | 0.053 | 0.008 | 0.001 | 0.74 |
| tC/— | | 0.544 | 0.548 | 0.5925 | 91.8 | | 0.097 | 0 | 0.006 | 1.08 |

[a]Value was taken directly from the NMR spectrum at about 4.4 ppm
[b]Value was taken directly from the NMR spectrum at about 9.66 ppm
[c]Value was taken from the NMR spectrum and calculated using the equation listed in the table; these are all protons coming from the reaction with formaldehyde: methylols, ethers, methylene bridges in linear resins as well as calixarenes. Since tert-butylcalix[8]arene splits the methylene bridge into two clearly distinct signals (and each can be integrated), the area count of the other methylene bridging groups areas are divided into half to account for one of the two protons
[d]The percentage of tert-butylcalix[8]arene of all products resulted in from the reaction with formaldehyde can then be calculated by division of the areas for one proton of tert-butylcalix[8]arene by the total value of one methylene proton of all products resulted in from the reaction with formaldehyde. The value of this column was obtained by dividing the value of the second column by the value of the fourth column. For instance, for "t0," 0.019/0.158 = 12.0%.
[e]The water in the reaction system came from formaldehyde (~110 g water from the formaldehyde loading of this example)
[f]Value was taken directly from the NMR spectrum at about 3.9 ppm
[g]Value was taken directly from the NMR spectrum at about 4.9 ppm
[h]Value was taken directly from the NMR spectrum at about 10.56 ppm
[i]Peak has a tiny, little shoulder (likely from structure AA)

Example 8. Synthesis of Tert-Butylcalix[8]Arene Using TEAOH as the Catalyst—Kinetic Mechanism for the Reaction Described in Example 2

This example discusses the kinetics of the calix[8]arene formation using a sterically hindered tetraalkyl-ammonium hydroxide as the catalyst. The reaction scale was chosen that small sampling sizes of the reaction mass would not significantly impact the kinetic behavior of the total batch. The reaction set up was similar to that of Example 1, with the starting material loading as follows: PTBP: 563 g (3.75 mol, 44.4 wt % of total loading); A-150 (Solvesso™ 150 Fluid): 450 g; 40% aqueous tetraethylammonium hydroxide solution as the catalyst: 30.0 g; 50 wt % formaldehyde solution: 225.5 g (3.75 mol). The total initial loading was 1268.5 g. One additional portion of A-150 (67.5 g) was added later in the reaction system.

At various points of the reflux stage and distillation stage, samples of the reaction mass were taken to evaluate the composition of the reaction product, in particular the content of tert-butylcalix[8]arene. Because the reaction system is triphasic (i.e., it has an aqueous and a sticky aromatic-150 layer including some solids), prior to testing, the sample was mixed at room temperature with a spatula until homogeneous.

Table 2 lists the $^1$H-NMR results for the samples of the reaction mass at various times of the reflux phase and distillation phase. As discussed in Example 7, the $^1$H NMR features of the tert-butylphenol-derived calixarenes from ring size 4 to ring size 16, such as the proton signals of the methylene bridges and of the phenolic hydroxyls in CDCl$_3$, were discussed in Stewart. In general, the proton NMR allows one to analyze calixarenes reaction masses through their respective phenolic protons (calixarenes), methylene bridges between aromatic units (for linear and cyclic compounds—at about 3.6-3.9 ppm for the linear and most cyclic compounds; for tert-butylcalix[4 & 8]arenes, one doublet at 4.3 ppm (or 4.4 ppm for tert-butylcalix[8]arene) and one doublet at 3.5 ppm), methylols (at about 4.4-4.6 ppm), and benzyl ether derivatives (at about 4.6-4.9 ppm)

as described in Perrin et al., *Supramolecular Chemistry* 4:153-57 (1994); see also, Gutsche, "*Calixarenes*" pages 27-86 (Royal Society of Chemistry, 1989), both of which are hereby incorporated by reference in their entirety, to the extent not inconsistent with the subject matter of this disclosure. The standard proton NMR does not allow one to quantify the amount of unreacted PTBP in the reaction mass since its phenolic proton disappeared in the baseline.

Table 2 also lists the results of wt % determinations for the amounts of free formaldehyde and unreacted PTBP present. The determination was based on the assumption that no mass was lost during the reflux stage. The $^1$H-NMR results of a few samples of the reaction mass at various times of the reflux stage are shown in FIGS. 17A-17D for illustrative purposes.

It was assumed that the integrals for the signal group around 4.9 ppm came just from two methylene protons with oxygen substitution; they do not contain areas from the —OH proton (i.e., the —OH protons of the methylol groups do not typically show up in a $^1$H NMR spectrum). The assumption was based on the fact that the experimental spectrum of a compound having two aromatic units connected by a methylene bridge with two methylol-groups on both ends

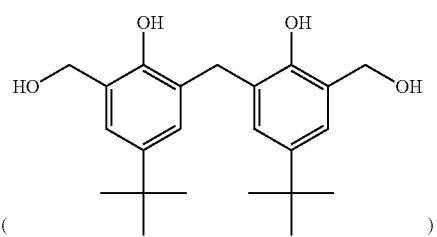 [SMILES: CC(C)(C)c1cc(CO)c(O)c(Cc2cc(C(C)(C)C)cc(CO)c2O)c1]

does not have —OH protons of the methylol groups. In addition, similar results were reported for a compound having three and four aromatic units connected by a methylene bridge with two methylol groups on both ends (see Dhawan et al., "Calixarenes. 10. Oxacalixarenes," *J. Org. Chem.* 48:1536-39 (1983), which is hereby incorporated by reference in its entirety, to the extent not inconsistent with the subject matter of this disclosure). All these experiments confirmed the above assumption.

Formaldehyde can react with para-substituted alkylphenols under the applied reaction conditions basically in three ways: forming a methylene bridge between two aromatic units; forming a substituent on an aromatic nucleus and residing as a methylol compound; or forming a dibenzylether bridge between two aromatic units. Each of the products formed from these methods have a distinct resonance area in the $^1$H-NMR, and their integrals can be determined.

Based on the above assumption, the degree of di-substitution of the reacted PTBP with formaldehyde can be determined from the weight-percentage determination for the free formaldehyde and free PTBP. Then, the reduced integral value of all methylene protons for single substituted PTBP can be calculated by correcting the observed methylol/benzyl ether derivative integral around 4.9 ppm for the di-methylolated contribution, and adding this number to the integrals of the protons for the methylene bridge protons for calixarenes and linear resins. This number serves as the basis for further calculations of how much of a particular calixarene has formed (i.e., by comparing this number against the integrals for the respective phenolic OH protons of the particular calixarene). See, for instance, the results listed in Table 3.

As shown in Table 2, the 1-hour sample contained about 5.4 mol % of unreacted formaldehyde, and the 12-hour sample still contained 4.1 mol % of unreacted formaldehyde. That is to say, during the reflux phase of the initial 12 hours, the free formaldehyde in the reaction mass samples remained essentially the same, suggesting that all formaldehyde had basically reacted during the first hour and no further reaction with formaldehyde occurred during the rest of the reflux stage. Based on this result, it was assumed that a total of about 95 mol % of the formaldehyde reacted within the first hour (and throughout the initial 12 hours in the reflux phase), and no formaldehyde, or very little, was lost through the condenser.

Moreover, in Table 2, the 1-hour sample contained about 26.4 mol % of unreacted PTBP, and the 12-hour sample contained about 17.3 mol % of unreacted PTBP. That is to say, approximately three quarters of the initial PTBP reacted within the first hour and then a little more PTBP was consumed during the next 11 hours.

TABLE 2

Analysis of the samples of the reaction mass at various reflux and distillation stages (Example 8)

| Sample Time [hours][a1] | [° C.] | Integrals for one methylene proton, tert-butylcalix[8]arene[b] | Integrals for phenolic OH, tert-butylcalix[8]arene[c] | Integrals for two phenolic protons of the four from AA[d] | Integrals for phenolic OH protons, tert-butylcalix[6]arene[e] | Free HCHO [wt %]/ [g]/ [mol]/ [mol % left] | PTBP [wt %]/ [g] (% of starting PTBP) | Integrals for two methylene protons, linear resins and other calixarenes[f] | Integrals for two methylene protons with —O— substitution[g] | Reacted PTBP [g] |
|---|---|---|---|---|---|---|---|---|---|---|
| 1 | 102.6 | 0 | 0 | 0 | 0 | 0.48/6.09/ 0.20/5.4 | 11.7/148.4 (26.4%) | 0.047 | 0.248 | 414.6/73.6 mol % reacted |
| 2 | | 0.00 | 0.001[h] | 0.001 | 0 | 0.58 | 10/126.9 (22.5%) | 0.064 | 0.316 | 436.1 |
| 3 | 102.9 | | 0.001[h] | 0.001 | 0 | 0.46 | 10.8/137.0 (24.3%) | 0.071 | 0.267 | 426 |
| 4 | 102.4 | 0.002 | 0.003 | 0.001 | 0.000 | 0.43 | 10.1/128.1 (22.8%) | 0.086 | 0.193 | 434.9 |
| 5 | 102.3 | 0.003 | 0.004 | 0.001 | 0 | 0.42 | 9.07/115.1 (20.4%) | 0.099 | 0.178 | 447.9 |
| 6 | 102.6 | 0.006 | 0.006 | 0.002 | 0.001 | 0.44 | 9.55/121.1 (21.5%) | 0.12 | 0.174 | 441.9 |
| 7 | 101.9 | 0.012 | 0.007 | 0.001 | 0.001 | 0.26 | 9.46/120.0 (21.3%) | 0.148 | 0.169 | 443 |
| 8 | 102.3 | 0.006 | 0.009 | 0.004 | 0.001 | 0.41 | 7.05/89.4 (15.9%) | 0.117 | 0.160 | 473.6 |
| 9 | 102.1 | 0.014 | 0.012 | 0.002 | 0.002 | 0.40 | 8.73/110.7 (19.7%) | 0.152 | 0.146 | 452.3 |
| 10 | 101.9 | 0.019 | 0.013 | 0.001 | 0.001 | 0.38 | 8.07/102.4 (18.2%) | 0.162 | 0.149 | 460.6 |
| 11 | 101.6 | 0.018 | 0.018 | 0.002 | 0.002 | 0.38 | 7.64/96.9 (17.2%) | 0.154 | 0.128 | 466.1 |
| 12 | 103.8 | 0.021 | 0.019 | 0.003 | 0.003 | 0.36/4.57/ 0.15207/4.05 | 7.86/97.4 (17.3%) | 0.159 | 0.129 | 465.6/82.7 mol % reacted |

TABLE 2-continued

Analysis of the samples of the reaction mass at various reflux and distillation stages (Example 8)

| Sampling time [hours][a2] | Start to distill [° C.]/ total ml distilled out [g][i]/ therefore remaining mass in flask[j] [g] | Integrals for one methylene proton, tert-butylcalix[8]arene[b] | Integrals for phenolic OH protons, tert-butylcalix[8]arene[c] | Integrals for two phenolic protons of the four from AA[d] | Integrals for phenolic OH protons, tert-butylcalix[6]arene[e] | Free HCHO [wt %]/ [g]/ [mol]/ [mol %] | PTBP [wt %]/ [g] (% of starting PTBP) | Integrals for two methylene protons linear resins and other calixarenes[f] | Integrals for two methylene protons with —O—substitution[g] | Reacted PTBP [mol %] |
|---|---|---|---|---|---|---|---|---|---|---|
| I, 12.25 | 105.1/29/ 1239.5 | 0.027 | 0.026[h] | 0.003 | 0.003 | 0.28 | 8.05/99.78/17.7 | 0.186 | 0.133 | 82.3 |
| II, 12.42 | 107.8/99/ 1169.5 | | | | | 0.14[k] | 8.48/99.17/17.6 | | | 82.4 |
| III, 12.50 | 115.2/124/ 1212.7[l] | 0.025 | 0.020 | 0.003 | 0.003 | 0.07 | 8.75/106.1/18.8 | 0.180 | 0.127 | 81.2 |
| IV, 12.58 | 130/131/ 1205.7 | | | | | 0.06 | 8.12/97.9/17.4 | | | 82.6 |
| V, 12.67 | 145/135/ 1201.7 | 0.033 | 0.025 | 0.002 | 0.003 | 0.06 | 7.88/94.7/16.8 | 0.169 | 0.109 | 83.2 |
| A, 13.67 | 145/145/ 1191.7 | 0.065 | | 0.000 | 0.003 | 0.03 | 5.36/63.9/11.3 | 0.207 | 0.044 | 88.7 |
| B, 14.67 | 145.5/148/ 1188.7 | 0.048 | 0.047[h] | 0.001 | 0.001 | 70 ppm | 4.35/51.7/9.2 | 0.157 | 0.022 | 90.8 |
| C, 15.67 | 145/150/ 1186.7 | 0.054 | 0.053 | 0.000 | 0.001 | <15 ppm | 3.97/47.1/8.4 | 0.157 | 0.007 | 91.6 |
| D, 16.67 | 145.6/150/ 1186.7 | 0.086 | 0.084 | 0.001 | 0.001 | 60 ppm | 3.89/46.2/8.2 | 0.222 | 0.006 | 91.8 |
| E, 17.17 | 145/152/ 1184.7 | 0.078 | 0.080 | 0.000 | 0.001 | <15 ppm | 3.71/44.0/7.8 | 0.200 | 0.002 | 92.2 |
| Final | | 0.105 | 0.106 | 0.000 | 0.001 | <15 ppm | 3.88 | 0.266 | 0 | |

[a1]Sampling time: number of hours after the end of the formaldehyde addition and reaching reflux
[a2]Sampling time: number of hours after the end of the formaldehyde addition; I-V indicate different stages of distillation stage when heating to 145° C.; A-E indicate different stages of distillation stage after reaching 145° C.
[b]Value was taken directly from the NMR spectrum at about 4.4 ppm
[c]Value was taken directly from the NMR spectrum at about 9.66 ppm
[d]Value was taken directly from the NMR spectrum at about 9.01 ppm
[e]Value was taken directly from the NMR spectrum at about 10.56 ppm
[f]Value was taken directly from the NMR spectrum at about 3.9 ppm
[g]Value was taken directly from the NMR spectrum at about 4.9 ppm
[h]Peak has a tiny, little shoulder (likely from structure AA)
[i] ml assumed as gram
[j] The weight of the samples were not taken into account
[k]Formaldehyde distills out - assuming that the formaldehyde consumption was 95% in the first hour and did not change
[l]The second portion of 68.2 g A-150 was added

TABLE 3

Analysis of the samples of the reaction mass at various reflux and distillation stages (Example 8)

| Sample Time/ [min][a] | Integrals for one methylene proton tert-butylcalix[8]arene[b]/ [% from total reacted PTBP[c]] | Integrals for phenolic OH photons, tert-butylcalix[6]arene[d]/ [% from total reacted PTBP[c]] | Free HCHO [wt %]/[g]/ [mol]/[mol % left] | PTBP [wt %]/[g] (% of starting PTBP) | Calculated molar ratio of reacted HCHO to reacted PTBP | Integrals for two methylene protons, linear resins and calixarenes[e] |
|---|---|---|---|---|---|---|
| 1 | 0/0 | 0 | 0.48/6.09/ 0.20/5.4 | 11.7/148.4 (26.4%) | 1.291 | 0.047 |
| 2 | 0.00/0 | 0/0 | 0.58 | 10/126.9 (22.5%) | 1.226 | 0.064 |
| 3 | | 0/0 | 0.46 | 10.8/137.0 (24.3%) | 1.255 | 0.071 |
| 4 | 0.002/1.6 | 0.000/0 | 0.43 | 10.1/128.1 (22.8%) | 1.231 | 0.086 |
| 5 | 0.003/2.4 | 0/0 | 0.42 | 9.07/115.1 (20.4%) | 1.193 | 0.099 |
| 6 | 0.006/4.5 | 0.001/0.8 | 0.44 | 9.55/121.1 (21.5%) | 1.210 | 0.12 |
| 7 | 0.012/8.3 | 0.001/0.7 | 0.26 | 9.46/120.0 (21.3%) | 1.207 | 0.148 |

TABLE 3-continued

Analysis of the samples of the reaction mass at various reflux and distillation stages (Example 8)

| | | | | | | |
|---|---|---|---|---|---|---|
| 8 | 0.006/4.6 | 0.001/0.8 | 0.41 | 7.05/89.4 (15.9%) | 1.130 | 0.117 |
| 9 | 0.014/10.2 | 0.002/1.5 | 0.40 | 8.73/110.7 (19.7%) | 1.183 | 0.152 |
| 10 | 0.019/13.1 | 0.001/0.7 | 0.38 | 8.07/102.4 (18.2%) | 1.161 | 0.162 |
| 11 | 0.018/13.5 | 0.002/1.5 | 0.38 | 7.64/96.9 (17.2%) | 1.147 | 0.154 |
| 12 | 0.021/15.5 | 0.003/2.2 | 0.36/4.57/ 0.15/4.05 | 7.86/97.4 (17.3%) | 1.149 | 0.159 |
| I | 0.027/17.9 | 0.003 | 0.28 | 8.05/99.78/17.7 | 1.154 | 0.186 |
| II | | | 0.14[i] | 8.48/99.17/17.6 | 1.153 | |
| III | 0.025/17.3 | 0.003 | 0.07 | 8.75/106.1/18.8 | 1.170 | 0.180 |
| IV | | | 0.06 | 8.12/97.9/17.4 | 1.150 | |
| V | 0.033/25.0 | 0.003 | 0.06 | 7.88/94.7/16.8 | 1.142 | 0.169 |
| A | 0.065/52.4 | 0.003 | 0.03 | 5.36/63.9/11.3 | 1.071 | 0.207 |
| B | 0.048/53.9 | 0.001 | 70 ppm | 4.35/51.7/9.2 | 1.046 | 0.157 |
| C | 0.054/60.7 | 0.001 | <15 ppm | 3.97/47.1/8.4 | 1.037 | 0.157 |
| D | 0.086/70.4 | 0.001 | 60 ppm | 3.89/46.2/8.2 | 1.035 | 0.222 |
| E | 0.078/77.2 | 0.001 | <15 ppm | 3.71/44.0/7.8 | 1.030 | 0.200 |
| Final | 0.105 | 0.001 | <15 ppm | 3.88 | | 0.266 |

| Sample Time/ [min][a] | Integrals for two methylene protons with —O— substitution[f] | % of all methylol/benzyl ethers protons in the total reacted material in relation to all reacted PTBP [mol %] | Corrected integrals for two methylene proton with —O— substitution[g] | Sum of corrected integrals for two methylene protons with —O— substitution[g] + integrals for two methylene protons resins and calixarenes[e] | Sum[h] of integrals for corrected one methylene proton with —O— substitution[g] + integrals for one methylene proton from linear resins and calixarenes[e] |
|---|---|---|---|---|---|
| 1 | 0.248 | 103.8 | 0.192 | 0.239 | 0.1195 |
| 2 | 0.316 | 98.1 | 0.258 | 0.322 | 0.161 |
| 3 | 0.267 | 94.0 | 0.213 | 0.284 | 0.142 |
| 4 | 0.193 | 79.4 | 0.157 | 0.243 | 0.1215 |
| 5 | 0.178 | 71.8 | 0.149 | 0.248 | 0.124 |
| 6 | 0.174 | 66.9 | 0.144 | 0.264 | 0.132 |
| 7 | 0.169 | 58.7 | 0.140 | 0.288 | 0.144 |
| 8 | 0.160 | 61.8 | 0.142 | 0.259 | 0.1295 |
| 9 | 0.146 | 53.1 | 0.123 | 0.275 | 0.1375 |
| 10 | 0.149 | 51.4 | 0.128 | 0.290 | 0.145 |
| 11 | 0.128 | 48.1 | 0.112 | 0.266 | 0.133 |
| 12 | 0.129 | 47.6 | 0.112 | 0.271 | 0.1355 |
| I | 0.133 | 44.2 | 0.115 | 0.301 | 0.1505 |
| II | | | | | |
| III | 0.127 | 43.9 | 0.109 | 0.289 | 0.1445 |
| IV | | | | | |
| V | 0.109 | 41.3 | 0.095 | 0.264 | 0.132 |
| A | 0.044 | 17.7 | 0.041 | 0.248 | 0.124 |
| B | 0.022 | 12.4 | 0.021 | 0.178 | 0.089 |
| C | 0.007 | 4.3 | 0.007 | 0.164 | 0.082 |
| D | 0.006 | 2.6 | 0.006 | 0.228 | 0.114 |
| E | 0.002 | 1.0 | 0.002 | 0.202 | 0.101 |
| Final | 0 | | | | |

[a]Sampling time: number of hours after the start of water removal; see the Sample time column in Table 2.
[b]Value was taken directly from the NMR spectrum at about 4.4 ppm
[c]Determined from one methylene proton from the last column
[d]Value was taken directly from the NMR spectrum at about 10.56 ppm
[e]Value was taken directly from the NMR spectrum at about 3.9 ppm (including from calix[4]arene & calix[8]arene)
[f]Value was taken directly from the NMR spectrum at about 4.9 ppm
[g]Value was taken from the NMR spectrum at about 4.9 ppm with no di-substitution
[h]This number excluded di-substitution
[i]Formaldehyde is distilling out (for the calculations it is assumed that the formaldehyde consumption was 95% in the first hour and did not change)

The ratio of mono- and di-addition of formaldehyde to the PTBP molecules in each sample can be calculated by dividing the reacted molar amount of formaldehyde by the reacted molar amount of PTBP, as shown in Table 3. This number is usually greater than 1.0. During the distillation phase, unreacted accessible phenolic aromatic carbons can only react until all the methylol or dibenzylether groups have disappeared in the $^1$H-NMR spectra; only then it can become 1.0. The decimals above 1.0 reflect the molar percentage of reacted PTBP, at which point the reacted PTBP molecule has bonded with two molecules of formaldehyde. For instance, in the 1-hour reflux sample, the molar ratio between the reacted formaldehyde and reacted PTBP is 1.291. This means that 29.1 mol % of the reacted PTBP molecules had bonded with two molecules of formaldehyde. The integrals of the methylol and dibenzylether protons can be normalized for "di-substitution" of the alkylphenols that reacted with formaldehyde. Then, from the integral values obtained from the $^1$H-NMR spectra, one can calculate a baseline number for all reacted PTBP in the reaction mass. This baseline number can be obtained from the proton NMR, by adding the integrals of the "corrected" methylol and dibenzylether protons and all the integrals of the protons from the methylene bridges of linear and calixarene resin molecules. The different values for, e.g., the different phenolic protons of different-sized calixarenes can now be compared against this obtained corrected integral sum to estimate their particular concentrations in the total reaction mass.

In sum, the methylene bridges between the aromatic units in these calixarene reaction masses usually reflect the reaction of one alkylphenol with one formaldehyde for the calixarenes. For linear resins, this alkylphenol to formaldehyde ratio holds only if one terminal aromatic unit is substituted by a methylol group; if the two terminal aromatic units are not substituted by any methylol groups, this alkylphenol to formaldehyde ratio will be lower. One needs to correct the methylene proton integrals of the methylol or dibenzylether resonance for the amount of alkylphenol having reacted with two molecules of formaldehyde. This was done by dividing the areas of the methylol/benzylether protons by the molar ratio of the reacted formaldehyde and the reacted alkylphenol. The sum of this corrected area together with the area for all the methylene protons would then approximately capture the mono-substitution of the alkylphenol reacted with formaldehyde.

The analysis of the total reacted PTBP (or other alkylphenol starting material) from the integrals in the $^1$H-NMR spectra was determined by the following method. The methylene bridge protons between the phenolic units are typically present at around 3.9 ppm (tert-butylcalix[4 & 8]arenes show the doublets at around 4.4 (4.3 for tert-butylcalix[4]arene) and 3.5 ppm). The methylene protons of the oxygen-substituted protons of the methylene group at the aromatic unit are typically present between 4.5-5.5 ppm. It was assumed that the sum of the areas of the methylene protons and the corrected methylols/benzylethers would be representative for all reacted PTBP molecules, and that this area value can then be used to relate the other integrals to obtain the concentration of a particular compound.

Based on the above analyses from the collected $^1$H-NMR data and the weight-percentage determination, after normalizing these $^1$H-NMR results, the following results are provided in Table 3.

Figure 18A:
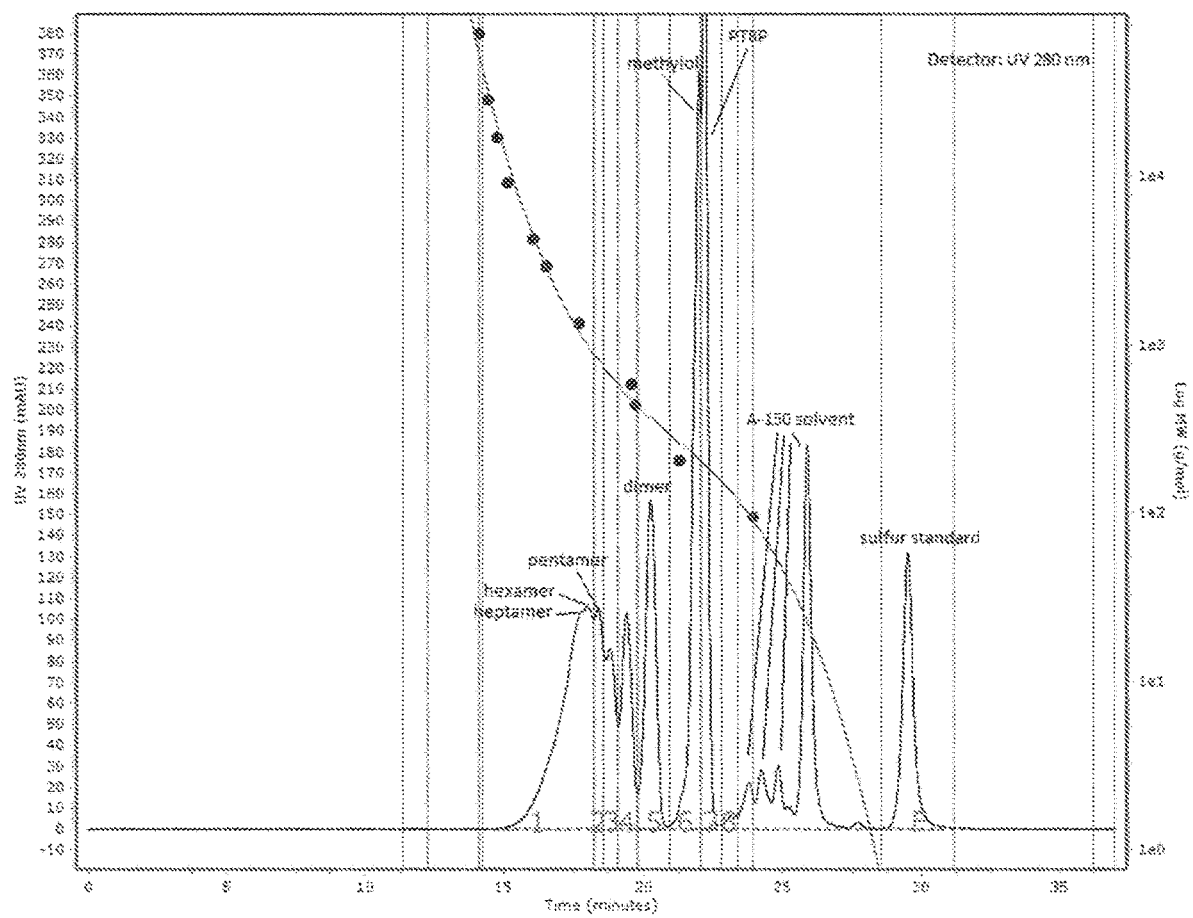
FIG. 18A shows the low-set GPC results of the sample taken from the reaction mass after one hour of reaching reflux, prepared from Example 8.
Figure 18B:
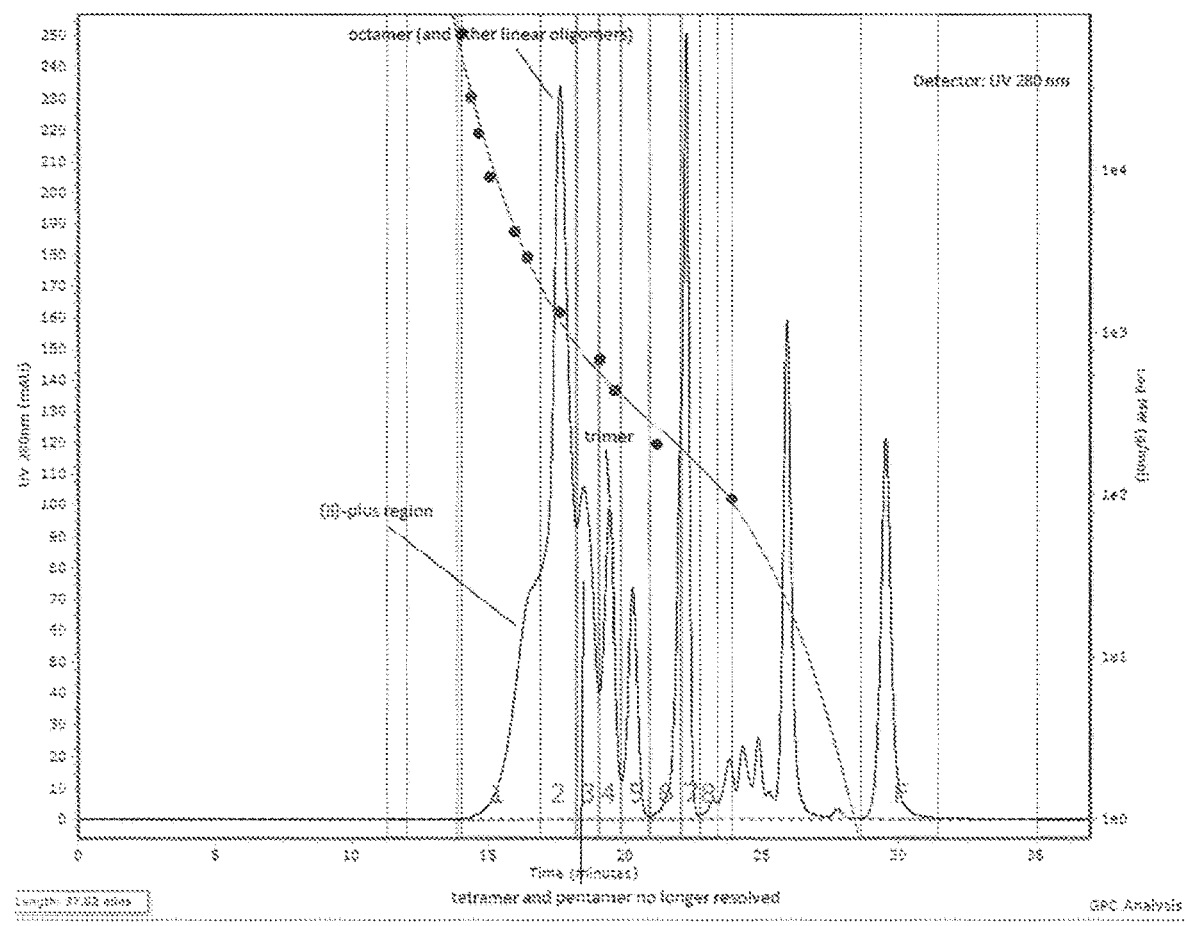
FIG. 18B shows the low-set GPC results of the sample taken from the reaction mass after twelve hours of reaching reflux, prepared from Example 8.

Low-set GPC analyses were also performed for the samples of the reaction mass at various times of the reflux stage and distillation stage, to understand the degree and distribution of the calixarene resin formation and their pre-cursors over time, particularly because GPC distinguishes the molecules by size. The low-set GPC results of two samples are shown in FIGS. 18A-18B to illustrate how the data were collected and results were analyzed. FIG. 18A shows the low-set GPC result for the 2-hour reflux sample and FIG. 18B shows the low-set GPC result for the 12-hour reflux sample. It is understood that the linear resins can have zero, one, or two methylol groups at their terminal phenol groups; they can also contain benzylether linkages in-between the aromatic nuclei. These distinctive linear chains cannot easily be resolved by GPC and the peaks were just grouped as "dimers," "trimers," "tetramers," etc., independent of their methylol/ether substitution pattern. The oligomer compounds larger than the calix[8]arene are referred to as "[8] plus-region." The low-set GPC results provide area-% (280 nm) as well as $M_w$ for each segment.

Figure 19:
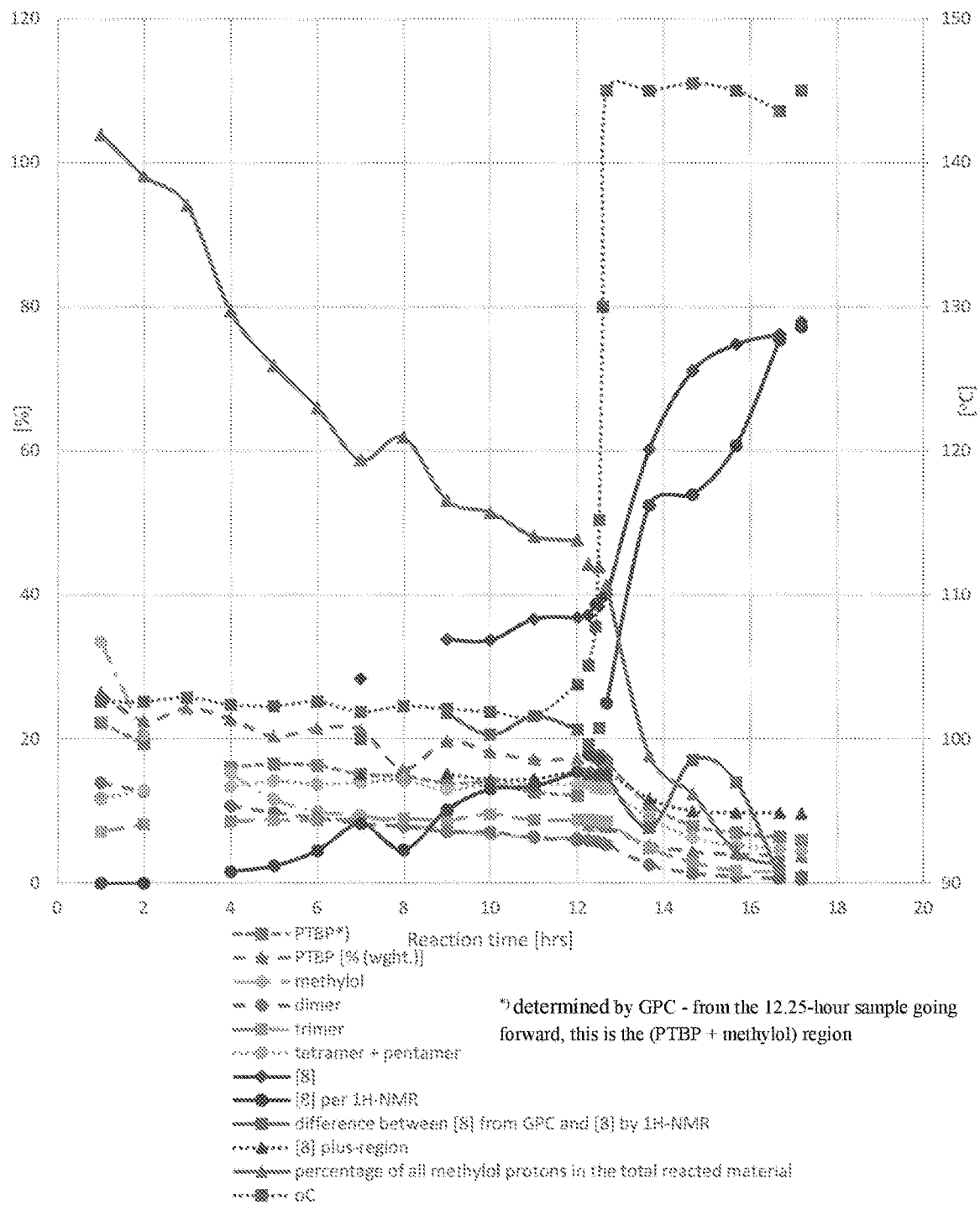
FIG. 19 is a graph showing the reaction kinetics of the reaction between PTBP, 100 mol % HCHO, and TEAOH, determined by means of low-set GPC, $^1$H-NMR, and wt % of PTBP and HCHO.

Table 4 summarizes the identified area % (collected at 280 nm) from these low-set GPCs as well as the wt % of the PTBP and tert-butylcalix[8]arenes as determined by $^1$H-NMR for the samples of the reaction mass at various times of the reflux stage and distillation stage. Some results were also plotted in FIG. 19.

The final column in this table was derived from the kinetic $^1$H-NMR data and displays how much methylol/benzylether compound is present in all the formed product at a specific point in time. If all methylol/benzylether groups have been converted at the end of the reaction, this value would become 0 or as close as possible to 0. As shown in Table 4 as well as in FIG. 19, during the initial 12 hours of reflux stage, the percentage of all methylol protons and benzylether protons in the total reacted materials in relation to the total reacted PTBP continuously reduced from about 100% to about 47%. A constant reduction in this value indicates a constant disappearing of the terminal methylol groups (or the bridging dibenzylether groups) to become the methylene bridges between the phenolic rings, forming the desired oligomers. During the distillation phase, this value reduced from about 47% (after the reflux stage and at the beginning of the distillation stage) to about 1% at the end of distillation stage (after about 5 hours of distillation), indicating that the cyclization toward the desired calix[8]arene took place, ending up with a high yield/high selectivity calix[8]arene product.

The results of this kinetic model is in contrast to the kinetic mechanism observed for the conventional calixarene formation process using paraform in xylene and an alkaline base as the catalyst (see, e.g., Vocanson et al., "Characterization of synthetic precursors of p-tert-butylcalix[4]arene and p-tert-butylcalix[8]arene. Mechanisms of formation of calix[4]arene and calix[8]arene," *Supramolecular Chemistry* 1(7): 19-25 (1996), which is incorporated herein by reference in its entirety, to the extent not inconsistent with the subject matter of this disclosure). While the conventional alkaline base catalysts convert the formaldehyde in a much faster kinetics, the nitrogen-containing base catalysts allowed for a slower build-up of desirable linear precursors for the formation of tert-butylcalix[8]arenes.

TABLE 4

Analysis of the samples of the reaction mass at various reflux and distillation stages (Example 8)

| Sample Time/ [hour]$^a$ | PTBP$^b$ (by GPC) | PTBP [wt %] | methylol (by GPC) | dimer (by GPC) | trimer (by GPC) | tetramer + pentamer (by GPC) | calix[8] arene (by GPC)$^c$ | calix[8] arene (by $^1$H-NMR) | difference between calix[8]arene from GPC and by $^1$H-NMR | calix[8]arene plus-region (by GPC) | ° C. | percentage of all methylol/benzyl ether protons in the total reacted material in relation to all reacted PTBP (from $^1$H-NMR) |
|---|---|---|---|---|---|---|---|---|---|---|---|---|
| 1 | 22.25 | 26.4 | 33.49 | 13.98 | 7.2 | 11.79 | | 0 | | | 102.6 | 103.8 |
| 2 | 19.4 | 22.5 | 20.6 | 12.75 | 8.2 | 12.99 | | 0 | | | 102.6 | 98.1 |
| 3 | | 24.3 | | | | | | | | | 102.9 | 94 |
| 4 | 16.16 | 22.8 | 15.27 | 10.73 | 8.65 | 13.46 | | 1.6 | | | 102.4 | 79.4 |
| 5 | 16.56 | 20.4 | 11.74 | 9.84 | 8.83 | 14.2 | | 2.4 | | | 102.3 | 71.8 |
| 6 | 16.36 | 21.5 | 9.95 | 9.1 | 8.78 | 13.78 | | 4.5 | | | 102.6 | 65.9 |
| 7 | 15.15 | 21.3 | 9.49 | 8.3 | 8.97 | 14.01 | 28.39 | 8.3 | 20.09 | 15.15 | 101.9 | 58.7 |
| 8 | 14.91 | 15.9 | 8.21 | 7.92 | 9.03 | 14.33 | | 4.6 | | | 102.3 | 61.8 |
| 9 | 13.93 | 19.7 | 7.44 | 7.21 | 8.81 | 13.02 | 33.84 | 10.2 | 23.64 | 15.25 | 102.1 | 53.1 |
| 10 | 13.94 | 18.2 | 6.77 | 7.13 | 9.63 | 13.84 | 33.72 | 13.1 | 20.62 | 14.4 | 101.9 | 51.4 |
| 11 | 12.68 | 17.2 | 6.51 | 6.36 | 8.82 | 13.73 | 36.68 | 13.5 | 23.18 | 14.51 | 101.6 | 48.1 |
| 12 | 12.22 | 17.3 | 6.25 | 5.99 | 8.83 | 13.74 | 36.84 | 15.5 | 21.34 | 15.62 | 103.8 | 47.6 |
| 12.25 | 15.19 | 8.05 | | 5.96 | 8.87 | 13.93 | 37.17 | 17.9 | 19.27 | 15.19 | 105.1 | 44.2 |
| 12.43 | 17.8 | 8.48 | | 5.84 | 8.79 | 13.27 | 38.7 | | | 15.07 | 107.8 | |
| 12.5 | 17.63 | 8.75 | | 5.73 | 8.7 | 13.69 | 38.34 | 17.3 | 21.54 | 15.37 | 115.2 | 43.9 |
| 12.58 | 17.15 | 8.12 | | 5.59 | 8.53 | 13.21 | 39.79 | | | 15.17 | 130 | |
| 12.67 | 16.8 | 7.88 | | 5.33 | 8.64 | 13.23 | 39.98 | 25 | 14.98 | 15.49 | 145 | 41.3 |
| 13.67 | 10.94 | 5.36 | | 2.55 | 4.86 | 9.2 | 60.16 | 52.4 | 7.76 | 11.78 | 145 | 17.7 |
| 14.67 | 8.01 | 4.35 | | 1.36 | 2.89 | 6.31 | 71.02 | 53.9 | 17.12 | 10.04 | 145.5 | 12.4 |
| 15.67 | 7.03 | 3.97 | | 0.91 | 1.72 | 5.21 | 74.75 | 60.7 | 14.05 | 9.86 | 145 | 4.3 |
| 16.67 | 6.45 | 3.89 | | 0.68 | 1.65 | 4.75 | 76.15 | 75.4 | 0.75 | 9.82 | 143.6 | 2.6 |
| 17.17 | 5.95 | 3.71 | | 0.54 | 0.85 | 4.39 | 77.96 | 77.2 | 0.76 | 9.72 | 145 | 1 |
| final | 6.01 | 3.88 | | 0.52 | 1.34 | 4.59 | 77.14 | | | 9.83 | | |

$^a$Sampling time: number of hours after the end of the formaldehyde addition and reaching reflux at about 100.5° C.
$^b$From the 12.25 hour sample going forward, this is the (PTBP + methylol) region
$^c$It may contain other linear resins at well.

Example 9. Synthesis of Sec-Butylcalix[8]Arenes Using Tetramethylammonium Hydroxide (TMAOH) as the Catalyst

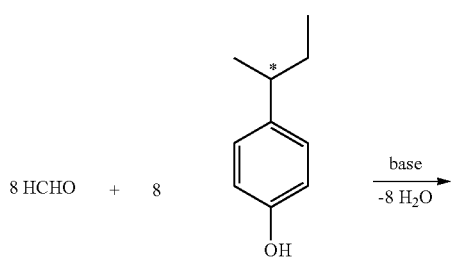

mp.: 46-59° C.
bp.: 133-136° C.

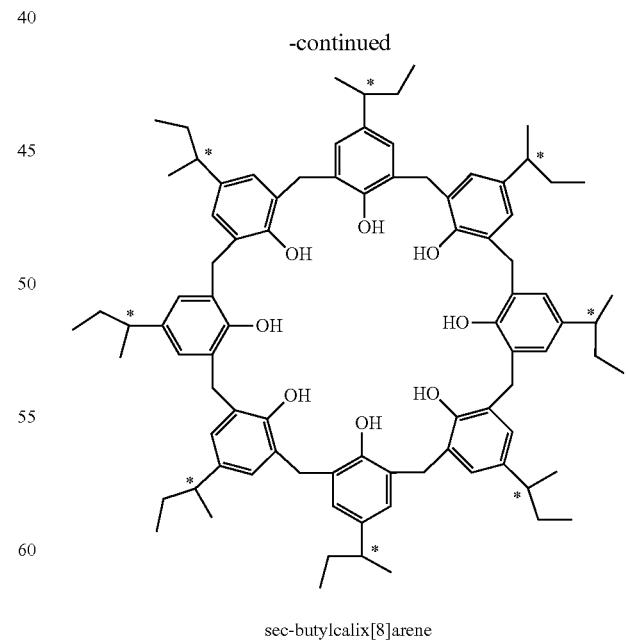

sec-butylcalix[8]arene

A 500 ml round bottom flask, equipped with an overhead stirrer, thermocouple, overhead addition tank, moisture trap, and condenser was loaded with 112.7 g para-sec-butylphenol (PSBP) powder (>98%, 0.75 mol) and 100.2 g A-150 (Solvesso™ 150 Fluid). A gentle nitrogen flow was applied on the surface of the hot reaction mass and the reactor was heated to about 90° C. When all the PSBP and the A-150 formed a clear solution, 5.5 g of TMAOH solution (25 wt % in methanol, 0.015 mol) was added dropwise at a temperature of 85-90° C., and this temperature was hold for 30 minutes. At 90° C., a total of 46.0 g of 48.9 wt % formaldehyde solution (0.749 mol) was added within 16 minutes.

After the formaldehyde addition, the reaction was kept at 90° C. for 1 hour. The reaction mixture was then heated to reflux for a total of 12 hours. At the end of the reflux, the reaction mass was at about 99° C.

The reaction mass was diluted with 99.7 g more A-150 solvent. The reactor was then heated and the temperature target was set to 145° C. to remove the water. About 2 hours after the heating was started, the temperature of the reaction mass reached about 142° C., and was kept at 142-145° C. for about 10 hours until a total of 26.8 g of the lower layer was removed. The crude reaction mass contained 3.43 wt % PSBP.

Figure 20:
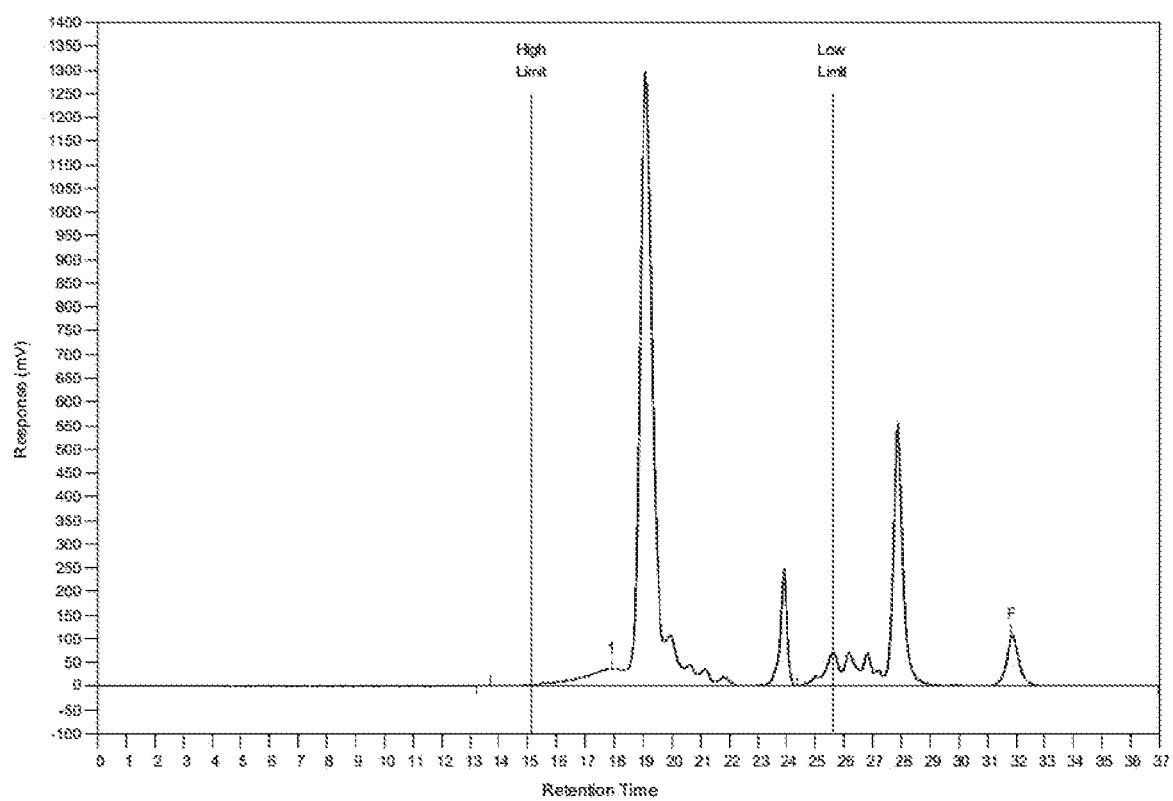
FIG. 20 shows the GPC results of the crude reaction mass prepared from Example 9.

The GPC results of the crude reaction mass are shown in FIG. 20. Theoretically, the solid content of the crude reaction mass was calculated to be 37.7 wt % (assuming all water from formaldehyde solution and produced from the reaction were removed; and all excess formaldehyde was removed). The crude reaction mass contained 3.43 wt % free PSBP (which corresponds to 11.08 g or 9.8 mol % of unreacted PSBP).

Figure 21:
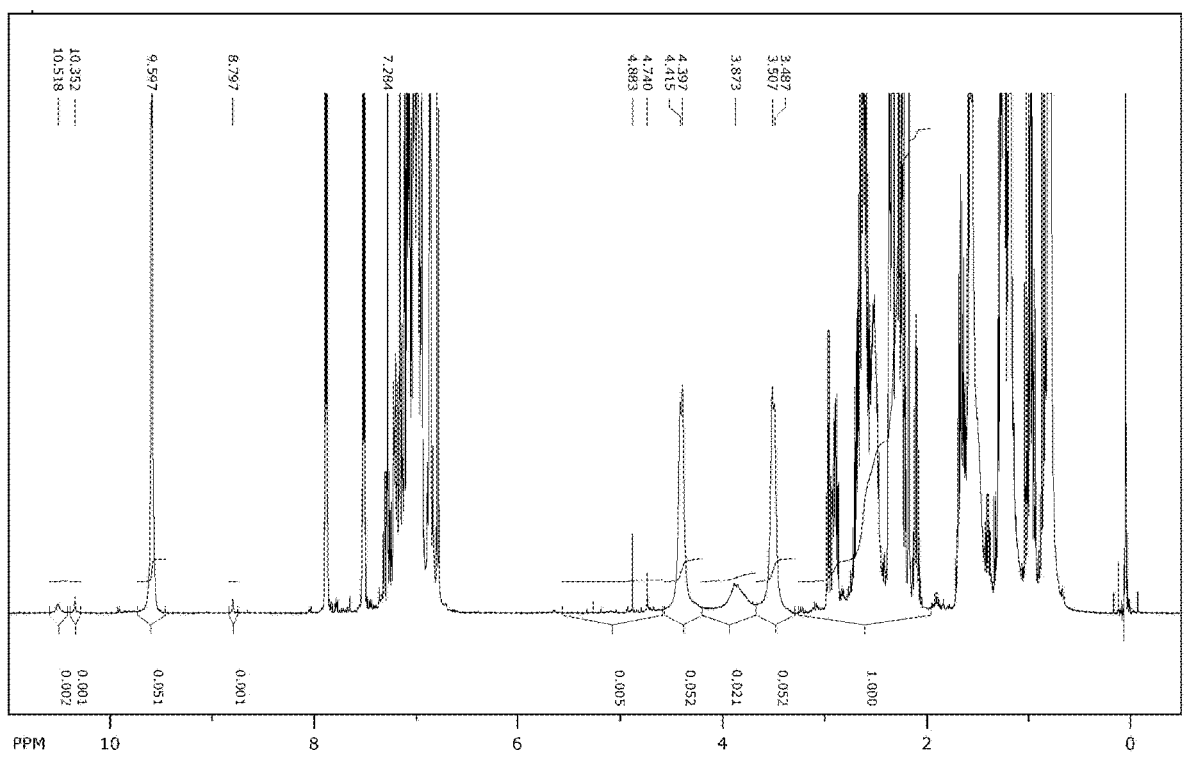
FIG. 21 shows the $^1$H-NMR results of the crude reaction mass prepared from Example 9.

The $^1$H-NMR results of the crude reaction mass are shown in FIG. 21. The yields of the cyclic phenolic resins were determined by further analysis of the $^1$H-NMR results of the crude reaction mass, using the calculation methodology discussed in Example 1. It was understood that the $^1$H-NMR does not allow the quantification of the free monomer content; but the GPC results of the final reaction mass display all components in the reaction mass (with their respective resonances at the picked wavelength (here 280 nm)).

The analysis results of the $^1$H-NMR in FIG. 21 are as follows.

| | |
|---|---|
| Integrals for calixarene phenolic OH protons (for all calixarenes) | 0.055 |
| Integrals for two protons of all methylene bridges (cyclic and linear resins) | 0.130 |
| Integrals for one proton of all methylene bridges (cyclic and linear resins) | 0.065 |
| Ratio of calixarene phenolic OH protons to the protons of all methylene bridges | 0.055/0.065 = 84.6% |

Taking into account the 9.8 mol % unreacted PSBP in the yield calculation (i.e., 90.2 mol % of the PSBP had reacted) resulted in a crude calixarene yield of 76.3% (i.e., 84.6%×0.902). That is to say, the theoretical yield of all cyclic components in this crude reaction mass was 76.3%.

Applying the same calculation for the sec-butylcalix[8] arene provided the following results.

| | |
|---|---|
| Integrals for sec-butylcalix[8]arene phenolic OH protons | 0.051 |
| Integrals for two protons of all methylene bridges (cyclic and linear resins) | 0.130 |
| Integrals for one proton of all methylene bridges (cyclic and linear resins) | 0.065 |
| Ratio of sec-butylcalix[8]arene phenolic OH protons to the protons of all methylene bridges | 0.051/0.065 = 78.5% |

Taking into account the 9.8 mol % unreacted PSBP in the yield calculation resulted in a crude sec-butylcalix[8]arene yield of 70.8% (i.e., 78.5%×0.902). That is to say, the theoretical yield of sec-butylcalix[8]arene in this crude reaction mass was 70.8%. This is close to the observed isolated yield.

This crude reaction mass obtained above was then cooled to about 80° C., and was easily filtered through a Buechner funnel. The filter cake was successively washed with a total of 105.4 g of A-150. After drying, the product sec-butylcalix[8]arene was obtained in an isolated yield of 66.3% (theoretical yield), with an HPLC purity of 99.2% (area % at 281 nm), and less than 0.05 wt % free PSBP and less than 0.05 wt % A-150.

As noted above and demonstrated through these examples, it has been discovered that calix[8]arenes are obtained in a higher yield and higher solid content, and with a significantly improved purity and selectivity. The use of a nitrogen-containing base as a catalyst assists this process. The purity of calix[8]arenes can be further improved by a simple filtration, without the need for recrystallization.

As a comparison, the conventional process using an alkaline base (such as sodium hydroxide) as the catalyst in a highly diluted reaction system (e.g., 100 g PTBP reacting with 35 g paraformaldehyde in 600 ml xylene solvent; see Munch et al., *Organic Syntheses* 68: 243-46 (1990)) produced with about 20% solid content, and needed a recrystallization step to remove at least 13% of other calixarene oligomers (e.g., calix[4]arene and calix[6]arene) produced in the crude cyclic reaction product. The process disclosed in this application was able to produce about 33% or more solid content, with a purity of calix[8]arene of 98% or more (characterized by HPLC analysis; not accounting for the attached solvent and the unreacted free phenolic monomers), after a filtration and drying step. See Examples 1, 5, and 7. For instance, in Example 7, 550 g PTBP reacting with 220 g formaldehyde in 367 ml A-150 solvent produced about 68.2% solid content, with a selectivity for tert-butylcalix[8]arene of 95.5% (out of all the formed calixarenes; this was determined by separating all the formed calixarenes by a preparative column chromatography, with area-% HPLC at 281 nm). No recrystallization was needed.

Example 10. Synthesis of Tert-Amylcalix[8]Arenes Using Tetramethylammonium Hydroxide (TMAOH) as the Catalyst in Diphenylether/Xylene A 500 ml round bottom flask, equipped with an overhead stirrer, thermocouple, overhead addition tank, moisture trap, and condenser was loaded with 123.2 g para-tert-amylphenol (PTAP) briquettes (0.75 mol), 90.2 g diphenylether (DPE), and 10.2 g xylene. A gentle nitrogen flow was applied on the surface of the reaction mass and the reactor was heated to about 90° C. When all the PTAP and the DPE/xylene formed a clear solution, 5.5 g of TMAOH solution (25 wt % in methanol, 0.015 mol) was added dropwise at a temperature of 89° C. over the course of 3 minutes, and this temperature was held for 75 minutes. At 89° C., a total of 52.2 g of 49.2 wt % formaldehyde solution (0.86 mol) was added within 25 minutes.

After the formaldehyde addition, the reaction was kept at 90° C. for 1 hour. The reaction mixture was then heated to reflux at about 96° C. for a total of 12 hours. At the end of the reflux, the reaction mass was at about 100° C.

The reaction mass was diluted with 60.1 g DPE and 20.1 g xylene solvent mixture. Xylene was added to remove the formed water from the reaction mass to avoid boilovers (due to the high boiling point of diphenyl ether as it cannot form effective azeotropes with water by itself).

The reactor was then heated and the temperature target was set to 145° C. to remove the water. The temperature of the reaction mass was kept at 145° C. for a total of 10 hours until a total of 34.5 g of lower layer was removed. This water layer contained 6.4 wt % formaldehyde, which correlates to 8.6% of the total formaldehyde load. The crude reaction mass contained 1.02 wt % PTAP (which corresponds to 2.6% of the starting load of PTAP).

This crude reaction mass obtained above was then cooled to about 50° C., and was filtered through a Buechner funnel. The filter cake was successively washed with xylene (a total of 106.2 g), and dried in a vacuum oven at 130° C. The final product tert-amylcalix[8]arene was obtained in an isolated yield of 81.2% (theoretical yield) with an HPLC purity of 98.8% (area % at 281 nm) and less than 0.05 wt % free PTAP and 2.78% DPE.

Example 11. Synthesis of Tert-Octylcalix[8]Arenes Using Tetraethylammonium Hydroxide (TEAOH) as the Catalyst in Hexadecane A 500 ml round bottom flask, equipped with an overhead stirrer, thermocouple, overhead addition tank, moisture trap, and condenser was loaded with 154.7 g para-tert-octylphenol (PTOP) briquettes (0.75 mol) and 100.0 g hexadecane. A gentle nitrogen was applied on the surface of the reaction mass and the reactor was heated to about 90° C. When all the PTOP and the A-150 formed a clear solution, 5.5 g of a 40% solution of TEAOH (40 wt % in water, 0.015 mol) was added dropwise over the course of 9 minutes. At 90° C., a total of 55.3 g of 46.8 wt % formaldehyde solution (0.86 mol) was added within 25 minutes.

After the formaldehyde addition, the reaction was kept at 90° C. for 1 hour. The reaction mixture was then heated to reflux at about 100° C. for a total of 12 hours. At the end of the reaction, the reaction mass was about 100° C.

Figure 22:
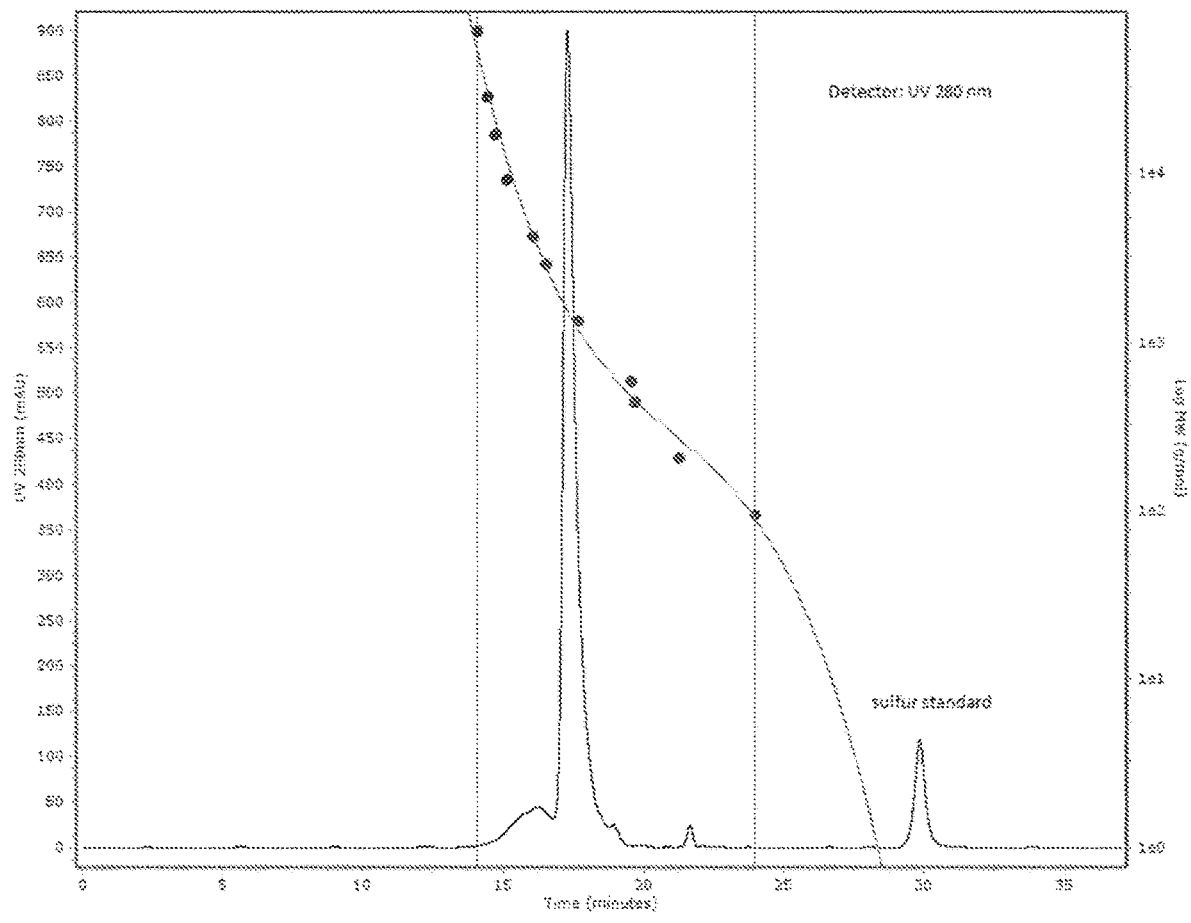
FIG. 22 shows the GPC results of the crude reaction mass prepared from Example 11.

The reaction mass was diluted with 70.1 g more hexadecane solvent. The reactor was then heated and the temperature target was set to 145° C. to remove the water. About 2 hours after the heating was started, the temperature of the reaction mass reached about 145° C., and was kept for about 10 hours. The crude reaction mass contained 0.68 wt % PTOP. The GPC results of the crude reaction mass are shown in FIG. 22.

Figure 23:
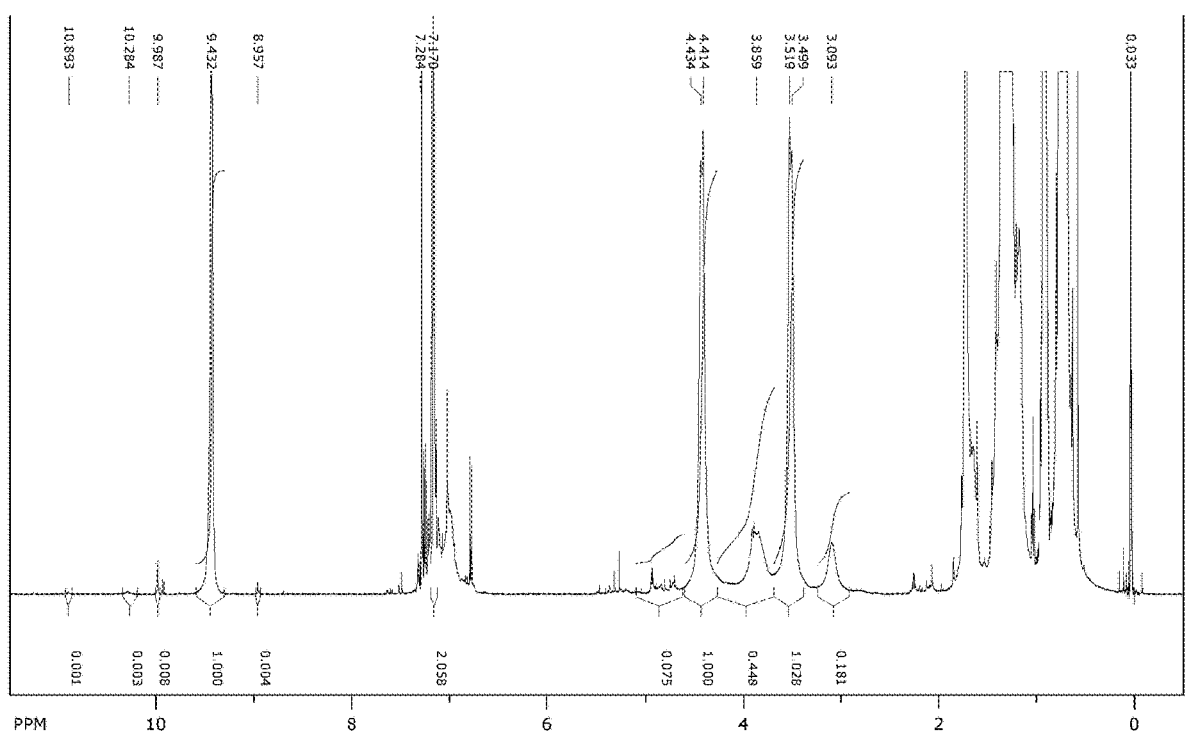
FIG. 23 shows the $^1$H-NMR results of the crude reaction mass prepared from Example 11.

The $^1$H-NMR results of the crude reaction mass are shown in FIG. 23.

This crude reaction mass obtained above was then cooled to about 70-80° C., and was filtered through a Buechner funnel. The filter cake was successively washed with portions of isopropanol (a total of 100.6 g), and dried in the vacuum oven at about 130° C. to result in a product tert-octylcalix[8]arene in an isolated yield of 79.4% (theoretical yield), with an HPLC purity of 97.0% (area % at 281 nm), and 0.13 wt % free PTOP and 0.13 wt % hexadecane (both determined by GC).

Example 12. Synthesis of Para-Cumylcalix[8]Arenes Using Tetramethylammonium Hydroxide (TMAOH) as the Catalyst A 500 ml round bottom flask, equipped with an overhead stirrer, thermocouple, overhead addition tank, moisture trap, and condenser was loaded with 160.1 g para-cumylphenol (PCP) (0.75 mol) and 100.5 g A-150 (Solvesso™ 150 Fluid). A gentle nitrogen flow was applied on the surface of the hot reaction mass and the reactor was heated to about 90° C. When all the PCP and the A-150 formed a clear solution, 5.6 g of TMAOH solution (25 wt % in methanol, 0.015 mol) was added. At about 90° C., a total of 70.7 g of 37 wt % formaldehyde solution (0.87 mol, stabilized with 10-15% methanol) was added within 17 minutes.

After the formaldehyde addition, the reaction was kept at 90° C. for 1 hour. The reaction mixture was then heated to reflux at about 100° C. for a total of 12 hours. At the end of the reflux, the reaction mass was at about 100° C.

Figure 24:
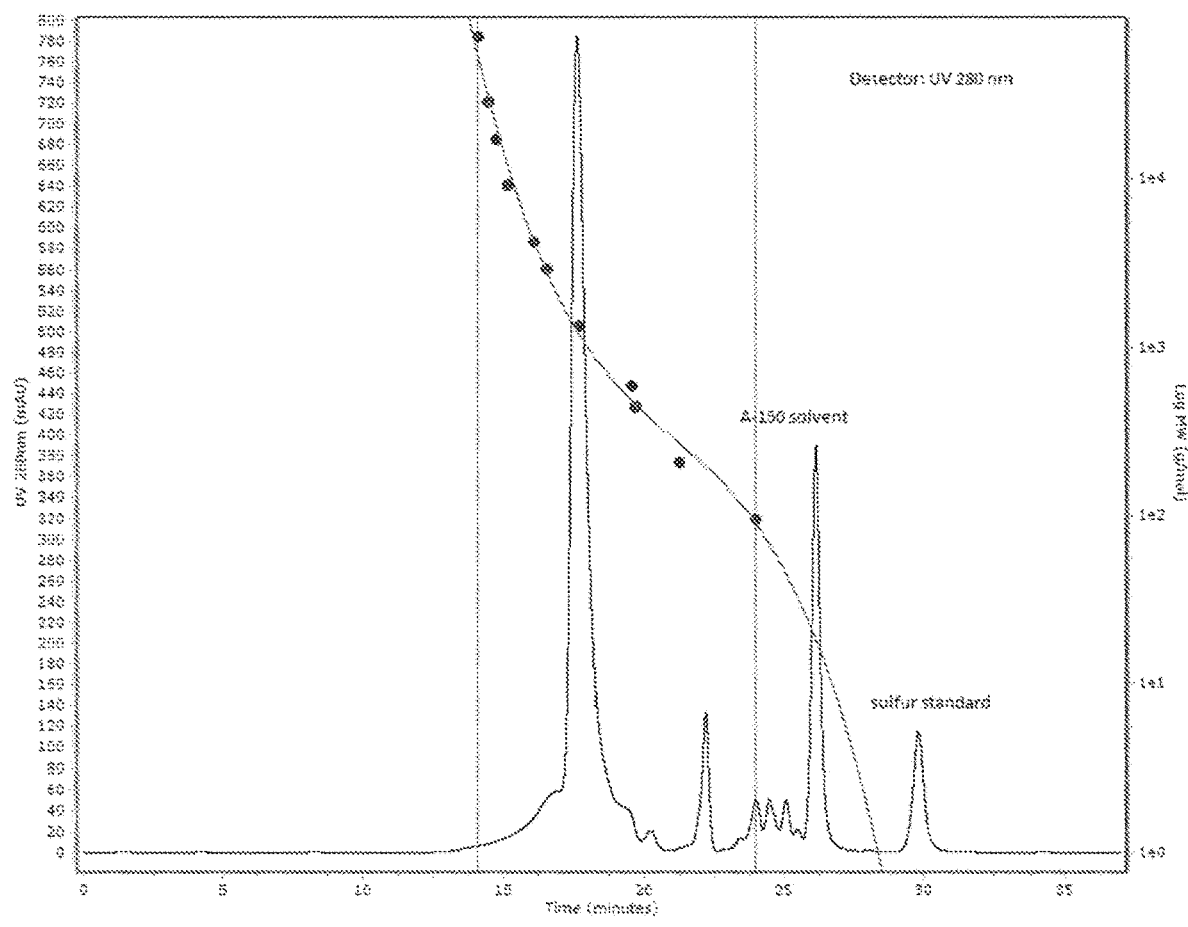
FIG. 24 shows the GPC results of the crude reaction mass prepared from Example 12.

The reaction mass was diluted with 78.9 g more A-150 solvent. The reactor was then heated and the temperature target was set to 145° C. to remove the water (excess formaldehyde and potentially remaining methanol). About 94 minutes after the heating was started, the temperature of the reaction mass reached about 144° C. and was kept for about 10 hours. The crude reaction mass contained 3.25 wt % unreacted para-cumylphenol. The GPC results of the crude reaction mass are shown in FIG. 24.

Figure 25:
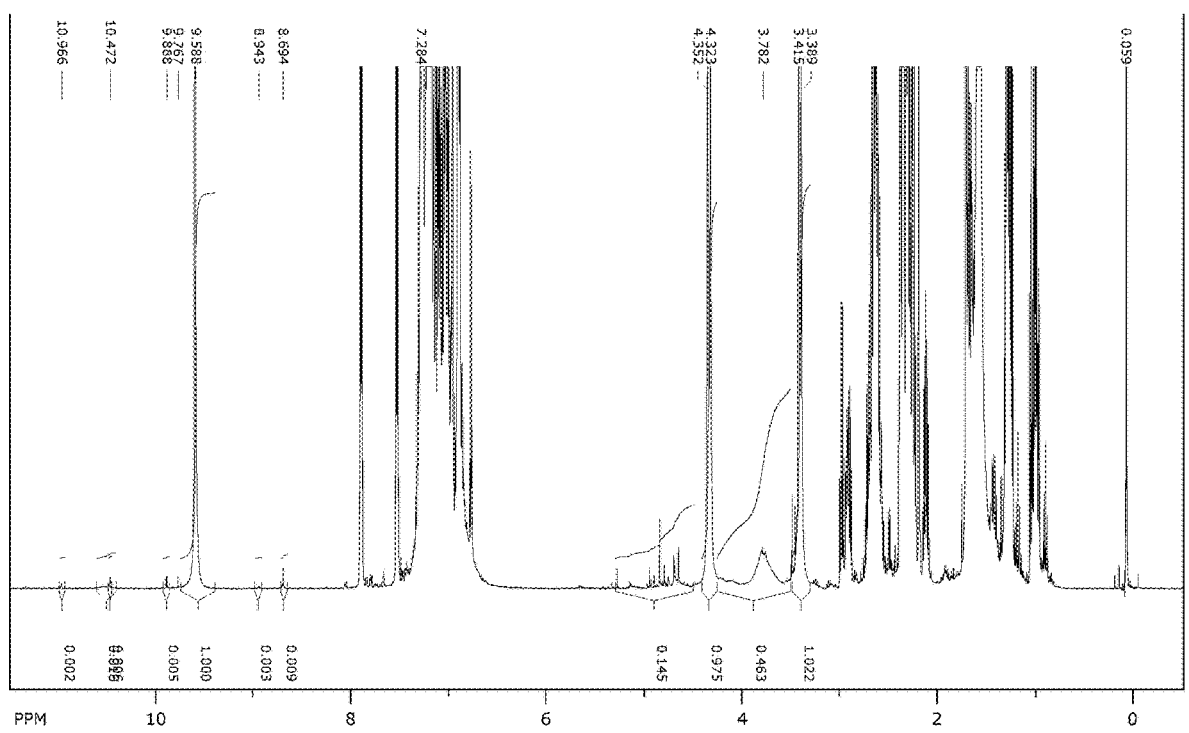
FIG. 25 shows the $^1$H-NMR results of the crude reaction mass prepared from Example 12.

The $^1$H-NMR results of the crude reaction mass are shown in FIG. 25.

This crude reaction mass obtained above was then cooled to about 70-80° C., and the obtained slurry was filtered through a Buechner funnel. The filtered material was successively washed with a first portion of 105.2 g A-150 solvent and a second portion of 78.0 g A-150 solvent, and dried in a vacuum oven at 130° C. The final product para-cumylphenol (113.9 g) was obtained in an isolated yield of 60.6% (theoretical yield) with an HPLC purity of 91.0% (area % at 281 nm) and 0.99 wt % free PCP and less than 0.05 wt % A-150 (both determined by GC). The impurities in the final product may contain some linear resins as well as calix[6]arene and calix[7]arene.

Example 13. Synthesis of Tert-Amylcalix[8]Arenes Using Tetramethylammonium Hydroxide (TMAOH) as the Catalyst A 500 ml round bottom flask, equipped with an overhead stirrer, thermocouple, overhead addition tank, moisture trap, and condenser was loaded with 123.2 g para-tert-amylphenol (PTAP) briquettes (0.75 mol) and 88.6 g A-150 (Solvesso™ 150 Fluid). A gentle nitrogen flow was applied on the surface of the reaction mass and the reactor was heated to about 75° C. Over the course of 3 minutes, 5.5 g of TMAOH solution (25 wt % in methanol, 0.015 mol) was added dropwise. At 90° C., a total of 51.0 g of 50.4 wt % formaldehyde solution (0.86 mol) was added within 7 minutes.

After the formaldehyde addition, the reaction was kept at 90° C. for 1 hour. The reaction mixture was set to reflux conditions and was forcefully heated (e.g., it took about 15 minutes to heat the reaction mixture from room temperature to reach about 100° C. and within 60-120 minutes the pot temperature can reach about 111° C.), while allowing the distillate to return back into the reaction flask. The pot temperature reached to about 115° C. within 4.5 hours of heating and was held at 115° C. for additional 1.5 hours. The crude reaction product contained 0.52 wt % free formaldehyde and 8.93 wt % unreacted para-tert-amylphenol.

The reactor was then heated and the temperature target was set to 145° C. to remove the water. The temperature of the reaction mass was kept at 145° C. for a total of 10 hours until the water and excess formaldehyde were distilled out. The 38.5 g of aqueous distillate removed contained 2.5 g formaldehyde (which corresponds to 9.74% of the starting formaldehyde).

Figure 26:
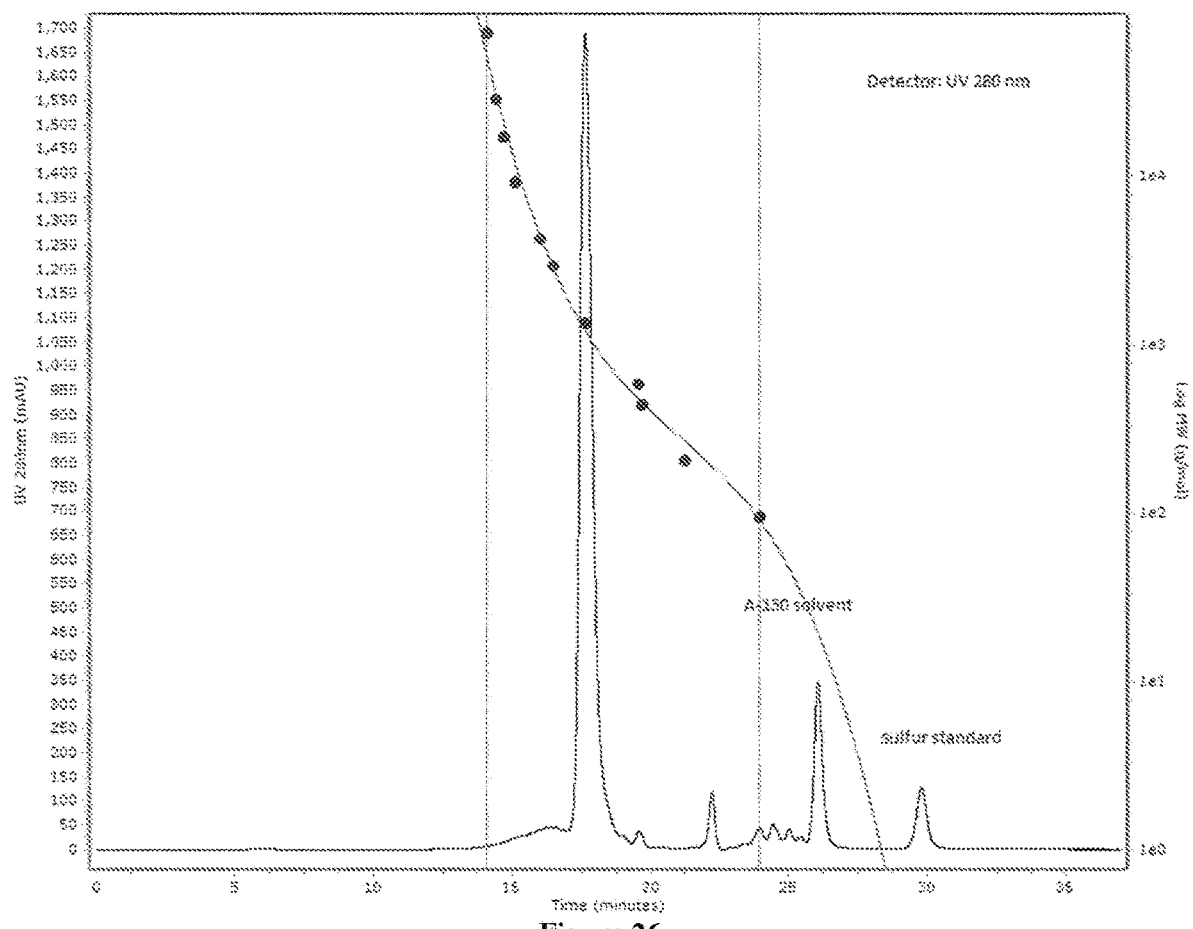
FIG. 26 shows the GPC results of the crude reaction mass prepared from Example 13.

The crude product tert-amylcalix[8]arene was obtained with an HPLC purity of 86.0% (area % at 281 nm) and 1.98 wt % PTAP (which corresponds to 3.6% of the starting PTAP). The solid content of the final calixarene reaction mass was determined to be about 60%. The GPC results of the crude reaction mass are shown in FIG. 26.

This crude reaction mass obtained above was then cooled to about 60-70° C., and was filtered through a Buechner funnel. The filter cake was successively washed with 101.7 g A-150 and dried in vacuum oven at 130° C. to result in a tert-amylcalix[8]arene product in an isolated yield of 81.3% (theoretical yield), with an HPLC purity of 99.0% (area % at 281 nm), 0.44 wt % free PTAP and 1.17 wt % A-150.

Example 14. Synthesis of Tert-Amylcalix[8]Arenes Using Tetramethylammonium Hydroxide (TMAOH) as the Catalyst and Paraformaldehyde as the Aldehyde Source in Diphenylether A 500 ml round bottom flask, equipped with an overhead stirrer, thermocouple, overhead addition tank, moisture trap, and condenser was loaded with 123.2 g para-tert-amylphenol (PTAP) briquettes (0.75 mol), 27.0 g paraformaldehyde (95%, 0.85 mol), and 88.5 g diphenylether. A gentle nitrogen flow was applied on the surface of the reaction mass and the reactor was heated to about 68° C. To the reaction suspension, at a temperature of 68-80° C., 5.5 g of TMAOH solution (25 wt % in methanol, 0.015 mol) was added dropwise over the course of 3 minutes.

The reaction mixture was then further heated with the temperature target set to 145° C. to remove the water through the moisture trap, with the gentle nitrogen flow assisting in transporting the water to the trap. The temperature of the reaction mass reached about 143° C. within 41 minutes, and was kept for about 5 hours between 143-155° C. The 16.0 g aqueous distillate removed contained 2.4 g formaldehyde (which corresponds to 9.4% of the starting formaldehyde).

Figure 27:
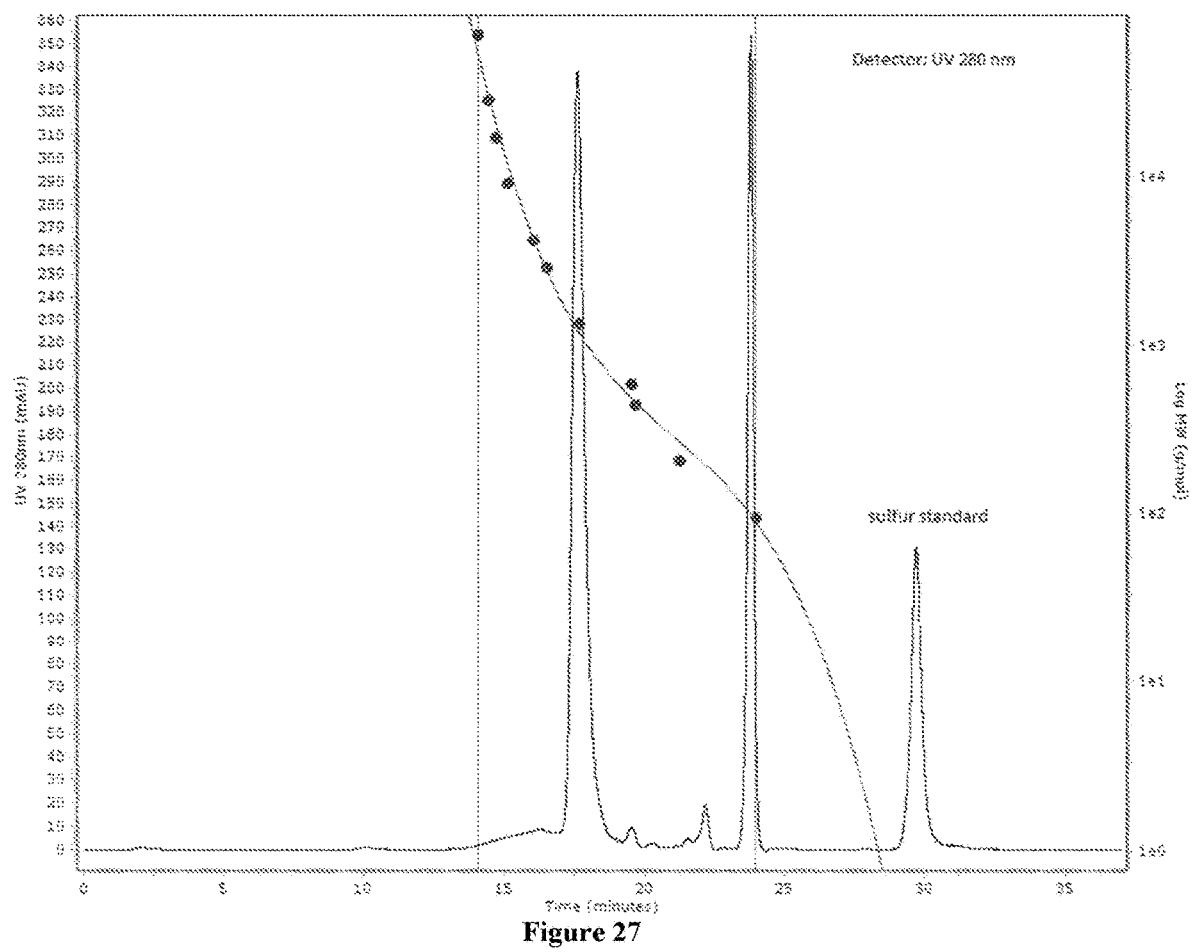
FIG. 27 shows the GPC results of the crude reaction mass prepared from Example 14.

The crude product tert-amylcalix[8]arene was obtained with an HPLC purity of 85.1% (area % at 281 nm) and 1.27 wt % PTAP (which corresponds to 2.3% of the starting PTAP). The solid content of the final calixarene reaction mass was determined to be about 60%. The GPC results of the crude reaction mass are shown in FIG. 27.

This crude reaction mass obtained above was then cooled to about 75° C., and was filtered through a Buechner funnel. The filter cake was successively washed with portions of 108.1 g xylene and dried in vacuum oven at 130° C. to result in a tert-amylcalix[8]arene product in an isolated yield of 82.6% (theoretical yield), with an HPLC purity of 96.5% (area % at 281 nm), 0.09 wt % free PTAP and 3.91% diphenylether.

Example 15. Synthesis of Tert-Amylcalix[8]Arenes Using 4-(dimethylamino)pyridine (DMAP) as the Catalyst

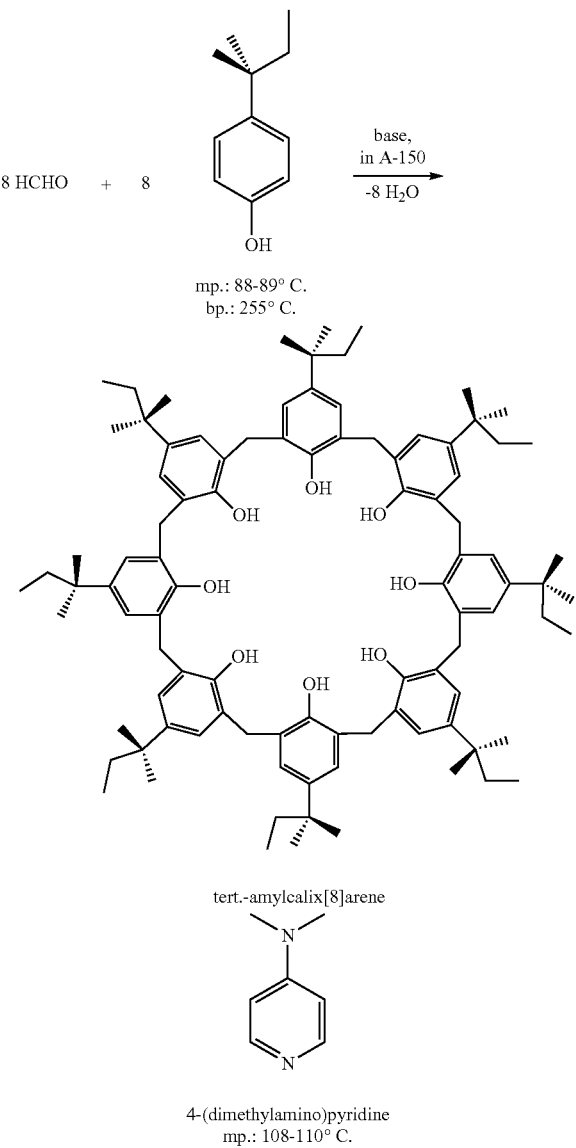

A 500 ml round bottom flask, equipped with an overhead stirrer, thermocouple, overhead addition tank, moisture trap, and condenser was loaded with 123.2 g para-tert-amylphenol (PTAP) briquettes (0.75 mol) and 100.8 g A-150 (Solvesso™ 150 Fluid). A gentle nitrogen flow was applied on the surface of the reaction mass and the reactor was heated to about 90° C. When all the PTAP and the A-150 formed a clear solution, 1.8 g 4-(dimethylamino)pyridine (0.015 mol) was added at about 93° C., and the temperature was held for 46 minutes. At about 73° C., a total of 55.9 g of 45.9 wt % formaldehyde solution (0.85 mol) was added within 17 minutes.

After the formaldehyde addition, the reaction was kept at 90° C. for 1 hour. The reaction mixture was then heated to reflux at about 99° C. for a total of 12 hours. At the end of the reaction, the reaction mass was at about 99° C.

The reaction mass was diluted with 50.1 g more A-150 solvent. The reactor was then heated to distillation conditions with the temperature target set to 145° C. to remove the water. The temperature of the reaction mass was kept at 145° C. for about 10 hours until a lower layer of 35.4 g was removed, which contained 11.6 wt % formaldehyde (which corresponds to 16.0% of the starting formaldehyde). The crude reaction mass contained 0.85 wt % PTAP (which corresponds to 1.9% of the starting PTAP).

This crude reaction mass obtained above was then cooled to about 74° C., and was easily filtered through a Buechner funnel. The filter cake was successively washed with 105.0 g A-150 and dried in vacuum oven at 130° C. to result in a tert-amylcalix[8]arene product in an isolated yield of 79.9% (theoretical yield), with an HPLC purity of 99.0% (area % at 281 nm), 0.18 wt % free PTAP and 0.32 wt % A-150.

Sample Characterization Methods.

The reaction products in above examples were characterized by various methods, including $^1$H-NMR, GPC, and HPLC.

$^1$H-NMR spectra was recorded at 500 MHz frequency in δ (ppm) using CDCl$_3$ as internal standard.

Gel permeation chromatography (GPC) was conducted with a three-column set PLGel 5 μm (500 Å, 100 Å, 50 Å) (column temperature of 40° C.) with the 99/1 THF/MeOH as the mobile phase and the flow rate at 1.0 mL/minute, equipped with a UV detector at 280 nm. The sample concentration was 2.5 mg/mL with 50 μL injection volume.

High-Performance Liquid Chromatography (HPLC) was performed on a Hewlett Packard 1100 Series HPLC System using Agilent InfinityLab Poroshell 120 EC-C18 HPLC columns 3.0×150 mm, 2.7 μm (Agilent Technologies) and a UV detector set at 281 nm. HPLC grade solvents were used. Samples were dissolved in stabilized chloroform (in ethanol or alkane). To obtain a high peak resolution for calixarene compounds with varying ring sizes, particularly from ring size 4 to ring size 8, the following combinations of solvents, gradients, and flow rates were used:

| Flow rate: | 0.4 ml/minute | | |
|---|---|---|---|
| Gradient: | Time (min) | % C | % D |
| | 0 | 90 | 10 |
| | 5 | 90 | 10 |
| | 20 | 80 | 20 |
| | 30 | 40 | 60 |
| | 35 | 20 | 80 |
| | 40 | 20 | 80 |
| | 42 | 90 | 10 |

C = 99/1 acetonitrile/glacial acetic acid;
D = 12:9:1 MeCl$_2$:MTBE (methyl tert butyl ether):glacial acetic acid The examples of the synthesis of the calixarene compounds are summarized in Table 5 below.

TABLE 5

Summary of the examples

| Ex. No. | Phenolic compound | Aldehyde | Solvent | Catalyst | Reflux Time [hours] | Water removal at 140-145° C. [hours] | "Theoretical" solid content [wt %] | Crude calixarene yield [%, based on NMR, GC] |
|---|---|---|---|---|---|---|---|---|
| 1 | PTBP | formaldehyde | A-150 | DBU | 15 | 5 | 57.8 | 78.7 |
| 2 | PTBP | formaldehyde | A-150 | TEAOH | 12 | 10 | 37.5 | 72.9 |
| 3 | PTBP | para-formaldehyde | xylene | TMAOH | — | 10.5 | — | — |
| 4 | PTAP | formaldehyde | A-150 | TMAOH | 12 | 10 | 45.2 | 80.3 |
| 5 | PTOP | formaldehyde | A-150 | TEAOH | 12 | 10 | 60.8 | 78.1 |
| 6 | PTBP | formaldehyde | diphenyl ether | TMAOH | 12 | 8.5 | 32.7 | 85.6 |
| 7 | PTBP | formaldehyde | A-150 | DBU | 15.25 | 6.5 | 68.2[c)] | — |
| 8 | PTBP | formaldehyde | A-150 | TEAOH | 12 | — | — | — |
| 9 | PSBP | formaldehyde | A-150 | TMAOH | 12 | 10 | 37.7 | 76.3 |
| 10 | PTAP | formaldehyde | diphenyl ether/xylene | TMAOH | 12 | 10 | — | — |
| 11 | PTOP | formaldehyde | hexadecane | TEAOH | 12 | 10 | — | — |
| 12 | POP | formaldehyde | A-150 | TMAOH | 12 | 10 | — | — |
| 13 | PTAP | formaldehyde | A-150 | TMAOH | 6 | 10 | — | — |
| 14 | PTAP | para-formaldehyde | diphenyl ether | TMAOH | — | 5 | — | — |
| 15 | PTAP | formaldehyde | A-150 | DMAP | 12 | 10 | — | — |

| | Without filtration treatment | | | With filtration/drying treatment | |
|---|---|---|---|---|---|
| Ex. No. | Crude calix[8]arene yield [%, based on NMR, GC] | Selectivity for calix[8]arene amongst all formed calixarenes [%] | Free phenolic monomer [wt %] | HPLC purity [b)] [%, area % at 281 nm] | Free phenolic monomer [wt %, by GC] |
| 1 | 74.8 | 95 | 2.2 | — | — |
| 2 | 69.3 | 95.1 | 3.82 | 98.8 | <0.05 |
| 3 | — | — | 4.92 | 95.2 | 0.08 |
| 4 | 78.2 | 97.4 | 1.3 | 99.3 | 0.29 |
| 5 | 72.5 | 92.8 | 1.4 | 98.9 | <0.05 |

TABLE 5-continued

| Summary of the examples | | | | | |
|---|---|---|---|---|---|
| 6 | 83.8 | 97.9 | 1.13 | 92.3[a] | 0.12 |
| 7 | — | — | 2.36 | 95.5[d] | — |
| 8 | — | — | — | — | — |
| 9 | 70.8 | 92.8 | 3.43 | 99.2 | <0.05 |
| 10 | — | — | 1.02 | 98.8 | <0.05 |
| 11 | — | — | 0.68 | 97.0 | 0.13 |
| 12 | — | — | 3.25 | 91.0 | 0.99 |
| 13 | — | — | 1.98 | 99.0 | 0.44 |
| 14 | — | — | 1.27 | 96.5 | 0.09 |
| 15 | — | — | 0.85 | 99.0 | 0.18 |

[a] with 5.1% tert-butylcalix[9]arene
[b] HPLC purity of isolated calixarenes
[c] determined experimentally
[d] isolated by preparative column chromatography

We claim:

1. A process for preparing a calixarene compound, comprising:
reacting a phenolic compound and an aldehyde in the presence of at least one nitrogen-containing base as a catalyst to form the calixarene compound,
wherein the phenolic compound is para-nonylphenol (PNP) or para-dodecylphenol (PDDP), and
wherein the process produces a calixarene-containing product having at least 45% solids.

2. The process of claim 1, wherein the process produces a calixarene-containing product having at least 50% solids.

3. The process of claim 1, wherein the nitrogen-containing base is a tetraalkyl ammonium hydroxide, wherein each alkyl moiety in the tetraalkyl ammonium hydroxide is independently $C_1$ to $C_6$ alkyl.

4. The process of claim 3, wherein the tetraalkyl ammonium hydroxide is tetramethyl ammonium hydroxide.

5. The process of claim 1, wherein the nitrogen-containing base is an amidine compound having the formula of

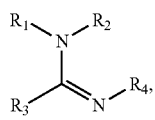

(I)

wherein $R_1$, $R_2$, $R_3$, and $R_4$ are each independently H, alkyl, cycloalkyl, heterocycloalkyl, aryl, or heteroaryl; or any two or more of $R_1$, $R_2$, $R_3$, and $R_4$ can be bonded together to form a five- to nine-membered ring structure.

6. The process of claim 5, wherein the amidine compound is selected from the group consisting of 1,8-diazabicyclo[5.4.0]undec-7-ene (DBU), 1,5-diazabicyclo[4.3.0]non-5-ene (DBN), 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, and 1-ethyl-2-isopropyl-1,4,5,6-tetrahydropyrimidine.

7. The process of claim 6, wherein the amidine compound is DBU.

8. The process of claim 1, wherein the aldehyde is formaldehyde or paraformaldehyde.

9. The process of claim 8, wherein the aldehyde is paraformaldehyde.

10. The process of claim 1, wherein the phenolic compound is PNP.

11. The process of claim 1, wherein the phenolic compound is PDDP.

12. The process of claim 1, wherein the PNP compound or the PDDP compound primarily contains the para isomer of the compound.

13. The process of claim 1, wherein the source of the phenolic compound is either PNP or PDDP.

14. The process of claim 1, wherein the molar ratio of the phenolic compound to the aldehyde ranges from about 1:1.5 to about 1.5:1, and the molar ratio of the phenolic compound to the nitrogen-containing base ranges from about 200:1 to about 20:1.

15. The process of claim 1, wherein the reaction is carried out in the presence of an organic solvent.

16. The process of claim 15, wherein the organic solvent is a mixture further containing an aromatic hydrocarbon.

17. The process of claim 15, wherein the organic solvent is a mixture further containing a straight-chain $C_{11}$ to $C_{20}$ hydrocarbon.

18. The process of claim 15, wherein the mass ratio of the phenolic compound and the organic solvent is no less than 0.5:1.

19. The process of claim 1, wherein the reaction is carried out under reflux conditions.

20. The process of claim 1, wherein the aldehyde is paraformaldehyde and the reaction is carried out without reflux.

21. A phenolic oligomer composition prepared by the process of claim 1.

22. The process of claim 11, wherein the aldehyde is aqueous formaldehyde and the reaction is carried out with a reflux stage.

23. The process of claim 22, wherein, at the reflux stage, the reaction is heated at a temperature higher than the temperature needed for reaching a reflux, to reduce the reaction time at the reflux stage.

24. The process of claim 23, wherein at the reflux stage, the reaction is heated at a temperature about 5-20° C. higher than the temperature needed for reaching a reflux, to reduce the reaction time about 50% of the reaction time typically needed for the reflux stage.

25. The process of claim 22, wherein at the reflux stage, the reaction is heated under pressure, to reduce the reaction time at the reflux stage.

* * * * *